United States Patent
Hall et al.

(10) Patent No.: US 7,700,102 B2
(45) Date of Patent: Apr. 20, 2010

(54) NUCLEIC ACIDS ENCODING CD100 MOLECULES

(75) Inventors: Kathryn T. Hall, Boston, MA (US); Gordon J. Freeman, Brookline, MA (US); Joachim L. Schultze, Cologne (DE); Vassiliki A. Boussiotis, Brookline, MA (US); Lee M. Nadler, Newton, MA (US); Laurence Boumsell, Creteil (FR); Armand Bensussan, Creteil (FR)

(73) Assignees: Dana-Farber Cancer Institute, Boston, MA (US); Institut National de la Sante et de la Recherche Medicale (INSERM), Paris Cedex (FR)

( * ) Notice: Subject to any disclaimer, the term of this patent is extended or adjusted under 35 U.S.C. 154(b) by 1157 days.

(21) Appl. No.: 10/320,769

(22) Filed: Dec. 16, 2002

(65) Prior Publication Data

US 2003/0158402 A1    Aug. 21, 2003

Related U.S. Application Data

(63) Continuation of application No. 08/556,422, filed on Nov. 9, 1995, now Pat. No. 6,576,754.

(51) Int. Cl.
*A61K 39/395* (2006.01)
(52) U.S. Cl. .................. 424/153.1; 424/141.1
(58) Field of Classification Search ........... None
See application file for complete search history.

(56) References Cited

U.S. PATENT DOCUMENTS 5,070,192 A    12/1991 Earnshaw et al.
2006/0233793 A1    10/2006 Belin et al.

FOREIGN PATENT DOCUMENTS

WO    WO 93/14125 A1    7/1993

OTHER PUBLICATIONS

Kumanogoh, A., et al. Int. Immunol. 17(10):1277-1282.*
Li, D.H.-H., et al. Arthit. Rheum. 2008;58(10):3192-3204.*
Swiercz, J.M., et al. J. Biol. Chem. 2008;283(4):1893-1901.*
Bougeret, Cecile et al. (1992) "Increased Surface Expression of a Newly Identified 150-kDa Dimer Early After Human T Lymphocyte Activation" *The Journal of Immunology* 148(2):318-323.
Gouttefangeas, C. et al. (1993) "Differential proliferative responses in subsets of human CD28+ cells delineated by BB27 mAb" *International Immunology* 6(3):423-430.
Herold, C. et al. "CD100 defines a newly identified 150-kDa human lymphocyte surface structure" T-cell Antigens—Papers T1:50-51.
Herold, Cecile et al. (1994) "Activation signals are delivered through two distinct epitopes of CD100, a unique 150 kDa human lymphocyte surface structure previously defined by BB18 mAb" *International Immunology* 7(1):1-8.
Kornbluth et al, *Molecular and Cellular Biology* 8 (12): 5541-5544, Sep. 1988.
Lazar et al. *Mol. Cell Biol.* p. 1247-1252, 1988.
Skolnick et al. *Trends in Biotech.* 18(1):34-39, 2000.
Voet et al. *Biochemistry* p. 126-128 and 228-234, 1990.
Young et al. *Proc. Natl. Acad. Sci. USA* 80: 1194-1196, Mar. 1983.
Database GenBank, Apr. 18, 2005, Adams, R.H., "*M. musculus* mRNA for semaphorin B." Data Accession No. X85991.
Database GenBank, Apr. 24, 1997, Wilson, R.K., "zt85a06.r1" Data Accession No. AA394007.
Database GenBank, Jan. 31, 1997, Strausberg, R., "zs16g08.r1" Data Accession No. AA262446.

* cited by examiner

*Primary Examiner*—G. R Ewoldt
(74) *Attorney, Agent, or Firm*—Alston & Bird LLP

(57) ABSTRACT

Isolated nucleic acid molecules encoding novel CD100 molecules which stimulate a leukocyte response, such as a B cell response, including B cell aggregation, B cell differentiation, B cell survival, and/or T cell proliferation are disclosed. These novel molecules have a certain homology to semaphorins, proteins which are growth cone guidance molecules that are critical for guiding growing axons of neurons to their targets. In addition to isolated nucleic acids molecules, antisense nucleic acid molecules, recombinant expression vectors containing a nucleic acid molecule of the invention, host cells into which the expression vectors have been introduced are also described. The invention further provides isolated CD100 proteins, fusion proteins and active fragments thereof. Diagnostic and therapeutic methods utilizing compositions of the invention are also provided.

6 Claims, 21 Drawing Sheets

```
  1                                                    CTGAGCCGCATCTGCAATAG
 21 CACACTTGCCCGGCCACCTGCTGCCGTGAGCCTTTGCTGCTGAAGCCCCTGGGGTCGCCTCTACCTG
    Met Arg Met Cys Thr Pro Ile Arg Gly Leu Leu Met Ala Leu Ala Val Met    17
 88 ATG AGG ATG TGC ACC CCC ATT AGG GGG CTG CTC ATG GCC CTT GCA GTG ATG
    Phe Gly Thr Ala Met Ala Phe Ala Pro Ile Pro Arg Ile Thr Trp Glu His    34
139 TTT GGG ACA GCG ATG GCA TTT GCA CCC ATA CCC CGG ATC ACC TGG GAG CAC
    Arg Glu Val His Leu Val Gln Phe His Glu Pro Asp Ile Tyr Asn Tyr Ser    51
190 AGA GAG GTG CAC CTG GTG CAG TTT CAT GAG CCA GAC ATC TAC AAC TAC TCA
    Ala Leu Leu Leu Ser Glu Asp Lys Asp Thr Leu Tyr Ile Gly Ala Arg Glu    68
241 GCC TTG CTG CTG AGC GAG GAC AAG GAC ACC TTG TAC ATA GGT GCC CGG GAG
    Ala Val Phe Ala Val Asn Ala Leu Asn Ile Ser Glu Lys Gln His Glu Val    85
292 GCG GTC TTC GCT GTG AAC GCA CTC AAC ATC TCC GAG AAG CAG CAT GAG GTG
    Tyr Trp Lys Val Ser Glu Asp Lys Lys Ala Lys Cys Ala Glu Lys Gly Lys   102
343 TAT TGG AAG GTC TCA GAA GAC AAA AAA GCA AAA TGT GCA GAA AAG GGG AAA
    Ser Lys Gln Thr Glu Cys Leu Asn Tyr Ile Arg Val Leu Gln Pro Leu Ser   119
394 TCA AAA CAG ACA GAG TGC CTC AAC TAC ATC CGG GTG CTG CAG CCA CTC AGC
    Ala Thr Ser Leu Tyr Val Cys Gly Thr Asn Ala Phe Gln Pro Ala Cys Asp   136
445 GCC ACT TCC CTT TAC GTG TGT GGG ACC AAC GCA TTC CAG CCG GCC TGT GAC
    His Leu Asn Leu Thr Ser Phe Lys Phe Leu Gly Lys Asn Glu Asp Gly Lys   153
496 CAC CTG AAC TTA ACA TCC TTT AAG TTT CTG GGG AAA AAT GAA GAT GGC AAA
    Gly Arg Cys Pro Phe Asp Pro Ala His Ser Tyr Thr Ser Val Met Val Asp   170
547 GGA AGA TGT CCC TTT GAC CCA GCA CAC AGC TAC ACA TCC GTC ATG GTT GAT
    Gly Glu Leu Tyr Ser Gly Thr Ser Tyr Asn Phe Leu Gly Ser Glu Pro Ile   187
598 GGA GAA CTT TAT TCG GGG ACG TCG TAT AAT TTT TTG GGA AGT GAA CCC ATC
    Ile Ser Arg Asn Ser Ser His Ser Pro Leu Arg Thr Glu Tyr Ala Ile Pro   204
649 ATC TCC CGA AAT TCT TCC CAC AGT CCT CTG AGG ACA GAA TAT GCA ATC CCT
    Trp Leu Asn Glu Pro Ser Phe Val Phe Ala Asp Val Ile Arg Lys Ser Pro   221
700 TGG CTG AAC GAG CCT AGT TTC GTG TTT GCT GAC GTG ATC CGA AAA AGC CCA
    Asp Ser Pro Asp Gly Glu Asp Asp Arg Val Tyr Phe Phe Phe Thr Glu Val   238
751 GAC AGC CCC GAC GGC GAG GAT GAC AGG GTC TAC TTC TTC TTC ACG GAG GTG
    Ser Val Glu Tyr Glu Phe Val Phe Arg Val Leu Ile Pro Arg Ile Ala Arg   255
802 TCT GTG GAG TAT GAG TTT GTG TTC AGG GTG CTG ATC CCA CGG ATA GCA AGA
    Val Cys Lys Gly Asp Gln Gly Gly Leu Arg Thr Leu Gln Lys Lys Trp Thr   272
853 GTG TGC AAG GGG GAC CAG GGC GGC CTG AGG ACC TTG CAG AAG AAA TGG ACC
    Ser Phe Leu Lys Ala Arg Leu Ile Cys Ser Arg Pro Asp Ser Gly Leu Val   289
904 TCC TTC CTG AAA GCC CGA CTC ATC TGC TCC CGG CCA GAC AGC GGC TTG GTC
    Phe Asn Val Leu Arg Asp Val Phe Val Leu Arg Ser Pro Gly Leu Lys Val   306
955 TTC AAT GTG CTG CGG GAT GTC TTC GTG CTC AGG TCC CCG GGC CTG AAG GTG
    Pro Val Phe Tyr Ala Leu Phe Thr Pro Gln Leu Asn Asn Val Gly Leu Ser   323
1006 CCT GTG TTC TAT GCA CTC TTC ACC CCA CAG CTG AAC AAC GTG GGG CTG TCG
    Ala Val Cys Ala Tyr Asn Leu Ser Thr Ala Glu Glu Val Phe Ser His Gly   340
1057 GCA GTG TGC GCC TAC AAC CTG TCC ACA GCC GAG GAG GTC TTC TCC CAC GGG
    Lys Tyr Met Gln Ser Thr Thr Val Glu Gln Ser His Thr Lys Trp Val Arg   357
1108 AAG TAC ATG CAG AGC ACC ACA GTG GAG CAG TCC CAC ACC AAG TGG GTG CGC
    Tyr Asn Gly Pro Val Pro Lys Pro Arg Pro Gly Ala Cys Ile Asp Ser Glu   374
1159 TAT AAT GGC CCG GTA CCC AAG CCG CGG CCT GGA GCG TGC ATC GAC AGC GAG
    Ala Arg Ala Ala Asn Tyr Thr Ser Ser Leu Asn Leu Pro Asp Lys Thr Leu   391
```

*Fig. 1*

```
1210 GCA CGG GCC GCC AAC TAC ACC AGC TCC TTG AAT TTG CCA GAC AAG ACG CTG
     Gln Phe Val Lys Asp His Pro Leu Met Asp Asp Ser Val Thr Pro Ile Asp    408
1261 CAG TTC GTT AAA GAC CAC CCT TTG ATG GAT GAC TCG GTA ACC CCA ATA GAC
     Asn Arg Pro Arg Leu Ile Lys Lys Asp Val Asn Tyr Thr Gln Ile Val Val    425
1312 AAC AGG CCC AGG TTA ATC AAG AAA GAT GTG AAC TAC ACC CAG ATC GTG GTG
     Asp Arg Thr Gln Ala Leu Asp Gly Thr Val Tyr Asp Val Met Phe Val Ser    442
1363 GAC CGG ACC CAG GCC CTG GAT GGG ACT GTC TAT GAT GTC ATG TTT GTC AGC
     Thr Asp Arg Gly Ala Leu His Lys Ala Ile Ser Leu Glu His Ala Val His    459
1414 ACA GAC CGG GGA GCT CTG CAC AAA GCC ATC AGC CTC GAG CAC GCT GTT CAC
     Ile Ile Glu Glu Thr Gln Leu Phe Gln Asp Phe Glu Pro Val Gln Thr Leu    476
1465 ATC ATC GAG GAG ACC CAG CTC TTC CAG GAC TTT GAG CCA GTC CAG ACC CTG
     Leu Leu Ser Ser Lys Lys Gly Asn Arg Phe Val Tyr Ala Gly Ser Asn Ser    493
1516 CTG CTG TCT TCA AAG AAG GGC AAC AGG TTT GTC TAT GCT GGC TCT AAC TCG
     Gly Val Val Gln Ala Pro Leu Ala Phe Cys Gly Lys His Gly Thr Cys Glu    510
1567 GGC GTG GTC CAG GCC CCG CTG GCC TTC TGT GGG AAG CAC GGC ACC TGC GAG
     Asp Cys Val Leu Ala Arg Asp Pro Tyr Cys Ala Trp Ser Pro Pro Thr Ala    527
1618 GAC TGT GTG CTG GCG CGG GAC CCC TAC TGC GCC TGG AGC CCG CCC ACA GCG
     Thr Cys Val Ala Leu His Gln Thr Glu Ser Pro Ser Arg Gly Leu Ile Gln    544
1669 ACC TGC GTG GCT CTG CAC CAG ACC GAG AGC CCC AGC AGG GGT TTG ATT CAG
     Glu Met Ser Gly Asp Ala Ser Val Cys Pro Asp Lys Ser Lys Gly Ser Tyr    561
1720 GAG ATG AGC GGC GAT GCT TCT GTG TGC CCG GAT AAA AGT AAA GGA AGT TAC
     Arg Gln His Phe Phe Lys His Gly Gly Thr Ala Glu Leu Lys Cys Ser Gln    578
1771 CGG CAG CAT TTT TTC AAG CAC GGT GGC ACA GCG GAA CTG AAA TGC TCC CAA
     Lys Ser Asn Leu Ala Arg Val Phe Trp Lys Phe Gln Asn Gly Val Leu Lys    595
1822 AAA TCC AAC CTG GCC CGG GTC TTT TGG AAG TTC CAG AAT GGC GTG TTG AAG
     Ala Glu Ser Pro Lys Tyr Gly Leu Met Gly Arg Lys Asn Leu Leu Ile Phe    612
1873 GCC GAG AGC CCC AAG TAC GGT CTT ATG GGC AGA AAA AAC TTG CTC ATC TTC
     Asn Leu Ser Glu Gly Asp Ser Gly Val Tyr Gln Cys Leu Ser Glu Glu Arg    629
1924 AAC TTG TCA GAA GGA GAC AGT GGG GTG TAC CAG TGC CTG TCA GAG GAG AGG
     Val Lys Asn Lys Thr Val Phe Gln Val Val Ala Lys His Val Leu Glu Val    646
1975 GTT AAG AAC AAA ACG GTC TTC CAA GTG GTC GCC AAG CAC GTC CTG GAA GTG
     Lys Val Val Pro Lys Pro Val Val Ala Pro Thr Leu Ser Val Val Gln Thr    663
2026 AAG GTG GTT CCA AAG CCC GTA GTG GCC CCC ACC TTG TCA GTT GTT CAG ACA
     Glu Gly Ser Arg Ile Ala Thr Lys Val Leu Val Ala Ser Thr Gln Gly Ser    680
2077 GAA GGT AGT AGG ATT GCC ACC AAA GTG TTG GTG GCA TCC ACC CAA GGG TCT
     Ser Pro Pro Thr Pro Ala Val Gln Ala Thr Ser Ser Gly Ala Ile Thr Leu    697
2128 TCT CCC CCA ACC CCA GCC GTG CAG GCC ACC TCC TCC GGG GCC ATC ACC CTT
     Pro Pro Lys Pro Ala Pro Thr Gly Thr Ser Cys Glu Pro Lys Ile Val Ile    714
2179 CCT CCC AAG CCT GCG CCC ACC GGC ACA TCC TGC GAA CCA AAG ATC GTC ATC
     Asn Thr Val Pro Gln Leu His Ser Glu Lys Thr Met Tyr Leu Lys Ser Ser    731
2230 AAC ACG GTC CCC CAG CTC CAC TCG GAG AAA ACC ATG TAT CTT AAG TCC AGC
     Asp Asn Arg Leu Leu Met Ser Leu Phe Leu Phe Phe Val Leu Phe Leu        748
2281 GAC AAC CGC CTC CTC ATG TCC CTC TTC CTC TTC TTT GTT CTC TTC CTC
     Cys Leu Phe Phe Tyr Asn Cys Tyr Lys Gly Tyr Leu Pro Arg Gln Cys Leu    765
2332 TGC CTC TTT TTC TAC AAC TGC TAT AAG GGA TAC CTG CCC AGA CAG TGC TTG
     Lys Phe Arg Ser Ala Leu Leu Ile Gly Lys Lys Lys Pro Lys Ser Asp Phe    782
```

```
2383 AAA TTC CGC TCG GCC CTA CTA ATT GGG AAG AAG AAG CCC AAG TCA GAT TTC
     Cys Asp Arg Glu Gln Ser Leu Lys Glu Thr Leu Val Glu Pro Gly Ser Phe    799
2434 TGT GAC CGT GAG CAG AGC CTG AAG GAG ACG TTA GTA GAG CCA GGG AGC TTC
     Ser Gln Gln Asn Gly Glu His Pro Lys Pro Ala Leu Asp Thr Gly Tyr Glu    816
2485 TCC CAG CAG AAT GGG GAG CAC CCC AAG CCA GCC CTG GAC ACC GGC TAT GAG
     Thr Glu Gln Asp Thr Ile Thr Ser Lys Val Pro Thr Asp Arg Glu Asp Ser    833
2536 ACC GAG CAA GAC ACC ATC ACC AGC AAA GTC CCC ACG GAT AGG GAG GAC TCA
     Gln Arg Ile Asp Asp Leu Ser Ala Arg Asp Lys Pro Phe Asp Val Lys Cys    850
2587 CAG AGG ATC GAC GAC CTT TCT GCC AGG GAC AAG CCC TTT GAC GTC AAG TGT
     Glu Leu Lys Phe Ala Asp Ser Asp Ala Asp Gly Asp Stop                   862
2638 GAG CTG AAG TTC GCT GAC TCA GAC GCA GAT GGA GAC TGA GGCCGGCTGTGCATC
2692 CCCGCTGGTGCCTCGGCTGCGACGTGTCCAGGCGTGGAGAGTTTTGTGTTTCTCCTGTTCAGTATCC
2759 GAGTCTCGTGCAGTGCTGCGTAGGTTAGCCCGCATCGTGCAGACAACCTCAGTCCTCTTGTCTATTT
2826 TCTCTTGGGTTGAGCCTGTGACTTGGTTTCTCTTTGTCCTTTTGGAAAAATGACAAGCATTGCATCC
2893 CAGTCTTGTGTTCCGAAGTCAGTCGGAGTACTTGAAGAAGGCCCACGGGCGGCACGGAGTTCCTGAG
2960 CCCTTTCTGTAGTGGGGGAAAGGTGGCTGGACCTCTGTTGGCTGAGAAGAGCATCCCTTCAGCTTCC
3027 CCTCCCCGTAGCAGCCACTAAAAGATTATTTAATTCCAGATTGGAAATGACATTTTAGTTTATCAGA
3094 TTGGTAACTTATCGCCTGTTGTCCAGATTGGCACGAACCTTTTCTTCCACTTAATTATTTTTTTAGG
3161 ATTTTGCTTTCATTGTGTTTATGTCATGGGTCATTTTTTTTTAGTTACAGAAGCAGTTGTGTTAATA
3228 TTTAGAAGAAGATGTATATCTTCCAGATTTTGTTATATATTTGGCATAAAATACGGCTTACGTTGCT
3295 TAAGATTCTCAGGGATAAACTTCCTTTTGCTAAATGCATTCTTTCTGCTTTTAGAAATGTAGACATA
3362 AACACTCCCCGGAGCCCACTCACCTTTTTTCTTTTTTCTTTTTTTTTTTTTAACTTTATTCCTTGAGG
3429 GAAGCATTGTTTTTGGAGAGATTTTCTTTCTGTACTTCGTTTTACTTTTCTTTTTTTTTAACTTTTA
3496 CTCTCTCGAAGAAGAGGACCTTCCCACATCCACGAGGTGGGTTTTGAGCAAGGGAAGGTAGCCTGGA
3563 TGAGCTGAGTGGAGCCAGGCTGGCCCAGAGCTGAGATGGGAGTGCGGTACAATCTGGAGCCCACAGC
3630 TGTCGGTCAGAACCTCCTGTGAGACAGATGGAACCTTCACAAGGGCGCCTTTGGTTCTCTGAACATC
3697 TCCTTTCTCTTCTTGCTTCAATTGCTTACCCACTGCCTGCCCAGACTTTCTATCCAGCCTCACTGAG
3764 CTGCCCACTACTGGAAGGGAACTGGGCCTCGGTGGCCGGGGCCGCGAGCTGTGACCACAGCACCCTC
3831 AAGCATACGGCGCTGTTCCTGCCACTGTCCTGAAGATGTGAATGGGTGGTACGATTTCAACACTGGT
3898 TAATTTCACACTCCATCTCCCCGCTTTGTAAATACCCATCGGGAAGAGACTTTTTTTCCATGGTGAA
3965 GAGCAATAAACTCTGGATGTTTGTGCGCGTGTGTGGACAGTCTTATCTTCCAGCATGATAGGATTTG
4032 ACCATTTTGGTGTAAACATTTGTGTTTTATAAGATTTACCTTGTTTTTATTTTTCTACTTTGAATTG
4099 TATACATTTGGAAAGTACCCAAATAAATGAGAAGCTTCTATCCTTAAAAAAAAAAAAAAA
```

*Fig. 1*
(continued)

| | | |
|---|---|---|
| CD100 | MRMCTPIRGLMALAVMFGTAMAFAPIPRITWEHREVHLV | 40 |
| H-SEMA III | MGWLTRIIVCLFWGVLLTARANYQNGKNNVPRLKLSYKEML | 40 |
| M-SEMA C | EERLI | 5 |
| | | |
| CD100 | 41 Q-----FHE-PDIYNYSALLLSEDKDTLYIGAREAVFAV | 73 |
| H-SEMA III | 41 ESNNVITFNGLANSSSYHTFLLDEERSRLYVGAKDHIFSF | 80 |
| M-SEMA C | 6 ---R---KFEA-ENISNYTALLSQDGKTLYVGAREALFAL | 40 |
| | * | |
| CD100 | 74 NA-LN---ISEKQHEVYWKVSEDKRAKCAEKGKSKQTECLN | 110 |
| H-SEMA III | 81 D----LVNIKDFQKIVWPVSYTRRDECKWAGKDILKECAN | 116 |
| M-SEMA C | 41 NSNLSFLPGGEYQELLWSADADRKQQCSFKGKDPKRDCQN | 80 |
| | | |
| CD100 | 111 YIRVLQPLSATTSLYVCGTNAFQPACDHLNLTS----FK | 144 |
| H-SEMA III | 117 FIKVLKAYNQTHLYACGTGAFHPICTYIEIGHHPEDNIFK | 156 |
| M-SEMA C | 81 YIKTLLPLNSSHLTCGTAAFSPLCAYIHIAS----FT | 114 |
| | | |
| CD100 | 145 FLGKN------EDGKGRCPFDPAHSYTSVMDGELYSGTS | 178 |
| H-SEMA III | 157 LENSH------FENGRGKSPYDPKLLTASLLIDGELYSGTA | 191 |
| M-SEMA C | 115 LAQDEAGNVILEDGKGHCPFDPNFKSTALVDGELYTGTIV | 154 |
| | | |
| CD100 | 179 YNFLGSEPIISRNSSHS-PLRTE-YAIPWLNEPSFVFADV | 216 |
| H-SEMA III | 192 ADFMGRDFAIFRTLGHHPIRTEQHDSRWLNDPKFISAHL | 231 |
| M-SEMA C | 155 SSFQGNDPAISRSQSSR-PTKTE-SSLNWLQDPAFVASAT | 192 |

Fig. 2

```
CD100   217  IRKSPDSPDGEDDRVYFFFTEVSVEYEFVFRVLIPRIARV  256
H-SEMA III 232 ISES-DNP--EDDKVYFFFRENAIDGEHSGKATHARIGQI  268
M-SEMA C   193 SPESLGSPIGDDDKTYFFFSETGQEFEFENTIVSRVARV   232

CD100   257  CKGDQGGLRTLQKKWTSFLKARLICSRPD-SGLV--FNVL  293
H-SEMA III 269 CKNDFGGHRSLVNKWTITFLKARLICSVPGPNGIDTHFDEL 308
M-SEMA C   233 CKGDEGGERVLQRWTSFLKAQLLCSRPD-DGFP--FNVL  269

CD100   294  RDVFVLR--SPGLKMPVFYALFTPQLNNVGL--SAVCAYN 329
H-SEMA III 309 QDVFLMNFKDP--KNPVVYGVFIT--SSNIFKGSAVCMYS 344
M-SEMA C   270 QDVFTLNPNPQDWRKTLSIGVFTSQWHRGTTEGSAICVFT 309

CD100   330  LSTAEEVFSHGKYMQSTTVEQSHTKWVRYNGPVPKPRPGA 369
H-SEMA III 345 MSDVRRVFL-IGPYAHR---DGPNYQWVPYQGRVPYPRPGT 380
M-SEMA C   310 MNDVQKAFI-DGLYKK---VNRETQQWYTETHQVPTPRPGA 345

CD100   370  CIDSEARAANYTSSLNLPDKTLQFVKDHPLMDDSVTPIDN 409
H-SEMA III 381 CPSKT--FGGFDSTKDLPDDMITFARSHPAMYNPVFPMNIN 418
M-SEMA C   346 CITNSARERKINSSLQLPDRVLNFLKDHFLMDG---QVRS 382

CD100   410  RPRLIKKDVNYT--QIVVDRTQALDGTVYDVMFVSTDRGA 447
H-SEMA III 419 RPIVIKTDVNYQFTQIVVDRVDAEDGQ--YDVMFIGTDVGT 457
M-SEMA C   383 RLLLLQPRARYQ--RVAVHRVPGLHSTI-YDVLFLGTGDGR 419
```

*Fig. 2*
(continued)

```
CD100    448  LHKAISLEHAV-----HIIEETQLFQDFEPVQTLLSSK           481
H-SEMA III 458 VLKVVSIPKETWYDLEEVLLEEMTVFREPTAISAMELSTK        497
M-SEMA C   420 LHKAVTLSSRV-----HIIEELQIFPQGQPVQNLLDSH          453

CD100    482  KGNRFVYAGSNSGVVQAPLAFCGKHG-TCEDCVLARDPYC        520
H-SEMA III 498 QQQ--LYIGSTAGVAQLPLHRCDIYGKACAECCLARDPYC        535
M-SEMA C   454 GG---LYASSHSGVVQVPVANCSLYP-TCGDCLLARDPYC        490

CD100    521  AWSPPTATCVALHQTESPSRGLIQEMSGDA--SVCPDKSK        558
H-SEMA III 536 AWDGSAC--SRYFPTAKRRTRRQDIRNGDPLTHCSDLHH         572
M-SEMA C   491 AWTGSACRLASLYQPDLASRPWTQDIEGASVKELCKN---        527
                                                        *

CD100    559  GSYRQHF------FKHGGTAE-LKCSQKSNLARVF             586
H-SEMA III 573 DNHHGH------SPEERIIYGVENSSTFLECSPKSQRALVY       607
M-SEMA C   528 SSYKARELVPGKPCKQVQIQPNTVNT-LACPLLSNLATRL        566

CD100    587  WKFQ--NGVLKAES--PKYGLMGRKNLLIFNLSEGDSGVY        622
H-SEMA III 608 WQFQRRNEERKEEITRVDDHIIRTDQGLLRSLQQKDSGNY        647
M-SEMA C   567 W-VH--NGAPVNAS--ASCRVLPTGDLLLVG-SQQGLGVF        600

CD100    623  QCLSEERVKNKTVFQVVAKHVLEVKVVPKPVVAPTLSVVQ        662
H-SEMA III 648 LCHAVEHG                                        654
M-SEMA C   601 QCWSIEEG                                        607
```

*Fig. 2*
(continued)

| | | |
|---|---|---|
| CD100 | 663 | TEGSRIATKVLVASTQGSSPPTPAVQATSSGAITLPPKPA 702 |
| CD100 | 703 | PTGTSCEPKIVINTVPQLHSEKTMYLKSSDNRLLMSLFLF 742 |
| CD100 | 713 | FFVLFLCLFFYNCYKGYLPRQCLKFRSALLIGKKKPKSDF 782 |
| CD100 | 783 | CDREQSLKETLVEPGSFSQQNGEHPKPALDTGYETEQDTI 822 |
| CD100 | 823 | TSKVPTDREDSQRIDDLSARDKPFDVKCELKFADSDADGDI 863 |

*Fig. 2*
(continued)

```
                                                                        10         20
                                                                         |          |
                                              DDKIYFFFTEVSVEYEFVGKLMIPRIAR
                                              ::::::::::::::::::::: :::::
GELYSGTSYNFLGSEPIISRNSSHSPLRTEYAIPWLNEPSFVFADVIRKSPDSPDGEDDRVYFFFTEVSVEYEFVFRVLIPRIAR
         |         |         |         |         |         |         |         |
        180       190       200       210       220       230       240       250

10         20         30         40         50         60         70
                 |          |          |          |          |          |          |
         VCKRDQGGLRTLQKKWTSFLKARLICTIPDKNLIFNIINDVFTLKSPTLKEPVIYGVFTPQLNNVGLSAVCAYNLSAVEEVFSKG
         :: :: :::::::::::::::::::::::: ::::::::::::::::::::::::::::::::::::::::::::::::::
         VCKGDQGGLRTLQKKWTSFLKARLICSRPDSGLVFNVLRDVFVLRSPGLKVPVFYALFTPQLNNVGLSAVCAYNLSTAEEVFSHG
                  |         |         |         |         |         |         |         |
                 260       270       280       290       300       310       320       330  340

80         90        100        110        120        130        140        150
          |          |          |          |          |          |          |          |
         KYMQSATVEQSHTKWVRYNGEIPNPRPGACINNEARALNYYTSLNLPDKTLQFVKDHPLMDDSVTPVGDRPRLVKRDVKYTQIVV
         ::::: :::: ::::::::::::: ::::::::::::::::::::::::::::::::::::::::::::: : ::::::::::
         KYMQSTTVEQSHTKWVRYNGPVPKPRPGACIDSEARAAANYTSSINLPDKTLQFVKDHPLMDDSVTPIDNRPRLIKKDVNYTQIVV
                  |         |         |         |         |         |         |         |
                 350       360       370       380       390       400       410       420
```

*Fig. 4*

```
         200       210       220       230       240       250       260       270       280
          |         |         |         |         |         |         |         |         |
      DRVRALNGTIYDVMFISTDQGALHKAISYENGMHIIEETQLFPKFEPVQTLLLSSKKSRRYLYAGSNSGVVQSPVAFCDTYTTCF
      ················································································
      DRTQALDGTVYDVMFVSTDRGALHKAISLEHAVHIIEETQLFQDFEPVQTLLLSSKKGNRFVYAGSNSGVVQAPLAFCGKHGTCE
          |         |         |         |         |         |         |         |         |
         430       440       450       460       470       480       490       500       510

290
          |
      DCVLARDPYCAW
      ············
      DCVLARDPYCAWSPPTATCVALHQTESPSRGLIQEMSGDASVCPDKSKGSYRQHFFKHGGTAELKCSQKSNLARVFWKFQNGVLK
          |         |         |         |         |         |         |         |
         520       530       540       550       560       570       580       590
```

*Fig. 4*
*(continued)*

SEQUENCE LISTING

<160> NUMBER OF SEQ ID NOS: 7

<210> SEQ ID NO 1
<211> LENGTH: 4157
<212> TYPE: DNA
<213> ORGANISM: Homo sapiens

<400> SEQUENCE: 1

```
ctgagccgca tctgcaatag cacacttgcc cggccacctg ctgccgtgag cctttgctgc      60
tgaagcccct ggggtcgcct ctacctgatg aggatgtgca cccccattag ggggctgctc     120
atggcccttg cagtgatgtt tgggacagcg atggcatttg cacccatacc ccggatcacc     180
tgggagcaca gagaggtgca cctggtgcag tttcatgagc cagacatcta caactactca     240
gccttgctgc tgagcgagga caaggacacc ttgtacatag gtgcccggga ggcggtcttc     300
gctgtgaacg cactcaacat ctccgagaag cagcatgagg tgtattggaa ggtctcagaa     360
gacaaaaaag caaaatgtgc agaaaagggg aaatcaaaac agacagagtg cctcaactac     420
atccgggtgc tgcagccact cagcgccact tcccttacg tgtgtgggac caacgcattc     480
cagccggcct gtgaccacct gaacttaaca tcctttaagt ttctggggaa aaatgaagat     540
```

```
ggcaaaggaa gatgtcccct tgacccagca cacagctaca catccgtcat ggttgatgga      600
gaactttatt cggggacgtc gtataatttt ttgggaagtg aacccatcat ctcccgaaat      660
tcttcccaca gtcctctgag gacagaatat gcaatccctt ggctgaacga gcctagtttc      720
gtgtttgctg acgtgatccg aaaaagccca gacagccccg acggcgagga tgacagggtc      780
tacttcttct tcacggaggt gtctgtggag tatgagtttg tgttcagggt gctgatccca      840
cggatagcaa gagtgtgcaa gggggaccag ggcggcctga ggaccttgca agagaaatgg      900
acctccttcc tgaaagcccg actcatctgc tcccggccag acagcggctt ggtcttcaat      960
gtgctgcggg atgtcttcgt gctcaggtcc ccgggcctga aggtgcctgt gttctatgca     1020
ctcttcaccc cacagctgaa caacgtgggg ctgtcggcag tgtgcgccta caacctgtcc     1080
acagccgagg aggtcttctc ccacgggaag tacatgcaga gcaccacagt ggagcagtcc     1140
cacaccaagt gggtgcgcta taatggcccg gtacccaagc cgcggcctgg agcgtgcatc     1200
gacagcgagg cacgggccgc caactacacc agctccttga atttgccaga caagacgctg     1260
cagttcgtta aagaccaccc tttgatggat gactcggtaa ccccaataga caacaggccc     1320
aggttaatca agaaagatgt gaactacacc cagatcgtgg tggaccggac ccaggccctg     1380
gatgggagtg tctatgatgt catgtttgtc agcacagacc ggggagctct gcacaaagcc     1440
atcagcctcg agcacgctgt tcacatcatc gaggagaccc agctcttcca ggactttgag     1500
ccagtccaga ccctgctgct gtcttcaaag aagggcaaca ggtttgtcta tgctggctct     1560
aactcgggcg tggtccaggc cccgctggcc ttctgtggga agcacggcac ctgcgaggac     1620
tgtgtgctgg cgcgggaccc ctactgcgcc tggagcccgc ccacagcgac ctgcgtggct     1680
ctgcaccaga ccgagagccc cagcaggggt ttgattcagg agatgagcgg cgatgcttct     1740
gtgtgcccgg ataaaagtaa aggaagttac cggcagcatt ttttcaagca cggtggcaca     1800
gcggaactga aatgctccca aaaatccaac ctggcccggg tcttttggaa gttccagaat     1860
ggcgtgttga aggccgagag ccccaagtac ggtcttatgg cagaaaaaaa cttgctcatc     1920
ttcaacttgt cagaaggaga cagtgggggtg taccagtgcc tgtcagagga gagggttaag     1980
aacaaaacgg tcttccaagt ggtcgccaag cacgtcctgg aagtgaaggt ggttccaaag     2040
cccgtagtgg cccccacctt gtcagttgtt cagacagaag gtagtaggat tgccaccaaa     2100
gtgttggtgg catccaccca agggtcttct ccccccaaccc cagccgtgca ggccacctcc     2160
tccggggcca tcacccttcc tcccaagcct gcgcccaccg gcacatcctg cgaaccaaag     2220
atcgtcatca acacggtccc ccagctccac tcggagaaaa ccatgtatct taagtccagc     2280
gacaaccgcc tcctcatgtc cctcttcctc ttcttctttg ttctcttcct ctgcctcttt     2340
ttctacaact gctataaggg atacctgccc agacagtgct tgaaattccg ctcggcccta     2400
ctaattggga agaagaagcc caagtcagat ttctgtgacc gtgagcagag cctgaaggag     2460
acgttagtag agccagggag cttctcccag cagaatgggg agcaccccaa gccagccctg     2520
gacaccggct atgagaccga gcaagacacc atcaccagca agtccccac ggataggag      2580 gactcacaga ggatcgacga cctttctgcc agggacaagc cctttgacgt caagtgtgag     2640
ctgaagttcg ctgactcaga cgcagatgga gactgaggcc ggctgtgcat ccccgctggt     2700
gcctcggctg cgacgtgtcc aggcgtggag agttttgtgt ttctcctgtt cagtatccga     2760
gtctcgtgca gtgctgcgta ggttagcccg catcgtgcag acaacctcag tcctcttgtc     2820
tattttctct tgggttgagc ctgtgacttg gtttctcttt gtccttttgg aaaaatgaca     2880
```

```
agcattgcat cccagtcttg tgttccgaag tcagtcggag tacttgaaga aggcccacgg    2940
gcggcacgga gttcctgagc cctttctgta gtggggaaaa ggtggctgga cctctgttgg    3000
ctgagaagag catcccttca gcttcccctc cccgtagcag ccactaaaag attatttaat    3060
tccagattgg aaatgacatt ttagtttatc agattggtaa cttatcgcct gttgtccaga    3120
ttggcacgaa cctttctctc cacttaatta ttttttttagg attttgcttt gattgtgttt    3180
atgtcatggg tcattttttt ttagttacag aagcagttgt gttaatattt agaagaagat    3240
gtatatcttc cagattttgt tatatatttg cataaaata cggcttacgt tgcttaagat       3300
tctcagggat aaacttcctt ttgctaaatg cattctttct gcttttagaa atgtagacat    3360
aaacactccc cggagcccac tcacctttt tcttttctt tttttttttt taactttatt        3420
ccttgaggga agcattgttt ttggagagat tttctttctg tacttcgttt tactttttctt    3480 tttttttaac ttttactctc tcgaagaaga ggaccttccc acatccacga ggtgggtttt    3540
gagcaaggga aggtagcctg gatgagctga gtggagccag gctggcccag agctgagatg    3600
ggagtgcggt acaatctgga gcccacagct gtcggtcaga acctcctgtg agacagatgg    3660
aaccttcaca agggcgcctt tggttctctg aacatctcct ttctcttctt gcttcaattg    3720
cttacccact gcctgcccag actttctatc cagcctcact gagctgccca ctactggaag    3780
ggaactgggc tcggtggcc ggggccgcga gctgtgacca cagcaccctc aagcatacgg      3840
cgctgttcct gccactgtcc tgaagatgtg aatgggtggt acgatttcaa cactggttaa    3900
tttcacactc catctccccg ctttgtaaat acccatcggg aagagacttt ttttccatgg    3960
tgaagagcaa taaactctgg atgtttgtgc gcgtgtgtgg acagtcttat cttccagcat    4020
gataggattt gaccattttg gtgtaaacat ttgtgtttta aagatttac cttgtttta        4080 tttttctact ttgaattgta tacatttgga aagtacccaa ataaatgaga agcttctatc    4140
cttaaaaaaa aaaaaaa                                                    4157
```

<210> SEQ ID NO 2
<211> LENGTH: 862
<212> TYPE: PRT
<213> ORGANISM: Homo sapiens

<400> SEQUENCE: 2

```
Met Arg Met Cys Thr Pro Ile Arg Gly Leu Leu Met Ala Leu Ala Val
 1               5                  10                  15

Met Phe Gly Thr Ala Met Ala Phe Ala Pro Ile Pro Arg Ile Thr Trp
                20                  25                  30

Glu His Arg Glu Val His Leu Val Gln Phe His Glu Pro Asp Ile Tyr
            35                  40                  45

Asn Tyr Ser Ala Leu Leu Leu Ser Glu Asp Lys Asp Thr Leu Tyr Ile
        50                  55                  60

Gly Ala Arg Glu Ala Val Phe Ala Val Asn Ala Leu Asn Ile Ser Glu
 65                  70                  75                  80

Lys Gln His Glu Val Tyr Trp Lys Val Ser Glu Asp Lys Ala Lys
                85                  90                  95

Cys Ala Glu Lys Gly Lys Ser Lys Gln Thr Glu Cys Leu Asn Tyr Ile
            100                 105                 110

Arg Val Leu Gln Pro Leu Ser Ala Thr Ser Leu Tyr Val Cys Gly Thr
        115                 120                 125

Asn Ala Phe Gln Pro Ala Cys Asp His Leu Asn Leu Thr Ser Phe Lys
    130                 135                 140
```

-continued

```
Phe Leu Gly Lys Asn Glu Asp Gly Lys Gly Arg Cys Pro Phe Asp Pro
145                 150                 155                 160

Ala His Ser Tyr Thr Ser Val Met Val Asp Gly Glu Leu Tyr Ser Gly
                165                 170                 175

Thr Ser Tyr Asn Phe Leu Gly Ser Glu Pro Ile Ile Ser Arg Asn Ser
            180                 185                 190

Ser His Ser Pro Leu Arg Thr Glu Tyr Ala Ile Pro Trp Leu Asn Glu
        195                 200                 205

Pro Ser Phe Val Phe Ala Asp Val Ile Arg Lys Ser Pro Asp Ser Pro
210                 215                 220

Asp Gly Glu Asp Asp Arg Val Tyr Phe Phe Thr Glu Val Ser Val
225                 230                 235                 240

Glu Tyr Glu Phe Val Phe Arg Val Leu Ile Pro Arg Ile Ala Arg Val
                245                 250                 255

Cys Lys Gly Asp Gln Gly Gly Leu Arg Thr Leu Gln Lys Lys Trp Thr
            260                 265                 270

Ser Phe Leu Lys Ala Arg Leu Ile Cys Ser Arg Pro Asp Ser Gly Leu
        275                 280                 285

Val Phe Asn Val Leu Arg Asp Val Phe Val Leu Arg Ser Pro Gly Leu
290                 295                 300

Lys Val Pro Val Phe Tyr Ala Leu Phe Thr Pro Gln Leu Asn Asn Val
305                 310                 315                 320

Gly Leu Ser Ala Val Cys Ala Tyr Asn Leu Ser Thr Ala Glu Glu Val
                325                 330                 335

Phe Ser His Gly Lys Tyr Met Gln Ser Thr Thr Val Glu Gln Ser His
            340                 345                 350

Thr Lys Trp Val Arg Tyr Asn Gly Pro Val Pro Lys Pro Arg Pro Gly
        355                 360                 365

Ala Cys Ile Asp Ser Glu Ala Arg Ala Ala Asn Tyr Thr Ser Ser Leu
370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Arg Leu Ile Lys Lys
                405                 410                 415

Asp Val Asn Tyr Thr Gln Ile Val Val Asp Arg Thr Gln Ala Leu Asp
            420                 425                 430

Gly Ser Val Tyr Asp Val Met Phe Val Ser Thr Asp Arg Gly Ala Leu
        435                 440                 445

His Lys Ala Ile Ser Leu Glu His Ala Val His Ile Ile Glu Glu Thr
450                 455                 460

Gln Leu Phe Gln Asp Phe Glu Pro Val Gln Thr Leu Leu Leu Ser Ser
465                 470                 475                 480

Lys Lys Gly Asn Arg Phe Val Tyr Ala Gly Ser Asn Ser Gly Val Val
                485                 490                 495

Gln Ala Pro Leu Ala Phe Cys Gly Lys His Gly Thr Cys Glu Asp Cys
            500                 505                 510

Val Leu Ala Arg Asp Pro Tyr Cys Ala Trp Ser Pro Pro Thr Ala Thr
        515                 520                 525

Cys Val Ala Leu His Gln Thr Glu Ser Pro Ser Arg Gly Leu Ile Gln
530                 535                 540

Glu Met Ser Gly Asp Ala Ser Val Cys Pro Asp Lys Ser Lys Gly Ser
545                 550                 555                 560

Tyr Arg Gln His Phe Phe Lys His Gly Gly Thr Ala Glu Leu Lys Cys
```

```
                565                 570                 575

Ser Gln Lys Ser Asn Leu Ala Arg Val Phe Trp Lys Phe Gln Asn Gly
            580                 585                 590

Val Leu Lys Ala Glu Ser Pro Lys Tyr Gly Leu Met Gly Arg Lys Asn
        595                 600                 605

Leu Leu Ile Phe Asn Leu Ser Glu Gly Asp Ser Gly Val Tyr Gln Cys
    610                 615                 620

Leu Ser Glu Glu Arg Val Lys Asn Lys Thr Val Phe Gln Val Val Ala
625                 630                 635                 640

Lys His Val Leu Glu Val Lys Val Val Pro Lys Pro Val Ala Pro
                645                 650                 655

Thr Leu Ser Val Val Gln Thr Glu Gly Ser Arg Ile Ala Thr Lys Val
            660                 665                 670

Leu Val Ala Ser Thr Gln Gly Ser Pro Pro Thr Pro Ala Val Gln
        675                 680                 685

Ala Thr Ser Ser Gly Ala Ile Thr Leu Pro Pro Lys Pro Ala Pro Thr
    690                 695                 700

Gly Thr Ser Cys Glu Pro Lys Ile Val Ile Asn Thr Val Pro Gln Leu
705                 710                 715                 720

His Ser Glu Lys Thr Met Tyr Leu Lys Ser Ser Asp Asn Arg Leu Leu
                725                 730                 735

Met Ser Leu Phe Leu Phe Phe Val Leu Phe Leu Cys Leu Phe Phe
            740                 745                 750

Tyr Asn Cys Tyr Lys Gly Tyr Leu Pro Arg Gln Cys Leu Lys Phe Arg
        755                 760                 765

Ser Ala Leu Leu Ile Gly Lys Lys Pro Lys Ser Asp Phe Cys Asp
    770                 775                 780

Arg Glu Gln Ser Leu Lys Glu Thr Leu Val Glu Pro Gly Ser Phe Ser
785                 790                 795                 800

Gln Gln Asn Gly Glu His Pro Lys Pro Ala Leu Asp Thr Gly Tyr Glu
                805                 810                 815

Thr Glu Gln Asp Thr Ile Thr Ser Lys Val Pro Thr Asp Arg Glu Asp
            820                 825                 830

Ser Gln Arg Ile Asp Asp Leu Ser Ala Arg Asp Lys Pro Phe Asp Val
        835                 840                 845

Lys Cys Glu Leu Lys Phe Ala Asp Ser Asp Ala Asp Gly Asp
    850                 855                 860

<210> SEQ ID NO 3
<211> LENGTH: 655
<212> TYPE: PRT
<213> ORGANISM: Homo sapiens

<400> SEQUENCE: 3

Met Gly Trp Leu Thr Arg Ile Val Cys Leu Phe Trp Gly Val Leu Leu
1               5                   10                  15

Thr Ala Arg Ala Asn Tyr Gln Asn Gly Lys Asn Asn Val Pro Arg Leu
            20                  25                  30

Lys Leu Ser Tyr Lys Glu Met Leu Glu Ser Asn Asn Val Ile Thr Phe
        35                  40                  45

Asn Gly Leu Ala Asn Ser Ser Tyr His Thr Phe Leu Leu Asp Glu
    50                  55                  60

Glu Arg Ser Arg Leu Tyr Val Gly Ala Lys Asp His Ile Phe Ser Phe
65                  70                  75                  80
```

-continued

Asp Leu Val Asn Ile Lys Asp Phe Gln Lys Ile Val Trp Pro Val Ser
             85                  90                  95

Tyr Thr Arg Arg Asp Glu Cys Lys Trp Ala Gly Lys Asp Ile Leu Lys
            100                 105                 110

Glu Cys Ala Asn Phe Ile Lys Val Leu Lys Ala Tyr Asn Gln Thr His
            115                 120                 125

Leu Tyr Ala Cys Gly Thr Gly Ala Phe His Pro Ile Cys Thr Tyr Ile
        130                 135                 140

Glu Ile Gly His His Pro Glu Asp Asn Ile Phe Lys Leu Glu Asn Ser
145                 150                 155                 160

His Phe Glu Asn Gly Arg Gly Lys Ser Pro Tyr Asp Pro Lys Leu Leu
                165                 170                 175

Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
            195                 200                 205

His Pro Ile Arg Thr Glu Gln His Asp Ser Arg Trp Leu Asn Asp Pro
        210                 215                 220

Lys Phe Ile Ser Ala His Leu Ile Ser Glu Ser Asp Asn Pro Glu Asp
225                 230                 235                 240

Asp Lys Val Tyr Phe Phe Phe Arg Glu Asn Ala Ile Asp Gly Glu His
                245                 250                 255

Ser Gly Lys Ala Thr His Ala Arg Ile Gly Gln Ile Cys Lys Asn Asp
            260                 265                 270

Phe Gly Gly His Arg Ser Leu Val Asn Lys Trp Thr Thr Phe Leu Lys
        275                 280                 285

Ala Arg Leu Ile Cys Ser Val Pro Gly Pro Asn Gly Ile Asp Thr His
290                 295                 300

Phe Asp Glu Leu Gln Asp Val Phe Leu Met Asn Phe Lys Asp Pro Lys
305                 310                 315                 320

Asn Pro Val Val Tyr Gly Val Phe Thr Thr Ser Ser Asn Ile Phe Lys
                325                 330                 335

Gly Ser Ala Val Cys Met Tyr Ser Met Ser Asp Val Arg Arg Val Phe
            340                 345                 350

Leu Gly Pro Tyr Ala His Arg Asp Gly Pro Asn Tyr Gln Trp Val Pro
        355                 360                 365

Tyr Gln Gly Arg Val Pro Tyr Pro Arg Pro Gly Thr Cys Pro Ser Lys
370                 375                 380

Thr Phe Gly Gly Phe Asp Ser Thr Lys Asp Leu Pro Asp Asp Val Ile
385                 390                 395                 400

Thr Phe Ala Arg Ser His Pro Ala Met Tyr Asn Pro Val Phe Pro Met
                405                 410                 415

Asn Asn Arg Pro Ile Val Ile Lys Thr Asp Val Asn Tyr Gln Phe Thr
            420                 425                 430

Gln Ile Val Val Asp Arg Val Asp Ala Glu Asp Gly Gln Tyr Asp Val
        435                 440                 445

Met Phe Ile Gly Thr Asp Val Gly Thr Val Leu Lys Val Val Ser Ile
450                 455                 460

Pro Lys Glu Thr Trp Tyr Asp Leu Glu Glu Val Leu Leu Glu Glu Met
465                 470                 475                 480

Thr Val Phe Arg Glu Pro Thr Ala Ile Ser Ala Met Glu Leu Ser Thr
                485                 490                 495

Lys Gln Gln Gln Leu Tyr Ile Gly Ser Thr Ala Gly Val Ala Gln Leu

```
                500             505             510
Pro Leu His Arg Cys Asp Ile Tyr Gly Lys Ala Cys Ala Glu Cys Cys
        515                 520                 525

Leu Ala Arg Asp Pro Tyr Cys Ala Trp Asp Gly Ser Ala Cys Ser Arg
530                 535                 540

Tyr Phe Pro Thr Ala Lys Arg Thr Arg Gln Asp Ile Arg Asn
545                 550                 555                 560

Gly Asp Pro Leu Thr His Cys Ser Asp Leu His Asp Asn His
                565                 570                 575

Gly His Ser Pro Glu Glu Arg Ile Ile Tyr Gly Val Glu Asn Ser Ser
                580                 585                 590

Thr Phe Leu Glu Cys Ser Pro Lys Ser Gln Arg Ala Leu Val Tyr Trp
                595                 600                 605

Gln Phe Gln Arg Arg Asn Glu Glu Arg Lys Glu Glu Ile Arg Val Asp
                610                 615                 620

Asp His Ile Ile Arg Thr Asp Gln Gly Leu Leu Leu Arg Ser Leu Gln
625                 630                 635                 640

Gln Lys Asp Ser Gly Asn Tyr Leu Cys His Ala Val Glu His Gly
                645                 650                 655

<210> SEQ ID NO 4
<211> LENGTH: 607
<212> TYPE: PRT
<213> ORGANISM: Mus musculus

<400> SEQUENCE: 4

Glu Glu Arg Leu Ile Arg Lys Phe Glu Ala Glu Asn Ile Ser Asn Tyr
1               5                   10                  15

Thr Ala Leu Leu Leu Ser Gln Asp Gly Lys Thr Leu Tyr Val Gly Ala
                20                  25                  30

Arg Glu Ala Leu Phe Ala Leu Asn Ser Asn Leu Ser Phe Leu Pro Gly
            35                  40                  45

Gly Glu Tyr Gln Glu Leu Leu Trp Ser Ala Asp Ala Asp Arg Lys Gln
        50                  55                  60

Gln Cys Ser Phe Lys Gly Lys Asp Pro Lys Arg Asp Cys Gln Asn Tyr
65                  70                  75                  80

Ile Lys Ile Leu Leu Pro Leu Asn Ser Ser His Leu Leu Thr Cys Gly
                85                  90                  95

Thr Ala Ala Phe Ser Pro Leu Cys Ala Tyr Ile His Ile Ala Ser Phe
                100                 105                 110

Thr Leu Ala Gln Asp Glu Ala Gly Asn Val Ile Leu Glu Asp Gly Lys
            115                 120                 125

Gly His Cys Pro Phe Asp Pro Asn Phe Lys Ser Thr Ala Leu Val Val
    130                 135                 140

Asp Gly Glu Leu Tyr Thr Gly Thr Val Ser Ser Phe Gln Gly Asn Asp
145                 150                 155                 160

Pro Ala Ile Ser Arg Ser Gln Ser Ser Arg Pro Thr Lys Thr Glu Ser
                165                 170                 175

Ser Leu Asn Trp Leu Gln Asp Pro Ala Phe Val Ala Ser Ala Thr Ser
                180                 185                 190

Pro Glu Ser Leu Gly Ser Pro Ile Gly Asp Asp Lys Ile Tyr Phe
            195                 200                 205

Phe Phe Ser Glu Thr Gly Gln Glu Phe Glu Phe Phe Glu Asn Thr Ile
    210                 215                 220
```

-continued

```
Val Ser Arg Val Ala Arg Val Cys Lys Gly Asp Glu Gly Gly Glu Arg
225                 230                 235                 240

Val Leu Gln Gln Arg Trp Thr Ser Phe Leu Lys Ala Gln Leu Leu Cys
            245                 250                 255

Ser Arg Pro Asp Asp Gly Phe Pro Phe Asn Val Leu Gln Asp Val Phe
        260                 265                 270

Thr Leu Asn Pro Asn Pro Gln Asp Trp Arg Lys Thr Leu Ser Ile Gly
    275                 280                 285

Val Phe Thr Ser Gln Trp His Arg Gly Thr Thr Glu Gly Ser Ala Ile
290                 295                 300

Cys Val Phe Thr Met Asn Asp Val Gln Lys Ala Phe Asp Gly Leu Tyr
305                 310                 315                 320

Lys Lys Val Asn Arg Glu Thr Gln Gln Trp Tyr Thr Glu Thr His Gln
            325                 330                 335

Val Pro Thr Pro Arg Pro Gly Ala Cys Ile Thr Asn Ser Ala Arg Glu
        340                 345                 350

Arg Lys Ile Asn Ser Ser Leu Gln Leu Pro Asp Arg Val Leu Asn Phe
    355                 360                 365

Leu Lys Asp His Phe Leu Met Asp Gly Gln Val Arg Ser Arg Leu Leu
370                 375                 380

Leu Leu Gln Pro Arg Ala Arg Tyr Gln Arg Val Ala Val His Arg Val
385                 390                 395                 400

Pro Gly Leu His Ser Thr Tyr Asp Val Leu Phe Leu Gly Thr Gly Asp
            405                 410                 415

Gly Arg Leu His Lys Ala Val Thr Leu Ser Ser Arg Val His Ile Ile
        420                 425                 430

Glu Glu Leu Gln Ile Phe Pro Gln Gly Gln Pro Val Gln Asn Leu Leu
    435                 440                 445

Leu Asp Ser His Gly Gly Leu Leu Tyr Ala Ser Ser His Ser Gly Val
450                 455                 460

Val Gln Val Pro Val Ala Asn Cys Ser Leu Tyr Pro Thr Cys Gly Asp
465                 470                 475                 480

Cys Leu Leu Ala Arg Asp Pro Tyr Cys Ala Trp Thr Gly Ser Ala Cys
            485                 490                 495

Arg Leu Ala Ser Leu Tyr Gln Pro Asp Leu Ala Ser Arg Pro Trp Thr
        500                 505                 510

Gln Asp Ile Glu Gly Ala Ser Val Lys Glu Leu Cys Lys Asn Ser Ser
    515                 520                 525

Tyr Lys Ala Arg Phe Leu Val Pro Gly Lys Pro Cys Lys Gln Val Gln
530                 535                 540

Ile Gln Pro Asn Thr Val Asn Thr Leu Ala Cys Pro Leu Leu Ser Asn
545                 550                 555                 560

Leu Ala Thr Arg Leu Trp Val His Asn Gly Ala Pro Val Asn Ala Ser
            565                 570                 575

Ala Ser Cys Arg Val Leu Pro Thr Gly Asp Leu Leu Val Gly Ser
        580                 585                 590

Gln Gln Gly Leu Gly Val Phe Gln Cys Trp Ser Ile Glu Glu Gly
    595                 600                 605
```

<210> SEQ ID NO 5
<211> LENGTH: 7
<212> TYPE: PRT
<213> ORGANISM: Artificial Sequence
<220> FEATURE:
<223> OTHER INFORMATION: Oligonucleotide

<400> SEQUENCE: 5

Lys Pro Ala Leu Thr Gly Tyr
1               5

<210> SEQ ID NO 6
<211> LENGTH: 295
<212> TYPE: PRT
<213> ORGANISM: Gallus gallus

<400> SEQUENCE: 6

Asp Asp Lys Ile Tyr Phe Phe Thr Glu Val Ser Val Glu Tyr Glu
1               5                   10                  15

Phe Val Gly Lys Leu Met Ile Pro Arg Ile Ala Arg Val Cys Lys Arg
            20                  25                  30

Asp Gln Gly Gly Leu Arg Thr Leu Gln Lys Lys Trp Thr Ser Phe Leu
        35                  40                  45

Lys Ala Arg Leu Ile Cys Thr Ile Pro Asp Lys Asn Leu Ile Phe Asn
    50                  55                  60

Ile Ile Asn Asp Val Phe Thr Leu Lys Ser Pro Thr Leu Lys Glu Pro
65                  70                  75                  80

Val Ile Tyr Gly Val Phe Thr Pro Gln Leu Asn Asn Val Gly Leu Ser
                85                  90                  95

Ala Val Cys Ala Tyr Asn Leu Ser Ala Val Glu Val Phe Ser Lys
            100                 105                 110

Gly Lys Tyr Met Gln Ser Ala Thr Val Glu Gln Ser His Thr Lys Trp
        115                 120                 125

Val Arg Tyr Asn Gly Glu Ile Pro Asn Pro Arg Pro Gly Ala Cys Ile
    130                 135                 140

Asn Asn Glu Ala Arg Ala Leu Asn Tyr Val Thr Ser Leu Asn Leu Pro
145                 150                 155                 160

Asp Lys Thr Leu Gln Phe Val Lys Asp His Pro Leu Met Asp Asp Ser
                165                 170                 175

Val Thr Pro Val Gly Asp Arg Pro Arg Leu Val Lys Arg Asp Val Lys
            180                 185                 190

Tyr Thr Gln Ile Val Val Asp Arg Val Arg Ala Leu Asn Gly Thr Ile
        195                 200                 205

Tyr Asp Val Met Phe Ile Ser Thr Asp Gln Gly Ala Leu His Lys Ala
    210                 215                 220

Ile Ser Tyr Glu Asn Gly Met His Ile Ile Glu Glu Thr Gln Leu Phe
225                 230                 235                 240

Pro Lys Phe Glu Pro Val Gln Thr Leu Leu Leu Ser Ser Lys Lys Ser
                245                 250                 255

Arg Arg Tyr Leu Tyr Ala Gly Ser Asn Ser Gly Val Val Gln Ser Pro
            260                 265                 270

Val Ala Phe Cys Asp Thr Tyr Thr Thr Cys Phe Asp Cys Val Leu Ala
        275                 280                 285

Arg Asp Pro Tyr Cys Ala Trp
    290                 295

<210> SEQ ID NO 7
<211> LENGTH: 425
<212> TYPE: PRT
<213> ORGANISM: Homo sapiens

<400> SEQUENCE: 7

-continued

```
Gly Glu Leu Tyr Ser Gly Thr Ser Tyr Asn Phe Leu Gly Ser Glu Pro
 1               5                  10                  15

Ile Ile Ser Arg Asn Ser Ser His Ser Pro Leu Arg Thr Glu Tyr Ala
         20                  25                  30

Ile Pro Trp Leu Asn Glu Pro Ser Phe Val Phe Ala Asp Val Ile Arg
             35                  40                  45

Lys Ser Pro Asp Ser Pro Asp Gly Glu Asp Asp Arg Val Tyr Phe Phe
 50                  55                  60

Phe Thr Glu Val Ser Val Glu Tyr Glu Phe Val Phe Arg Val Leu Ile
 65                  70                  75                  80

Pro Arg Ile Ala Arg Val Cys Lys Gly Asp Gln Gly Gly Leu Arg Thr
                 85                  90                  95

Leu Gln Lys Lys Trp Thr Ser Phe Leu Lys Ala Arg Leu Ile Cys Ser
                100                 105                 110

Arg Pro Asp Ser Gly Leu Val Phe Asn Val Leu Arg Asp Val Phe Val
        115                 120                 125

Leu Arg Ser Pro Gly Leu Lys Val Pro Val Phe Tyr Ala Leu Phe Thr
130                 135                 140

Pro Gln Leu Asn Asn Val Gly Leu Ser Ala Val Cys Ala Tyr Asn Leu
145                 150                 155                 160

Ser Thr Ala Glu Glu Val Phe Ser His Gly Lys Tyr Met Gln Ser Thr
                165                 170                 175

Thr Val Glu Gln Ser His Thr Lys Trp Val Arg Tyr Asn Gly Pro Val
            180                 185                 190

Pro Lys Pro Arg Pro Gly Ala Cys Ile Asp Ser Glu Ala Arg Ala Ala
        195                 200                 205

Asn Tyr Thr Ser Ser Leu Asn Leu Pro Asp Lys Thr Leu Gln Phe Val
210                 215                 220

Lys Asp His Pro Leu Met Asp Asp Ser Val Thr Pro Ile Asp Asn Arg
225                 230                 235                 240

Pro Arg Leu Ile Lys Lys Asp Val Asn Tyr Thr Gln Ile Val Val Asp
                245                 250                 255

Arg Thr Gln Ala Leu Asp Gly Thr Val Tyr Asp Val Met Phe Val Ser
            260                 265                 270

Thr Asp Arg Gly Ala Leu His Lys Ala Ile Ser Leu Glu His Ala Val
        275                 280                 285

His Ile Ile Glu Glu Thr Gln Leu Phe Gln Asp Phe Glu Pro Val Gln
290                 295                 300

Thr Leu Leu Leu Ser Ser Lys Lys Gly Asn Arg Phe Val Tyr Ala Gly
305                 310                 315                 320

Ser Asn Ser Gly Val Val Gln Ala Pro Leu Ala Phe Cys Gly Lys His
                325                 330                 335

Gly Thr Cys Glu Asp Cys Val Leu Ala Arg Asp Pro Tyr Cys Ala Trp
            340                 345                 350

Ser Pro Pro Thr Ala Thr Cys Val Ala Leu His Gln Thr Glu Ser Pro
        355                 360                 365

Ser Arg Gly Leu Ile Gln Glu Met Ser Gly Asp Ala Ser Val Cys Pro
370                 375                 380

Asp Lys Ser Lys Gly Ser Tyr Arg Gln His Phe Phe Lys His Gly Gly
385                 390                 395                 400

Thr Ala Glu Leu Lys Cys Ser Gln Lys Ser Asn Leu Ala Arg Val Phe
                405                 410                 415
```

```
Trp Lys Phe Gln Asn Gly Val Leu Lys
            420                 425
```

NUCLEIC ACIDS ENCODING CD100 MOLECULES

GOVERNMENT FUNDING

Work described herein was supported under grants CA40216-11 and AI35225-03 awarded by the National Institutes of Health. The U.S. government therefore may have certain rights in this invention.

BACKGROUND OF THE INVENTION

Induction of a humoral response is important in host defense, for example, in fighting infections by pathogens. A humoral response is mediated by B cells, but requires the help of other cells, such as T cells. Development of a humoral response is a multistage process which occurs primarily in secondary lymphoid tissues.

Resting B cells circulate in the blood, pass through secondary lymphoid tissues, such as lymph nodes, Peyer's patches, spleen and tonsils, where they come into contact with trapped antigens. B cells recognizing a specific antigen through their surface immunoglobulins process the antigen and enter the T cell rich paracortical regions below the outer layer, or cortex, of lymphoid tissues. Some of the T cells in this region have been activated through contact with antigen presenting cells. These T cells in turn promote B cell activation by direct contact with the B cells via interaction of cell surface molecules and by the secretion of T cell-specific cytokines, such as IL-2, IL-4, and IL-5. This cell-cell interaction between T and B cells or production of T cell specific cytokines induces B cells to migrate into B cell follicles. In these follicles, the B cells interact with follicular dendritic cells having antigen-antibody complexes on their surface resulting in the formation of a germinal center. B cells in germinal centers undergo active proliferation, affinity maturation, and differentiation into memory B cells or antibody secreting plasma cells. Thus, whereas antibody-secreting plasma cells produce antibodies to fight infections, memory B cells assure a more rapid response to subsequent exposure to the same antigen.

Some molecules involved in the induction of B-cell proliferation and differentiation have been identified. In addition to cytokines produced in large part by activated T cells, crosslinking of specific B cell surface molecules also provide such signals (Clark E. A. et al, (1994), Nature 367, 425). One such B cell surface molecule is CD40. CD40 is a 45-50 kD protein expressed on activated B cells. Valle et al., (1989), Eur. J. Immunol., 19:1463-1467; Gordon et al., (1988), J. Immunol., 140:1425-1430; Gruber et al., (1989), J. Immunol., 142: 4144-4152. Crosslinking of CD40 with antibodies or with its natural ligand, CD40L, also termed gp39, together with other stimulatory signals induces B cell proliferation and antibody production. Armitage et al., (1992), Nature, 357:80-82; Hollenbaugh et al., (1992), EMBO J., 11:4313-4319.

T cells are not only required for providing help to B cells, but also play a major role in cellular immune responses, such as in delayed type hypersensitivity reactions and in cytotoxicity. To exert their activity, T cells must be activated. To induce antigen-specific T cell activation and clonal expansion, two signals provided by antigen-presenting cells (APCs) must be delivered to the surface of resting T lymphocytes (Jenkins, M. and Schwartz, R. (1987) J. Exp. Med. 165, 302-319; Mueller, D. L., et al. (1990) J. Immunol. 144, 3701-3709; Williams, I. R. and Unanue, E. R. (1990) J. Immunol. 145, 85-93). The first signal, which confers specificity to the immune response, is mediated via the T cell receptor (TCR) following recognition of foreign antigenic peptide presented in the context of the major histocompatibility complex (MHC). The second signal, termed costimulation, induces T cells to proliferate and become functional (Schwartz, R. H. (1990) Science 248, 1349-1356). Costimulation is neither antigen-specific, nor MHC restricted and is thought to be provided by one or more distinct cell surface molecules expressed by APCs (Jenkins, M. K., et al. (1988) J. Immunol. 140, 3324-3330; Linsley, P. S., et al. (1991) J. Exp. Med. 173, 721-730; Gimmi, C. D., et al., (1991) Proc. Natl. Acad. Sci. USA. 88, 6575-6579; Young, J. W., et al. (1992) J. Clin. Invest. 90, 229-237; Koulova, L., et al. (1991) J. Exp. Med. 173, 759-762; Reiser, H., et al. (1992) Proc. Natl. Acad. Sci. USA. 89, 271-275; van-Seventer, G. A., et al. (1990) J. Immunol. 144, 4579-4586; LaSalle, J. M., et al., (1991) J. Immunol. 147, 774-80; Dustin, M. I., et al., (1989) J. Exp. Med. 169, 503; Armitage, R. J., et al. (1992) Nature 357, 80-82; Liu, Y., et al. (1992) J. Exp. Med. 175, 437-445). B7-1 and B7-2 are two such costimulatory molecules which interact with CD28 and CTLA4 on T cells (Linsley, P. S., et al., (1991) J. Exp. Med. 173, 721-730; Gimmi, C. D., et al., (1991) Proc. Natl. Acad. Sci. USA. 88, 6575-6579; Koulova, L., et al., (1991) J. Exp. Med. 173, 759-762; Reiser, H., et al. (1992) Proc. Natl. Acad. Sci. USA. 89, 271-275; Linsley, P. S. et al. (1990) Proc. Natl. Acad. Sci. USA. 87, 5031-5035; Freeman, G. J. et al. (1991) J. Exp. Med. 174, 625-631; Freeman, G. J. et al. (1993) Science 262:909-911; Azuma, M. et al. (1993) Nature 366: 76-79; and Freeman, G. J. et al. (1993) J. Exp. Med. 178: 2185-2192). Though the molecules B7-1 and B7-2 play a critical role in costimulation of T cell, there is some evidence that additional molecules can provide a costimulatory singnal to T cells.

Previous studies demonstrated that several antibodies recognized a 150 kD cell-surface homodimer, termed CD100, that is expressed on a number of hematopoietic cells including B and T lymphocytes, granulocytes, monocytes and natural killer cells but not on eosinophils, platelets, erythrocytes or hematopoietic progenitor cells (Bougeret, C. et al., (1992), J. Immunol. 148, 318; Herold, C., et al., Eds., (Oxford University Press, Oxford, 1995), Leucocyte Typing V., S. F. Schlossman, et al., Eds. vol. 1, pp. 52). These studies indicated that CD100 expression on resting T cells increases on T cells after phytohemagglutinin activation (Bougeret, C. et al., (1992), J. Immunol. 148, 318). In addition, it has been reported that crosslinking of CD100 provides a costimulatory signal to T cells, indicating that this molecule may be involved in T cell activation and clonal expansion (Herold C. et al., (1994), Int. Immunol. 7, 1). However, the role of CD100, in particular its role on B lymphocytes is unknown.

SUMMARY OF THE INVENTION

This invention provides isolated nucleic acid molecules encoding a CD100 antigen. Such nucleic acid molecules (e.g., cDNAs) have a nucleotide sequence encoding a CD100 antigen or biolocially active portions thereof, such as a peptide having a CD100 activity. In a preferred embodiment, the isolated nucleic acid molecule has a nucleotide sequence shown in FIG. 1, SEQ ID NO: 1, or a portion thereof such as the coding region of the nucleotide sequence of FIG. 1, SEQ ID NO: 1. Other preferred nucleic acid molecules encode a protein having the amino acid sequence of FIG. 2, SEQ ID NO: 2. Nucleic acid molecules derived from hematopoietic cells (e.g., a naturally-occurring nucleic acid molecule found in an activated lymphocyte) which hybridize under stringent conditions to the nucleotide sequence shown in FIG. 1, SEQ ID NO: 1 are also within the scope of the invention.

In another embodiment, the isolated nucleic acid molecule is a nucleotide sequence encoding a protein having an amino acid sequence which is at least about 80%, preferably at least about 85%, more preferably at least about 90% and most preferably at least about 95-99% overall amino acid sequence identity with an amino acid sequence shown in FIG. 2, SEQ ID NO: 2. This invention further pertains to nucleic acid molecules which encode a protein which includes a semaphorin domain having an amino acid sequence at least 80%, preferably at least 90%, more preferably at least 95-99% identical to an amino acid sequence shown in FIG. 2, SEQ ID NO: 2. Also within the scope of this invention are nucleic acid molecules which encode a protein which includes an extracellular domain having an amino acid sequence at least 80%, preferably at least 90%, more preferably at least 95-99% identical to an amino acid sequence shown in FIG. 2, SEQ ID NO: 2.

Nucleic acid molecules encoding proteins which include a semaphorin domain having an amino acid sequence at least 60% (preferably at least 70%, 80%, 90%, or 95-99%) identical to an amino acid sequence shown in FIG. 2, SEQ ID NO: 2 and an immunoglobulin-like domain having an amino acid sequence at least 50% (preferably at least 60%, 70%, 80%, 90%, or 95-99%) identical to an amino acid sequence shown in FIG. 2, SEQ ID NO: 2 are also within the scope of this invention. These nucleic acid molecules can encode proteins which optionally include a cytoplasmic domain having an amino acid sequence at least 50% (preferably at least 60%, 70%, 80%, 90%, or 95-99%) identical to an amino acid sequence shown in FIG. 2, SEQ ID NO: 2.

Another aspect of this invention pertains to nucleic acid molecules encoding a CD100 fusion protein which includes a nucleotide sequence encoding a first peptide having an amino acid sequence at least 80% (preferably at least 90%, or 95-99%) identical to an amino acid sequence shown in FIG. 2, SEQ ID NO: 2 and a nucleic sequence encoding a second peptide corresponding to a moiety that facilitates detection or purification of the molecules or that alter the solubility, binding affinity or valency of the first peptide, such as an immunoglobulin constant region.

In another embodiment, the isolated nucleic acid molecule is a nucleotide sequence encoding a peptide fragment of at least about 30 amino acid residues in length, preferably at least about 40 amino acid residues in length, and more preferably at least about 50 amino acid residues in length corresponding to the amino acid sequence shown in FIG. 2, SEQ ID NO: 2. In a preferred embodiment, the peptide fragment has a CD100 activity.

Moreover, given the disclosure herein of a CD100-encoding cDNA sequence (e.g., SEQ ID NO: 1), antisense nucleic acid molecules (i.e, molecules which are complimentary to the coding strand of the CD100 cDNA sequence) are also provided by the invention.

Another aspect of the invention pertains to recombinant expression vectors containing the nucleic acid molecules of the invention and host cells into which such recombinant expression vectors have been introduced. In one embodiment, such a host cell is used to produce CD100 protein by culturing the host cell in a suitable medium. If desired, CD100 protein can be then isolated from the medium or the host cell.

Still another aspect of the invention pertains to isolated CD100 proteins and active fragments thereof, such as peptides having an activity of a CD100 antigen (e.g., at least one biological activity of CD100, such as the ability to stimulate a B cell response, for example, B cell aggregation or the ability to stimulate a T cell response, for example, T cell proliferation). The invention also provides an isolated preparation of a CD100 protein. In preferred embodiments, the CD100 protein comprises an amino acid sequence of FIG. 2, SEQ ID NO: 2, or a mature CD100 protein lacking an amino-terminal signal sequence (e.g., amino acids 22-863 of FIG. 2, SEQ ID NO: 2). In other embodiments, the isolated CD100 protein comprises an amino acid sequence at least 80% identical to an amino acid sequence of FIG. 2, SEQ ID NO: 2 and, preferably has an activity of CD100 (e.g., at least one biological activity of CD100). Preferably, the protein is at least about 90%, more preferably at least about 95%, even more preferably at least about 98% and most preferably at least about 99% identical to the amino acid sequence of FIG. 2, SEQ ID NO: 2.

This invention also pertains to isolated peptides which include a semaphorin domain having an amino acid sequence that is at least 60% (preferably at least 70%, 80%, 90%, or 95-99%) identical to an amino acid sequence shown in FIG. 2 (SEQ ID NO: 2) and an immunoglobulin-like domain having an amino acid sequence that is at least 50% (preferably at least 60%, 70%, 80%, 90%, or 95-99%) identical to an amino acid sequence shown in FIG. 2 (SEQ ID NO: 2). These peptides can optionally include a cytoplasmic domain having an amino acid sequence that is at least 50% identical to an amino acid sequence shown in FIG. 2 (SEQ ID NO: 2).

The invention also provides for a CD100 fusion protein comprising a first peptide having an amino acid sequence at least 80% identical to an amino acid sequence shown in FIG. 2 (SEQ ID NO: 2) and a second peptide corresponding to a moiety that alters the solubility, binding affinity or valency of the first peptide. In preferred embodiments, the fusion protein comprises an extracellular domain of a CD100 antigen. In yet another embodiment, the fusion protein comprises a semaphorin domain of a CD100 antigen.

Peptides comprising a fragment of at least about 30 amino acids, a fragment of at least about 40 amino acids, a fragment of at least about 50 amino acids, or longer fragments of the sequence shown in FIG. 2 (SEQ ID NO: 2) are also within the scope of the invention. The peptide fragments preferably have a CD100 activity.

A CD100 protein of the invention can be incorporated into a pharmaceutical composition which includes the protein (or active portion thereof) and a pharmaceutically acceptable carrier. In addition, vaccine compositions which include at least one antigen and a first agent which stimulates a CD100 ligand-associated signal in a cell, such as a leukocyte, e.g., a B cell or a T cell are also within the scope of this invention. Such vaccine compositions can further include a second agent which stimulates a CD40-associated signal in a cell (e.g., a B cell).

The CD100 protein of the invention and agents which modulate a CD100 ligand-associated signal in a cell, such as a leukocyte can be used to modulate leukocyte responses in vitro or in vivo. In one embodiment, the invention provides a method for stimulating a CD100 ligand-associated signal in a B cell by contacting the cell with an agent that stimulates a CD100 ligand-associated signal. Such an agent can be, for example, a stimulatory form of a CD100 antigen (e.g., a soluble CD100 protein). Additional agents, such as an agent which provides a CD40 associated signal in the B cell can be used to stimulate a B cell response. In another embodiment, a CD100 ligand-associated signal is inhibited to thereby inhibit a response by a B cell. In this embodiment, an agent which interacts with CD100, such as an anti-CD100 antibody can be used to inhibit a response by a B cell such as aggregation or differentiation. The methods of the invention for modulating B cell responses by manipulating the interaction of CD100 with its ligand can be applied in vitro (e.g., with cells in culture) or in vivo, wherein an agent that modulates CD100 and/or CD100 ligand is administered to the subject.

The invention further provides methods for modulating a T cell response comprising contacting a T cell with an agent which modulates a CD100 ligand-associated signal in the T cell. A T cell response is preferably T cell proliferation. The method also preferably includes contacting the T cell with a primary activation agent, such as an antibody to CD3 or at least one antigen.

Additional methods for modulating an interaction between immune cells and nerve cells in a subject by administering an amount of an agent which modulates a CD100 signal in the subject as well as methods for modulating and/or guiding axonal growth by contacting neurons with a modulating form of CD100, such that such that axonal growth is modulated and/or guided are also within the scope of the invention.

BRIEF DESCRIPTION OF THE DRAWINGS

FIG. 1 is the nucleotide sequence of a 4.2 kb cDNA encoding full length human CD100 (SEQ ID NO: 1).

FIG. 2 is the predicted full length amino acid sequence of human CD100 (SEQ ID NO: 2) aligned for comparison to the semaphorin and Ig domains of Human semaphorin III (H-sema III) (SEQ ID NO: 3) and Mouse semaphorin C (M-Sema C) (SEQ ID NO: 4). The regions of identity are boxed. The putative signal sequence is underlined; the sema domain is delimited by *; the gray box indicates the Ig-like domain; the transmembrane region is double-underlined; and the putative tyrosine phosphorylation site KPALTGY (SEQ ID NO: 5) (MAC Pattern: GenBank accession number PS00007) in the cytoplamic tail is boxed.

FIG. 4 represents a sequence comparison between the amino acid sequence of collapsin 4 (top sequence) and the amino acid sequence of a fragment of human CD100 (bottom sequence).

FIG. 9d represents an hematoxylin and eosin stained section of lymphoid tissue showing a germinal center and mantle zone of a secondary lymphoie follicle with adjacent interfollicular T cell zone. All original magnifications: 100×.

FIGS. 10b and e) ; 50% mock transfected and 50% CD40L transfected NIH-3T3 cells (t-mock/t-CD40L) (FIG. 10c), CD100 transfected NIH-3T3 cells (t-CD100) (FIG. 10d); and 50% CD100 transfected and 50% CD40L transfected NIH-3T3 cells (t-CD100/t-CD40L) (FIG. 10f), showing that CD100 stimulates B cell homotypic aggregation and that this effect synergizes with CD40 stimulation.

DETAILED DESCRIPTION OF THE INVENTION

Figure 3:
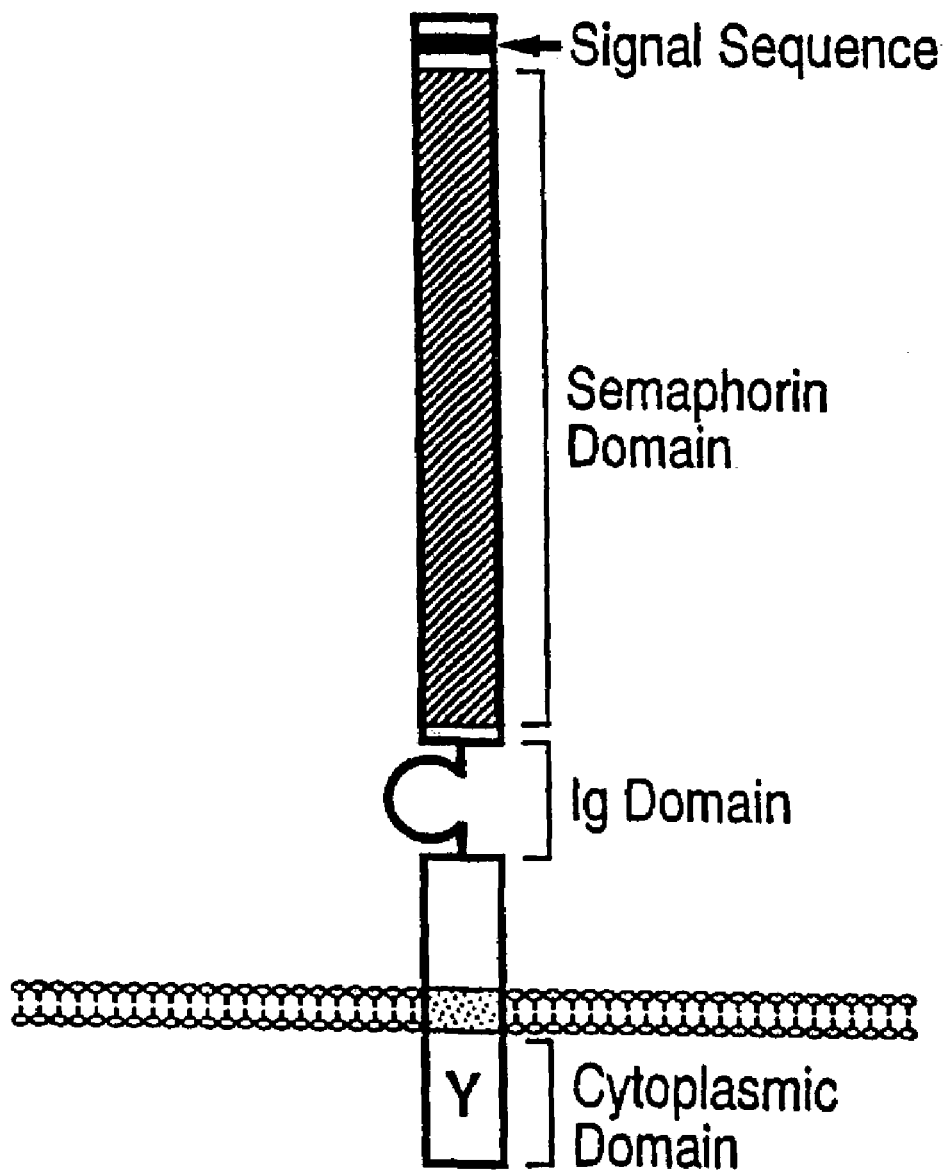
FIG. 3 is a schematic representation of the structure of human CD100 indicating the different domains and the tyrosine phosphorylation site (Y).

The invention pertains to novel CD100 antigens, or active portion thereof which are capable of stimulating a leukocyte response, such as a B cell response. The B cell response can be B cell aggregation. These CD100 antigens are preferably capable of inducing differentiation of B cells and/or are capable of increasing the viability of B cells and, thus, are involved in germinal center development (e.g., affinity maturation of antibodies). Even more preferred CD100 antigens are capable of stimulating a T cell response, such as T cell proliferation. A particularly preferred CD100 antigen is a human CD100 antigen which is expressed on various hematopoietic cells including activated T and B cells. The CD100 antigens of the invention are capable of synergizing with a CD40 ligand (e.g., gp39) to enhance stimulation of homotypic B cell aggregation and cell viability. Thus, the CD100 antigen amplifies a response of B cells to CD40. CD100 also modifies the response of B cells to CD40 by reducing the level of expression of CD23, a cell surface protein which is upregulated in response to stimulation with a CD40 ligand.

The human CD100 protein is a homodimeric transmembrane protein consisting of two polypeptide chains of 150 kDa having an amino acid sequence shown in FIG. 2 (SEQ ID NO: 2). Each polypeptide chain of CD100 consists of a signal sequence of about 13 amino acids (about amino acids 9-21 of the sequence shown in FIG. 2 (SEQ ID NO: 2)) followed by a semaphorin domain of about 512 amino acids (about amino acids 42-553 of the sequence shown in FIG. 2 (SEQ ID NO: 2)), an immunoglobulin-like (Ig-like) domain of about 65 amino acids (about amino acids 566-630 of the sequence shown in FIG. 2 (SEQ ID NO: 2)), a lysine-rich stretch of 104 amino acids, a hydrophobic transmembrane region of about 19 amino acids (about amino acids 735-753 of the sequence shown in FIG. 2 (SEQ ID NO: 2)), and a cytoplasmic tail of 110 amino acids (about amino acids 754-863 of the sequence shown in FIG. 2 (SEQ ID NO: 2)). A consensus site for tyrosine phosphorylation, KPALTGY (SEQ ID NO: 5) at amino acid 813 in the cytoplasmic tail supports the predicted association of CD100 with a tyrosine kinase (Sidorenko S., et al, "Identification of antigens associated with protein kinases by activation antigens panel mAb." S. F. Schlossman, et al., Eds., *Leucocyte Typing V* (Oxford University Press, Oxford, 1995), vol. 1; RuddC., et al., "Identification of antigens associated with protein kinases by activation antigen panel mAb." S. F. Schlossman, et al., Eds., *Leucocyte Typing V* (Oxford University Press, Oxford, 1995), vol. 1.

The semaphorin domain is an extracellular domain of approximately 500 amino acid containing 14-16 cysteines found specifically in proteins belonging to the semaphorin protein family. The phylogenetically conserved semaphorins have been characterized in insect, chicken, mouse and human nervous systems (Kolodkin A. L., et al., (1992), *Neuron* 9, 831; Luo Y. et al, (1993), *Cell* 75, 217; Kolodkin A. et al, (1993), *Cell* 75, 1389; Puschel, A. W., et al. (1995) *Neuron* 14:941; Messersmith, E. K et al. (1995) *Neuron* 14:949; published PCT patent application number PCT/US94/10151). Proteins having a semaphorin domain have also been found in vaccinia virus, variola virus (Kolodkin A. et al, (1993), *Cell* 75, 1389), and herpes virus (Ensser, A. and Fleckenstein, B. (1995) *J. Gen. Virol.* 76: 1063). However the viral semaphorins are only distantly related to the previously identified mammalian and insect semaphorins.

Accordingly, preferred CD100 antigens within the scope of the invention include a semaphorin domain or active portion thereof. Some members of the Semaphorin family have been shown to function as secreted or transmembrane proteins growth cone guidance molecules which are critical for guiding axonal growth of neurons. Membrane bound semaphorins include the grasshopper G-Sema I (also termed G-Fas IV), the Tribolium T-Sema I and the Drosophila D-Sema I. These proteins have an additional stretch of about 80 amino acids in the extracellular domain, a transmembrane domain, and an 80 to 110 amino acid cytoplasmic domain. Secreted semaphorins include the Drosophila D-Sema II, the chicken Collapsin, the human H-Sema III, and the mouse Sema C proteins. Secreted semaphorins have an additional stretch of about 20 amino acids in the extracellular domain, a single immunoglobulin domain and a 70-120 amino acid C-terminal region.

Human CD100 shares certain structural features with H-Sema III and mouse Sema C (M-Sema C). H-Sema III and M-Sema C molecules contain the highly conserved 500 amino acid (aa) semaphorin (sema) domain followed by a C-2 type immunoglobulin-like (Ig) domain. Human CD100 shares 39% identity with H-sema III in the sema domain and 33% identity in the Ig-like domain, whereas the rest of the protein is strikingly divergent. Human CD100 contains 15 of the 16 conserved sema domain cysteines and 9 putative N-linked glycosylation sites. However, CD100 differs from H-Sema III and M-Sema C in that CD100 is a membrane bound protein, whereas H-Sema III and M-Sema C are secreted proteins. Other semaphorins related to collapsin have been isolated from chicken brains (Luo et al. (1995) *Neuron* 14:1131) and partially characterized. The partial amino acid sequence of one of these proteins, collapsin 4 (SEQ ID NO: 6), shares about 78% amino acid identity with a 295 amino acid long C-terminal portion of the human CD100 sema domain (amino acid residues 228-522 of the sequence shown in FIG. 2 (SEQ ID NO: 2). The sequence comparison is shown in FIG. 4. It is unknown whether collapsin 4 is a secreted protein or a membrane bound protein and whether it contains an Ig-like domain.

The human CD100 antigen is the first membrane bound protein shown to have a semaphorin domain and an Ig-like domain. Furthermore, human CD100 is the only membrane bound semaphorin having a tyrosine phosphorylation site in the cytoplasmic domain.

At least some semaphorins are involved in the nervous system development. Neurons secreting semaphorins such as chicken collapsin or its homolog human Sema III (H-sema III), selectively induce extending axonal growth processes to collapse and/or turn away and, therefore, not establish connections with the secreting neuron (Fan J. et al, (1995), *Neuron* 14, 263). The net effect of this collapse is a chemorepulsion and redirection of the extending processes. In contrast, human CD100 is the only semaphorin identified that functions in the hematopoietic system, in particular in modulating a B cell response.

The structural similarities between CD100 and the semaphorin family of proteins indicate that CD100 plays a role in the nervous system in addition to its role in the immune system. CD100 agents of the invention can also be used for modulating communication or interaction between a neuron and an immune cell, such as a neuron. As such, the CD100 antigens of the invention will be used in modulating nerve cell development and/or modulating the interaction between the immune and nervous system.

Accordingly, this invention pertains to CD100 molecules (e.g., antigens, proteins) and to active portions thereof, such as peptides having an activity of CD100. The phrases "an activity of CD100" or "having a CD100 activity" are used interchangeably herein to refer to molecules such as proteins and peptides which are capable of stimulating a leukocyte response, such as a B cell response, e.g, B cell aggregation, and which preferably include a semaphorin domain or an active portion thereof. The phrase "active portion of a semaphorin domain" refers to those portions of a semaphorin domain that are required to mediate, alone, or in collaboration with other portions of the protein, a CD100 activity. Preferred molecules having a CD100 activity are those which are capable of stimulating B cell differentiation. Other preferred molecules having a CD100 activity are capable of stimulating B cell viability, and/or reducing the expression of CD23. Molecules having a CD100 activity are also intended to include molecules which are capable of stimulating a T cell response, such as stimulating proliferation of T cells in the presence of a primary activation signal and which preferably include a semaphorin domain or active portion thereof. Even more preferred molecules of the invention include CD100 antigens which are capable of stimulating a B cell response and a T cell response. Particularly preferred molecules within the scope of the invention include those which are structurally similar to human CD100, i.e., molecules which preferably comprise in addition to the sema domain, an immunoglobulin-like domain, a transmembrane domain, a cytoplasmic domain having a tyrosine phosphorylation site, or any combination of these domains.

Various aspects of the invention are described in further detail in the following subsections:

I. Isolated Nucleic Acid Molecules

One aspect of this invention pertains to isolated nucleic acid molecules that encode a novel CD100 antigen, such as human CD100, fragments of such nucleic acids, or equivalents thereof. The term "nucleic acid molecule" as used herein is intended to include such fragments or equivalents and refers to DNA molecules (e.g., cDNA or genomic DNA) and RNA molecules (e.g., mRNA). The nucleic acid molecule may be single-stranded or double-stranded, but preferably is double-stranded DNA. An "isolated" nucleic acid molecule is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, may be free of other cellular material.

The term "equivalent" is intended to include nucleotide sequences encoding functionally equivalent CD100 antigens or functionally equivalent peptides having a CD100 activity. Functionally equivalent CD100 antigens or peptides is intended to include antigens which are capable of stimulating a leukocyte response, such as a B cell response, e.g., B cell aggregation and preferably contain a semaphorin domain or an active portion thereof. Functionally equivalent CD100 antigens are also preferably capable of stimulating B cell differentiation, prolonging B cell viability, and/or decreasing CD23 expression. Functionally equivalent CD100 antigens or peptides also include antigens which are capable of providing a costimulatory signal to T cells and preferably contain a semaphorin domain or an active portion thereof. Preferred functionally equivalent CD100 antigens include antigens which are capable of stimulating a B cell response and a T cell response, and which preferably comprise a semaphorin domain or active portion thereof.

Other equivalents of CD100 antigens include structural equivalents. Structural equivalents of a CD100 antigen preferably comprise a semaphorin domain or portion thereof, an Ig-like domain or portion thereof, a transmembrane domain or portion thereof, and/or a cytoplasmic domain or portion thereof. A portion of a CD100 antigen is at least 20 amino acid residues in length, more preferably at least 40 amino acid residues in length, and even more preferably at least 60 amino acid residues in length. Preferred nucleic acids of the invention include nucleic acid molecules comprising a nucleotide sequence provided in FIG. 1 (SEQ ID NO: 1), fragments thereof or equivalents thereof.

In one embodiment, the invention pertains to a nucleic acid molecule which is a naturally occuring form of a nucleic acid molecule encoding a CD100 antigen, such as a CD100 antigen having an amino acid sequence shown in FIG. 2 (SEQ ID NO: 2). Preferably, a naturally occuring form of a nucleic acid encoding CD100 is derived from hematopoietic cells, such as activated lymphocytes. Such naturally occuring equivalents can be obtained, for example, by sceening a cDNA library, prepared with RNA from hematopoietic cells, with a nucleic acid molecule having a sequence shown in FIG. 1 (SEQ ID NO: 1) under high stringency hybridization conditions. Such conditions are further described herein.

Also within the scope of the invention are nucleic acids encoding natural variants and isoforms of CD100 antigens, such as splice forms. Northern blot hybridization of a CD100 cDNA to RNA from lymphocytes and non-hematopoietic tissues indicated the existence of several mRNA hybridizing to CD100 DNA (Example 2). Such natural variants are within the scope of the invention. Furthermore, it is likely that secreted isoforms of CD100 exit, since CD100 is related to proteins from the semaphorin family, which are either secreted or membrane bound proteins. Such naturally secreted forms of CD100 are also within the scope of the invention.

In a preferred embodiment, the nucleic acid molecule encoding a CD100 antigen is a cDNA. Preferably, the nucleic acid molecule is a cDNA molecule consisting of at least a portion of a nucleotide sequence encoding human CD100, as shown in FIG. 1 (SEQ ID NO: 1). A preferred portion of the cDNA molecule of FIG. 1 (SEQ ID NO: 1) includes the coding region of the molecule. Other preferred portions include those which code for domains of CD100, such as the extracellular domain, the semaphorin domain, the immunoglobulin domain, the transmembrane domain, the cytoplasmic domain, or any combination therof.

In another embodiment, the nucleic acid of the invention encodes a CD100 antigen or active fragment thereof having an amino acid sequence shown in FIG. 2 (SEQ ID NO: 2). In yet other embodiment, preferred nucleic acid molecules encode a peptide having an overall amino acid sequence identity of at least about 50%, more preferably at least about 60%, more preferably at least about 70%, more preferably at least about 80%, and most preferably at least about 90% with an amino acid sequence shown in FIG. 2 (SEQ ID NO: 2). Nucleic acids which encode peptides having an overall amino acid sequence identity of at least about 93%, more preferably at least about 95%, and most preferably at least about 98-99% with a sequence set forth in FIG. 2 (SEQ ID NO: 2) are also within the scope of the invention. Homology, also termed herein "identity" refers to sequence similarity between two protein (peptides) or between two nucleic acid molecules. Homology can be determined by comparing a position in each sequence which may be aligned for purposes of comparison. When a position in the compared sequences is occupied by the same nucleotide base or amino acid, then the molecules are homologous, or identical, at that position. A degree (or percentage) of homology between sequences is a function of the number of matching or homologous positions shared by the sequences.

Isolated nucleic acids encoding a peptide having a CD100 activity, as described herein, and having a sequence which differs from nucleotide sequence shown in FIG. 1 (SEQ ID NO: 1) due to degeneracy in the genetic code are also within the scope of the invention. Such nucleic acids encode functionally equivalent peptides (e.g., having a CD100 activity) or structurally equivalent peptides but differ in sequence from the sequence of FIG. 2 (SEQ ID NO: 2) due to degeneracy in the genetic code. For example, a number of amino acids are designated by more than one triplet. Codons that specify the same amino acid, or synonyms (for example, CAU and CAC are synonyms for histidine) may occur due to degeneracy in the genetic code. As one example, DNA sequence polymorphisms within the nucleotide sequence of a CD100 antigen (especially those within the third base of a codon) may result in "silent" mutations in the DNA which do not affect the amino acid encoded. However, it is expected that DNA sequence polymorphisms that do lead to changes in the amino acid sequences of the CD100 antigen will exist within a population. It will be appreciated by one skilled in the art that these variations in one or more nucleotides (up to about 3-4% of the nucleotides) of the nucleic acids encoding peptides having the activity of a CD100 antigen may exist among individuals within a population due to natural allelic variation. Any and all such nucleotide variations and resulting amino acid polymorphisms are within the scope of the invention. Furthermore, there may be one or more isoforms or related, cross-reacting family members of the CD100 antigen described herein. Such isoforms or family members are defined as proteins related in function and amino acid sequence to a CD100 antigen, but encoded by genes at different loci. Such isoforms or family members are within the scope of the invention.

A "fragment" of a nucleic acid encoding a CD100 antigen is defined as a nucleotide sequence having fewer nucleotides than the nucleotide sequence encoding the entire amino acid sequence of a CD100 antigen, such as human CD100. A fragment of a nucleic acid is at least about 20 nucleotides, preferably at least about 30 nucleotides, more preferably at least about 40 nucleotides, even more preferably at least about 50 nucleotides long. Also within the scope of the invention are nucleic acid fragments which are at least about 60, 70, 80, 90, 100 or more nucleotides long. Preferred fragments include fragments which encode a peptide having a CD100 activity (i.e., the ability to stimulate a leukocyte response, such as a B cell response, e.g., B cell aggregation, or a T cell response, e.g., T cell proliferation in the presence of a primary activation signal and which preferably contain a sema domain or an active portion thereof). Thus, a preferred peptide having a CD100 activity has a sema domain or active portion thereof, and stimulates aggregation of B cells. Another preferred peptide having CD100 activity has a sema domain or active portion thereof and provides a costimulatory signal to T cells. For determining whether a fragment of a CD100 antigen, such as a fragment of human CD100 is capable of inducing a B cell response, such as B cell aggregation, the peptide, either in soluble form of membrane bound is added to a culture of B cells. Aggregation of B cells can then be visualized macroscopically or under a microscope. Preferred conditions for a B cell aggregation assay are described in the Example section. Assays for determining whether a fragment of a CD100 antigen is capable of providing a costimulatory signal to T cells the following assay can be performed. T cells, such as CD4+ T cells, are incubated in the presence of a primary activation signal, such as an anti-CD3 antibody and various amounts of a CD100 fragment, e.g., expressed on the surface of cells. Following incubation for about 3 days, a proliferation assay is performed, which is indicative of the proliferation rate of the T cells. Thus, a fragment of a CD100 antigen which is capable of costimulating T cells is a fragment of a CD100 antigen which in the presence of a primary T cell activation signal stimulates the T cells to proliferate at a rate that is greater than proliferation rate of T cells contacted only with a primary activation signal. Proliferation assays can also be performed as described in the PCT Application No. PCT/US94/08423.

The fragments of a CD100 antigen, such as human CD100, are also preferably capable of stimulating B cell differentiation. For example, a CD100 fragment of the invention can stimulate the differentiation of B cells from a lymphoblast to a centrocyte. Other CD100 fragments of the invention stimulate the differentiation of B cells into antibody secreting plasma cells or memory B cells. It is also possible that the same fragment will stimulate differentiation of B cells into either memory B cells or antibody secreting B cells depending on the conditions of stimulation. Increased B cell differentiation can be shown, for example, by comparing the expression of B cell markers on B cells incubated in the presence or absence of the CD100 protein fragments. B cells at specific stages of differentiation are characterized by the expression of specific membrane proteins. For example, CD23, CD38, and CD40 are expressed on activated B cells. However, centrocytes and plasma cells lose membrane expression of CD23, CD38 and immunoglobulin molecules, such as IgM and IgD. A plasma cell can also be identified by its secretion of antiboby. Thus, the ability of a peptide of the invention to induce B cell differentiation can be shown by measuring surface levels of specific B cell markers. Preferred fragments of the invention are capable of reducing the level of expression of CD23 induced by CD40 crosslinking. This can be demonstrated, for example, by CD23 fluorescence staining and flow cytometry analysis of B cells stimulated through CD40 and incubated in the presence or absence of CD100 fragments. Methods that can be used for showing the biological activities of CD100 on B cells are further described in the Example section.

Other preferred nucleic acid fragments encode peptides comprising at least part of one or more specific domains of a CD100 antigen. Preferred nucleic acid fragments encode peptides of at least about 20 amino acid residues in length, preferably at least about 40 amino acid residues and length, and more preferably at least about 60 amino acid residues in length. Nucleic acid fragments which encode peptides of at least about 80 amino acid residues in length, at least about 100 amino acid residues in length, at least about 200 amino acid residues in length, at least about 300 amino acid residues in length, at least about 400 amino acid residues in length, at least about 500 amino acid residues in length, or more amino acids in length are also within the scope of the invention. Particularly preferred nucleic acid fragments encode a peptide having an amino acid sequence represented by a formula:

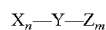
$$X_n\text{—}Y\text{—}Z_m$$

In the formula, Y comprises the semaphorin domain. Y is preferably a peptide having about amino acid residues 42-553 of the sequence shown in FIG. 2 (SEQ ID NO: 2). $X_n$ and $Z_m$ are additional amino acid residue(s) linked to Y by an amide bond. $X_n$ and $Z_m$ are selected from amino acid residues contiguous to Y in the amino acid sequence shown in FIG. 4 (SEQ ID NO: 2). In the formula, $X_n$ is amino acid residue(s) selected from amino acids contiguous to the amino terminus of Y in the sequence shown in FIG. 2 (SEQ ID NO: 2), i.e., from amino acid residue 41 to 1. $Z_m$ is amino acid residue(s) selected from amino acids contiguous to the carboxy terminus of Y in the sequence shown in FIG. 2 (SEQ ID NO: 2), i.e., from amino acid residue 554 to 863. In addition, in the formula, n is a number from 0 to 41 (n=0-42) and m is a number from 0 to 310 (m=0-310). A particularly preferred peptide has an amino acid sequence represented by the formula $X_n$—Y—$Z_m$ as above, where n=0 and m=0.

Particularly preferred nucleic acid fragments encode a peptide having an amino acid sequence represented by a formula $X_n$—Y—$Z_m$, wherein Y is selected from the group consisting of: an extracellular domain, which is preferably about amino acid residues 22-630 of the sequence shown in FIG. 2 (SEQ ID NO: 2); an extracellular domain comprising the signal peptide, which is preferably about amino acid residues 1-630 of the sequence shown in FIG. 2 (SEQ ID NO: 2); an Ig-like domain, which is preferably about amino acid residues 566-630 of the sequence shown in FIG. 2 (SEQ ID NO: 2); a transmembrane domain, which is about amino acid residues 735-753 of the sequence shown in FIG. 2 (SEQ ID NO: 2); and a cytoplasmic domain, which is about amino acid residues 754-863 of the sequence shown in FIG. 2 (SEQ ID NO: 2). In the formula, $X_n$ and $Z_m$ are additional amino acid residues linked to Y by an amide bond. $X_n$ and $Z_m$ are amino acid residues selected from amino acids contiguous to Y in the amino acid sequence shown in FIG. 2 (SEQ ID NO: 2). $X_n$ is amino acid residues selected from amino acids contiguous to the amino terminus of Y in the sequence shown in FIG. 2 (SEQ ID NO: 2). $Z_m$ is amino acid residues selected from amino acids contiguous to the carboxy terminus of Y in the sequence shown in FIG. 2 (SEQ ID NO: 2). According to the formula, n is a number from 0 to 753 (n=0-753) and m is a number from 0 to 234 (m=0-234). A particularly preferred peptide has an amino acid sequence represented by the formula $X_n$—Y—$Z_m$, where n=0 and m=0.

Nucleic acids of the invention also include nucleic acids encoding peptides having a formula $X_n$—Y—$Z_m$, wherein Y is a portion of any of the domains described above and $X_n$ and $Z_m$ are amino acids flanking Y.

Other nucleic acids within the scope of the invention include nucleic acids encoding a peptide having the formula $X_n$—Y—$Z_m$, wherein Y comprises an amino acid sequence that is at least about 50%, preferably at least about 60%, more preferably at least about 70%, more preferably at least about 80%, more preferably at least about 90%, and most preferably at least about 95% identical in amino acid sequence with an amino acid sequence of the semaphorin domain, the extracellular domain, the Ig-like domain, or the cytoplasmic domain shown in FIG. 2 (SEQ ID NO: 2). In yet other embodiment, the amino acid sequence represented by $X_n$ and $Z_m$ are at least about 50%, preferably at least about 60%, more preferably at least about 70%, more preferably at least about 80%, more preferably at least about 90%, and most preferably at least about 95% identical in amino acid sequence with an amino acid sequence shown in FIG. 2, SEQ ID NO: 2.

Yet other preferred nucleic acids of the invention comprise several nucleic acids defined above. Thus, within the scope of the invention are nucleic acids encoding a peptide having a formula $X_n$—Y—$Z_m$, wherein Y comprises a semaphorin domain and a peptide having the same formula, wherein Y comprises an Ig-like domain. Further within the scope of the invention are nucleic acids encoding a peptide having a formula $X_n$—Y—$Z_m$, wherein Y comprises a semaphorin domain and a peptide having the same formula, wherein Y comprises a transmembrane domain.

The invention also pertains to nucleic acid molecules comprising a nucleic acid encoding a semaphorin domain, or an active portion thereof, that is at least about 60%, preferably at least about 80%, more preferably at least about 85%, more preferably at least about 90%, even more preferably at least about 95%, and most preferably at least about 98% identical in amino acid sequence with the semaphorin domain of human CD100 shown in FIG. 2 (SEQ ID NO: 2). Also within the scope of the invention are nucleic acids comprising a first nucleic acid encoding a semaphorin domain, or an active portion thereof, which is at least about 50%, preferably at least about 60%, more preferably at least about 70%, even more preferably at least about 80%, and even more preferably at least about 90% identical in amino acid residues to the semaphorin domain of the human CD100 shown in FIG. 2 (SEQ ID NO: 2) and a second nucleic acid encoding an Ig-like domain, which is at least about 40%, preferably at least about 50%, more preferably at least about 60%, more preferably at least about 70%, more preferably at least about 80%, and most preferably at least about 90% identical in amino acid sequence with the Ig-like domain of the human CD100 shown in FIG. 2 (SEQ ID NO: 2). Even more preferred nucleic acids comprise a third nucleic acid encoding a cytoplasmic domain, which is at least about 40%, preferably at least about 50%, more preferably at least about 60%, more preferably at least about 70%, more preferably at least about 80%, and most preferably at least about 90% identical in amino acid sequence with a cytoplasmic domain of the human CD100 shown in FIG. 2 (SEQ ID NO: 2).

Nucleic acid fragments within the scope of the invention include those capable of hybridizing with nucleic acids from other animal species for use in screening protocols to detect novel proteins that are related to the CD100 antigen described herein. These and other fragments are described in detail herein. Generally, the nucleic acid encoding a fragment of a CD100 antigen will be selected from the bases coding for the mature protein, however, in some instances it may be desirable to select all or part of a fragment or fragments from the leader or signal sequence or non-coding portion of a nucleotide sequence. Preferred nucleic acid fragments for detecting and/or isolating nucleic acids encoding a CD100 antigen comprise any portion of the coding sequence of CD100 excluding the semaphorin domain. In other embodiments, it may be desirable to select a nucleic acid encoding the semaphorin domain. Nucleic acids within the scope of the invention may also contain linker sequences, modified restriction endonuclease sites and other sequences useful for molecular cloning, expression or purification of recombinant protein or fragments thereof. These and other modifications of nucleic acid sequences are described in further detail herein.

A nucleic acid encoding a peptide having an activity of a CD100 activity, such as human CD100, can be obtained from mRNA present in activated B lymphocytes or activated T lymphocytes. Alternatively, a nucleic acid encoding a peptide having an activity of a CD100 antigen can be obtained from other cells and tissues, since CD100 mRNA was also observed in tissues such as skeletal muscle (Example2). It should also be possible to obtain nucleic acid sequences encoding such CD100 antigens from genomic DNA. For example, the gene encoding the CD100 antigen can be cloned from either a cDNA or a genomic library in accordance with protocols herein described. A cDNA encoding a CD100 antigen can be obtained by isolating total mRNA from an appropriate cell line. Double stranded cDNAs can then be prepared from the total mRNA. Subsequently, the cDNAs can be inserted into a suitable plasmid or viral (e.g., bacteriophage) vector using any one of a number of known techniques. Genes encoding CD100 antigens can also be cloned using established polymerase chain reaction techniques in accordance with the nucleotide sequence information provided by the invention. The nucleic acids of the invention can be DNA or RNA. A preferred nucleic acid is a cDNA encoding the human CD100 antigen having the sequence depicted in FIG. 1 (SEQ ID NO: 1).

Another aspect of the invention provides a nucleic acid which hybridizes under high or low stringency conditions to a nucleic acid which encodes a peptide having all or a portion of an amino acid sequence shown in FIG. 2 (SEQ ID NO: 2). Appropriate stringency conditions which promote DNA hybridization, for example, 6.0× sodium chloride/sodium citrate (SSC) at about 45° C., followed by a wash of 2.0×SSC at 50° C. are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 25° C. to a high stringency of about 0.2× SSC at 65° C. In addition, the temperature in the wash step can be increased from low stringency conditions at room temperature, about 22° C., to high stringency conditions, at about 65° C. Preferably, an isolated nucleic acid molecule of the invention that hybridizes under stringent conditions to the sequence of FIG. 1, SEQ ID NO: 1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural CD100.

In addition to naturally-occurring allelic variants of the CD100 sequence that may exist in the population, the skilled artisan will further appreciate that changes may be introduced by mutation into the nucleotide sequence of FIG. 1, SEQ ID NO: 1, thereby leading to changes in the amino acid sequence of the encoded CD100 protein, without altering the functional ability of the CD100 protein. For example, nucleotide substitutions leading to amino acid substitutions at "non-essential" amino acid residues may be made in the sequence of FIG. 1, SEQ ID NO: 1. A "non-essential" amino acid residue is a residue that can be altered from the wild-type sequence of CD100 (e.g., the sequence of FIG. 2, SEQ ID NO: 2) without altering the ability of CD100 to stimulate a leukocyte response, such as a B cell response, i.e., B cell aggregation, whereas an "essential" amino acid residue is required for such activity. For example, amino acid residues of CD100 that are strongly conserved within members of a semaphorin family are predicted to be essential to CD100 activity and thus are not likely to be amenable to alteration.

An isolated nucleic acid molecule encoding a CD100 protein homologous to the protein of FIG. 2, SEQ ID NO: 2 can be created by introducing one or more nucleotide substitutions, additions or deletions into the nucleotide sequence of FIG. 1, SEQ ID NO: 1 such that one or more amino acid substitutions, additions or deletions are introduced into the encoded protein. Mutations can be introduced into FIG. 1, SEQ ID NO: 1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in CD100 is preferably replaced with another amino acid residue from the same side chain family. Alternatively, in another embodiment, mutations can be introduced randomly along all or part of a CD100 coding sequence, such as by saturation mutagenesis, and the resultant mutants can be screened for proteolytic activity to identify mutants that retain proteolytic activity. Following mutagenesis of FIG. 1, SEQ ID NO: 1, the encoded protein can be expressed recombinantly and activity of the protein can be determined. A suitable assays for testing the activity of a CD100 protein or active portion thereof and mutated CD100 proteins is described in further detail herein.

In addition to the nucleic acid molecules encoding CD100 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire CD100 coding strand, or to only a portion thereof. In one embodiment, an antisense nucleic acid molecule is antisense to a "coding region" of the coding strand of a nucleotide sequence encoding CD100. The term "coding region" refers to the region of the nucleotide sequence comprising codons which are translated into amino acid residues (e.g., the entire coding region of FIG. 1, SEQ ID NO: 1). In another embodiment, the antisense nucleic acid molecule is antisense to a "noncoding region" of the coding strand of a nucleotide sequence encoding CD100. The term "noncoding region" refers to 5' and 3' sequences which flank the coding region that are not translated into amino acids (i.e., also referred to as 5' and 3' untranslated regions).

Given the coding strand sequences encoding CD100 disclosed herein (e.g., FIG. 1, SEQ ID NO: 1), antisense nucleic acids of the invention can be designed according to the rules of Watson and Crick base pairing. The antisense nucleic acid molecule may be complementary to the entire coding region of CD100 mRNA, but more preferably is an oligonucleotide which is antisense to only a portion of the coding or noncoding region of CD100 mRNA. For example, the antisense oligonucleotide may be complementary to the region surrounding the translation start site of CD100 mRNA. An antisense oligonucleotide can be, for example, about 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. A ribozyme having specificity for a CD100-encoding nucleic acid can be designed based upon the nucleotide sequence of a CD100 cDNA disclosed herein (i.e., SEQ ID NO: 1). See for example Cech et al. U.S. Pat. No. 4,987,071; and Cech et al. U.S. Pat. No. 5,116,742. Alternatively, CD100 mRNA can be used to select a catalytic RNA having a specific ribonuclease activity from a pool of RNA molecules. See for example Bartel, D. and Szostak, J. W. (1993) *Science* 261: 1411-1418.

The nucleic acid sequences of the invention can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

II. Recombinant Expression Vectors and Host Cells

Another aspect of the invention pertains to vectors, preferably expression vectors, containing a nucleic acid encoding CD100 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are are referred to herein as "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., CD100 proteins, mutant forms of CD100, fusion proteins, etc.).

The recombinant expression vectors of the invention can be designed for expression of CD100 in prokaryotic or eukaryotic cells. For example, CD100 can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector may be transcribed and translated in vitro, for example using T7 promoter regulatory sequences and T7 polymerase.

Expression of proteins in prokaryotes is most often carried out in *E. coli* with vectors containing constitutive or inducible promotors directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn 10-lac fusion promoter mediated by a coexpressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nuc. Acids Res.* 20:2111-2118). Such alteration of nucleic acid sequences of the invention can be carried out by standard DNA synthesis techniques.

In another embodiment, the CD100 expression vector is a yeast expression vector. Examples of vectors for expression in yeast *S. cerivisae* include pYepSec1 (Baldari. et al., (1987) *Embo J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.).

Alternatively, CD100 can be expressed in insect cells using baculovirus expression vectors. Baculovirus vectors available for expression of proteins in cultured insect cells (e.g., Sf 9 cells) include the pAc series (Smith et al., (1983) *Mol. Cell Biol.* 3:2156-2165) and the pVL series (Lucklow, V. A., and Summers, M. D., (1989) *Virology* 170:31-39).

In yet another embodiment, a nucleic acid of the invention is expressed in mammalian cells using a mammalian expression vector. Examples of mammalian expression vectors include pCDM8 (Seed, B., (1987) *Nature* 329:840) and pMT2PC (Kaufman et al. (1987), *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264, 166). Developmentally-regulated promoters are also encompassed, for example the murine hox promoters (Kessel and Gruss (1990) *Science* 249:374-379) and the a-fetoprotein promoter (Campes and Tilghman (1989) *Genes Dev.* 3:537-546).

In one embodiment, a recombinant expression vector containing DNA encoding a CD100 fusion protein is produced. A CD100 fusion protein can be produced by recombinant expression of a nucleotide sequence encoding a first peptide having a CD100 activity and a nucleotide sequence encoding a second peptide corresponding to a moiety that alters a characterisic of the first peptide, e.g., its solubility, affinity, stability or valency, for example, an immunoglobulin constant region. Preferably, the first peptide consists of a portion of the extracellular domain of a CD100 antigen, such as the human CD100 antigen (e.g., approximately amino acid residues 22-734 of the sequence shown in FIG. 2 (SEQ ID NO: 2)) or a semaphorin domain of a CD100 antigen, such as human CD100 (e.g., approximately amino acid residues 42-553 of the sequence shown in FIG. 2 (SEQ ID NO: 2)). Preferred nucleic acids encoding a CD100 Ig fusion protein comprise a nucleic acid encoding a peptide from the group of peptides having about amino acid residues 1-553, about amino acid residues 22-553, about amino acid residues 1-630, and about amino acid residues 22-630 of human CD100 shown in FIG. 2 (SEQ ID NO: 2). The second peptide can include an immunoglobulin constant region, for example, a human C1 domain or C4 domain (e.g., the hinge, CH2 and CH3 regions of human IgC1, or human IgC4, see e.g., Capon et al. U.S. Pat. No. 5,116,964, incorporated herein by reference). The immunoglobulin constant region may contain genetic modifications which reduce or eliminate effector activity inherent in the immunoglobulin structure. For example, DNA encoding the extracellular portion of human CD100 can be joined to DNA encoding the hinge, CH2 and CH3 regions of human IgC1 and/or IgC4 modified by site directed mutagenesis. A resulting CD100 Ig fusion protein may have altered CD100 solubility, binding affinity, stability and/or valency (i.e., the number of binding sites available per molecule) and may increase the efficiency of protein purification. Fusion proteins and peptides produced by recombinant techniques may be secreted and isolated from a mixture of cells and medium containing the protein or peptide. Alternatively, the protein or peptide may be retained cytoplasmically and the cells harvested, lysed and the protein isolated. A cell culture typically includes host cells, media and other byproducts. Suitable mediums for cell culture are well known in the art. Protein and peptides can be isolated from cell culture medium, host cells, or both using techniques known in the art for purifying proteins and peptides. Techniques for transfecting host cells and purifying proteins and peptides are described in further detail herein.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to CD100 RNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to recombinant host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell may be any prokaryotic or eukaryotic cell. For example, CD100 protein may be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual*, 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on the same vector as that encoding CD100 or may be introduced on a separate vector. Cells stably transfected with the introduced nucleic acid can be identified by drug selection (e.g., cells that have incorporated the selectable marker gene will survive, while the other cells die).

Transfected cells which express peptides having a CD100 activity on the surface of the cell are also within the scope of this invention. In one embodiment, a host cell such as a COS cell is transfected with an expression vector directing the expression of a peptide having a CD100 activity on the surface of the cell. Such a transfected host cell can be used in methods for identifying molecules which inhibit binding of CD100 to its receptor or ligand on, e.g., B cells or which interfere with intracellular signaling in response to CD100 interaction. Such cells can also be used for stimulating B cell aggregation and/or B cell differentiation and/or T cell proliferation according to the methods of the invention. In another embodiment, a tumor cell such as a sarcoma, a melanoma, a leukemia, a lymphoma, a carcinoma or a neuroblastoma is transfected with an expression vector directing the expression of at least one peptide having a CD100 activity on the surface of the tumor cell. In some instances, it may be beneficial to transfect a tumor cell to coexpress other molecules, including a CD40 ligand, major histocompatibility complex (MHC) proteins, for example MHC class II and chain proteins or an MHC class I chain protein, and, if necessary, a $\beta_2$ microglobulin protein. Such transfected tumor cells can be used to induce tumor immunity in a subject.

A host cell of the invention, such as a prokaryotic or eukaryotic host cell in culture, can be used to produce (i.e., express) CD100 protein. Accordingly, the invention further provides methods for producing CD100 protein using the host cells of the invention. In one embodiment, the method comprises culturing the host cell of invention (into which a recombinant expression vector encoding CD100 has been introduced) in a suitable medium until CD100 is produced. In another embodiment, the method further comprises isolating CD100 from the medium or the host cell.

The host cells of the invention can also be used to produce nonhuman transgenic animals. For example, in one embodiment, a host cell of the invention is a fertilized oocyte or an embryonic stem cell into which CD100-coding sequences have been introduced. Such host cells can then be used to create non-human transgenic animals in which exogenous CD100 sequences have been introduced into their genome or homologous recombinant animals in which endogenous CD100 sequences have been altered. Such animals are useful for studying the function and/or activity of CD100 and for identifying and/or evaluating modulators of CD100 activity. As used herein, a "transgenic animal" is a non-human animal, preferably a mammal, more preferably a mouse, in which one or more of the cells of the animal includes a transgene. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous CD100 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing CD100-encoding nucleic acid into the male pronuclei of a fertilized oocyte, e.g., by microinjection, and allowing the oocyte to develop in a pseudopregnant female foster animal. The human CD100 cDNA sequence of FIG. 1, SEQ ID NO: 1 can be introduced as a transgene into the genome of a non-human animal. Alternatively, a nonhuman homologue of the human CD100 gene, such as a mouse CD100 gene, can be isolated based on hybridization to the human CD100 cDNA (described further in subsection I above) and used as a transgene. Intronic sequences and polyadenylation signals can also be included in the transgene to increase the efficiency of expression of the transgene. A tissue-specific regulatory sequence(s) can be operably linked to the CD100 transgene to direct expression of CD100 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the CD100 transgene in its genome and/or expression of CD100 mRNA in tissues or cells of the animals. A transgenic founder animal can then be used to breed additional animals carrying the transgene. Moreover, transgenic animals carrying a transgene encoding CD100 can further be bred to other transgenic animals carrying other transgenes.

To create a homologous recombinant animal, a vector is prepared which contains at least a portion of a CD100 gene into which a deletion, addition or substitution has been introduced to thereby alter, e.g., functionally disrupt, the CD100 gene. The CD100 gene may be a human gene (e.g., from a human genomic clone isolated from a human genomic library screened with the cDNA of FIG. 1, SEQ ID NO: 1), but more preferably, is a non-human homologue of a human CD100 gene. For example, a mouse CD100 gene can be isolated from a mouse genomic DNA library using the human CD100 cDNA of FIG. 1, SEQ ID NO: 1 as a probe. The mouse CD100 gene then can be used to construct a homologous recombination vector suitable for altering an endogenous CD100 gene in the mouse genome. In a preferred embodiment, the vector is designed such that, upon homologous recombination, the endogenous CD100 gene is functionally disrupted (i.e., no longer encodes a functional protein; also referred to as a "knock out" vector). Alternatively, the vector can be designed such that, upon homologous recombination, the endogenous CD100 gene is mutated or otherwise altered but still encodes functional protein (e.g., the upstream regulatory region can be altered to thereby alter the expression of the endogenous CD100 protein). In the homologous recombination vector, the altered portion of the CD100 gene is flanked at its 5' and 3' ends by additional nucleic acid of the CD100 gene to allow for homologous recombination to occur between the exogenous CD100 gene carried by the vector and an endogenous CD100 gene in an embryonic stem cell. The additional flanking CD100 nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced CD100 gene has homologously recombined with the endogenous CD100 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

III. Isolated CD100 Proteins and Anti-CD100 Antibodies

Another aspect of the invention pertains to isolated CD100 proteins and active fragments thereof, i.e, peptides having a CD100 activity, such as human CD100. This invention also provides a preparation of CD100 or fragment thereof. An "isolated" protein is substantially free of cellular material or culture medium when produced by recombinant DNA techniques, or chemical precursors or other chemicals when chemically synthesized. In a preferred embodiment, the CD100 protein has an amino acid sequence shown in FIG. 2, SEQ ID NO: 2. In other embodiments, the CD100 protein is substantially homologous or similar to FIG. 2, SEQ ID NO: 2 and retains the functional activity of the protein of FIG. 2, SEQ ID NO: 2 yet differs in amino acid sequence due to natural allelic variation or mutagenesis, as described in detail in subsection I above. Accordingly, in another embodiment, the CD100 protein is a protein which comprises an amino acid sequence at least 80% overall amino acid sequence identity with the amino acid sequence of FIG. 2, SEQ ID NO: 2. Preferably, the protein is at least 90% identical to FIG. 2, SEQ ID NO: 2, more preferably at least 95% identical to FIG. 2, SEQ ID NO: 2, even more preferably at least 98-99% identical to FIG. 2, SEQ ID NO: 2.

An isolated CD100 protein may comprise the entire amino acid sequence of FIG. 2, SEQ ID NO: 2 or a biologically active portion thereof. For example, an active portion of CD100 can comprise a mature form of CD100 in which a hydrophobic, amino-terminal signal sequence is absent. Moreover, other biologically active portions, in which other regions of the protein are deleted, can be prepared by recombinant techniques and evaluated for a CD100 activity as described in detail above. For example, a peptide having a CD100 activity may differ in amino acid sequence from the human CD100 depicted in FIG. 2 (SEQ ID NO: 2), but such differences result in a peptide which functions in the same or similar manner as CD100. Thus, peptides having the ability to stimulate a leukocyte response, such as a B cell response, e.g., B cell aggregation, and which preferably has a semaphorin domain or an active portion thereof are within the scope of the invention. Preferred peptides of the invention include those which are further capable of inducing B cell differentiation, stimulating B cell survival, downregulating CD40 induced CD23 expression and/or costimulating T cell proliferation.

One embodiment provides a CD100 derived peptide having B cell binding activity, but lacking the ability to stimulate a leukocyte response, such as a B cell response. Such a peptide can be used to inhibit or block B cell differentiation or T cell proliferation in a subject. Alternatively, a peptide having both B cell binding activity and the ability to deliver a stimulatory signal to B cells can be used to stimulate or enhance a B cell response, such as B cell aggregation and/or antibody production in a subject. Similarly, a peptide having T cell binding activity and the ability to deliver a stimulatory signal to T cells can be used to stimulate or enhance a T cell response, such as T cell proliferation. Various modifications of the CD100 protein to produce these and other functionally equivalent peptides are described in detail herein. The term "peptide" as used herein, refers to peptides, proteins and polypeptides.

A peptide can be produced by modification of the amino acid sequence of the human CD100 protein shown in FIG. 2 (SEQ ID NO: 2), such as a substitution, addition or deletion of an amino acid residue which is not directly involved in the function of CD100.

Peptides of the invention are typically at least 30 amino acid residues in length, preferably at least 40 amino acid residues in length, more preferably at least 50 amino acid residues in length, and most preferably 60 amino acid residues in length. Peptides having CD100 activity and including at least 80 amino acid residues in length, at least 100 amino acid residues in length, at least about 200, at least about 300, at least about 400, or at least about 500 or more amino acid residues in length are also within the scope of the invention. A preferred peptide includes an extracellular domain portion of the human CD100 antigen (e.g., about amino acid residues 22-734 of the sequence shown in FIG. 2 (SEQ ID NO: 2). Other preferred peptides have an amino acid sequence represented by a formula:

$$X_n\text{—}Y\text{—}Z_m$$

where Y is selected from the group consting of: an extracellular domain comprising the signal peptide, which is preferably about amino acid residues 1-630 of the sequence shown in FIG. 2 (SEQ ID NO: 2); a semaphorin domain, which is preferably about amino acid residues 42-553 of the sequence shown in FIG. 2 (SEQ ID NO: 2); an Ig-like domain, which is preferably about amino acid residues 566-630 of the sequence shown in FIG. 2 (SEQ ID NO: 2); a transmembrane domain, which is about amino acid residues 735-753 of the sequence shown in FIG. 2 (SEQ ID NO: 2); and a cytoplasmic domain, which is about amino acid residues 754-863 of the sequence shown in FIG. 2 (SEQ ID NO: 2). In the formula, $X_n$ and $Z_m$ are additional amino acid residues linked to Y by an amide bond. $X_n$ and $Z_m$ are amino acid residues selected from amino acids contiguous to Y in the amino acid sequence shown in FIG. 2 (SEQ ID NO: 2). $X_n$ is amino acid residues selected from amino acids contiguous to the amino terminus of Y in the sequence shown in FIG. 2 (SEQ ID NO: 2). $Z_m$ is amino acid residues selected from amino acids contiguous to the carboxy terminus of Y in the sequence shown in FIG. 2 (SEQ ID NO: 2). According to the formula, n is a number from 0 to 753 (n=0-75). A particularly preferred peptide has an amino acid sequence represented by the formula $X_n$—Y—$Z_m$, where n=0 and m=0.

Other peptides within the scope of the invention include those encoded by the nucleic acids described herein.

Another embodiment of the invention provides a substantially pure preparation of a peptide having a CD100 activity. Such a preparation is substantially free of proteins and peptides with which the peptide naturally occurs in a cell or with which it naturally occurs when secreted by a cell.

The term "isolated" as used throughout this application refers to a nucleic acid, protein or peptide having an activity of a CD100 antigen substantially free of cellular material or culture medium when produced by recombinant DNA techniques, or chemical precursors or other chemicals when chemically synthesized. An isolated nucleic acid is also free of sequences which naturally flank the nucleic acid (i.e., sequences located at the 5' and 3' ends of the nucleic acid) in the organism from which the nucleic acid is derived.

The peptides and fusion proteins produced from the nucleic acid molecules of the present invention can also be used to produce antibodies specifically reactive with CD100 antigens. For example, by using a full-length CD100 antigen, such as an antigen having an amino acid sequence shown in FIG. 2 (SEQ ID NO: 2), or a peptide fragment thereof, anti-protein/anti-peptide polyclonal antisera or monoclonal antibodies can be made using standard methods. A mammal, (e.g., a mouse, hamster, or rabbit) can be immunized with an immunogenic form of the protein or peptide which elicits an antibody response in the mammal. The immunogen can be, for example, a recombinant CD100 protein, or fragment thereof, a synthetic peptide fragment or a cell that expresses a CD100 antigen on its surface. The cell can be for example, a splenic B cell or a cell transfected with a nucleic acid encoding a CD100 antigen of the invention (e.g., a/CD100 cDNA) such that the CD100 antigen is expressed on the cell surface. The immunogen can be modified to increase its immunogenicity. For example, techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay can be used with the immunogen as antigen to assess the levels of antibodies.

Following immunization, antisera can be obtained and, if desired, polyclonal antibodies isolated from the sera. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (*Nature* (1975) 256:495-497) as well as other techniques such as the human B-cell hybridoma technique (Kozbar et al., *Immunol. Today* (1983) 4:72), the EBV-hybridoma technique to produce human monoclonal antibodies (Cole et al. *Monoclonal Antibodies in Cancer Therapy* (1985) Allen R. Bliss, Inc., pages 77-96), and screening of combinatorial antibody libraries (Huse et al., *Science* (1989) 246:1275). Hybridoma cells can be screened immunochemically for production of antibodies specifically reactive with the peptide and monoclonal antibodies isolated.

The term antibody as used herein is intended to include fragments thereof which are also specifically reactive with a peptide having the activity of a novel B lymphocyte antigen or fusion protein as described herein. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-CD100 antigen (i.e., CD100) portion.

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes the gene product of the novel CD100 antigens of the invention. See, for example, Morrison et al., (1985), *Proc. Natl. Acad. Sci. U.S.A.* 81:6851; Takeda et al., (1985), *Nature* 314:452, Cabilly et al., U.S. Pat. No. 4,816, 567; Boss et al., U.S. Pat. No. 4,816,397; Tanaguchi et al., European Patent Publication EP171496; European Patent Publication 0173494, United Kingdom Patent GB 2177096B. It is expected that such chimeric antibodies would be less immunogenic in a human subject than the corresponding non-chimeric antibody.

For human therapeutic purposes, the monoclonal or chimeric antibodies specifically reactive with a CD100 antigen as described herein can be further humanized by producing human variable region chimeras, in which parts of the variable regions, especially the conserved framework regions of the antigen-binding domain, are of human origin and only the hypervariable regions are of non-human origin. General reviews of "humanized" chimeric antibodies are provided by Morrison, S. L. (1985) *Science* 229:1202-1207 and by Oi et al. (1986) *BioTechniques* 4:214. Such altered immunoglobulin molecules may be made by any of several techniques known in the art, (e.g., Teng et al., (1983), *Proc. Natl. Acad. Sci. U.S.A.*, 80:7308-7312; Kozbor et al., (1983), *Immunology Today*, 4:7279; Olsson et al., (1982), *Meth. Enzymol.*, 92:3-16), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain. Suitable "humanized" antibodies can be alternatively produced by CDR or CEA substitution (see U.S. Pat. No. 5,225,539 to Winter; Jones et al. (1986) *Nature* 321:552-525; Verhoeyan et al. (1988) *Science* 239: 1534; and Beidler et al. (1988) *J. Immunol.* 141:4053-4060). Humanized antibodies which have reduced immunogenicity are preferred for immunotherapy in human subjects. Immunotherapy with a humanized antibody will likely reduce the necessity for any concomitant immunosuppression and may result in increased long term effectiveness for the treatment of chronic disease situations or situations requiring repeated antibody treatments.

As an alternative to humanizing a monoclonal antibody from a mouse or other species, a human monoclonal antibody directed against a human protein can be generated. Transgenic mice carrying human antibody repertoires have been created which can be immunized with a CD100 antigen, such as human CD100. Splenocytes from these immunized transgenic mice can then be used to create hybridomas that secrete human monoclonal antibodies specifically reactive with a CD100 antigen (see, e.g., Wood et al. PCT publication WO 91/00906, Kucherlapati et al. PCT publication WO 91/10741; Lonberg et al. PCT publication WO 92/03918; Kay et al. PCT publication 92/03917; Lonberg, N. et al. (1994) *Nature* 368: 856-859; Green, L. L. et al. (1994) *Nature Genet.* 7:13-21; Morrison, S. L. et al. (1994) *Proc. Natl. Acad. Sci. USA* 81:6851-6855; Bruggeman et al. (1993) *Year Immunol* 7:33-40; Tuaillon et al. (1993) *PNAS* 90:3720-3724; and Bruggeman et al. (1991) *Eur J Immunol* 21:1323-1326).

Monoclonal antibody compositions of the invention can also be produced by other methods well known to those skilled in the art of recombinant DNA technology. An alternative method, referred to as the "combinatorial antibody display" method, has been developed to identify and isolate antibody fragments having a particular antigen specificity, and can be utilized to produce Monoclonal antibodies that bind a CD100 antigen of the invention (for descriptions of combinatorial antibody display see e.g., Sastry et al. (1989) *PNAS* 86:5728; Huse et al. (1989) *Science* 246:1275; and Orlandi et al. (1989) *PNAS* 86:3833). After immunizing an animal with a CD100 antigen, the antibody repertoire of the resulting B-cell pool is cloned. Methods are generally known for directly obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al. (1991) *Biotechniques* 11:152-156). A similar strategy can also been used to amplify human heavy and light chain variable regions from human antibodies (Larrick et al. (1991) *Methods: Companion to Methods in Enzymology* 2:106-110).

In an illustrative embodiment, RNA is isolated from activated B cells of, for example, peripheral blood cells, bone marrow, or spleen preparations, using standard protocols (e.g., U.S. Pat. No. 4,683,202; Orlandi, et al. *PNAS* (1989) 86:3833-3837; Sastry et al., *PNAS* (1989) 86:5728-5732; and Huse et al. (1989) *Science* 246:1275-1281.) First-strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combinantion, and ligated into appropriate vectors for further manipulation in generating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large diverse antibody display libraries, rapid sorting after each affinity separation round, and easy isolation of the antibody gene from purified display packages. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating a diverse antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982.

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., *Nature* (1990) 348:552-554, complete $V_H$ and $V_L$ domains of an antibody, joined by a flexible $(Gly_4$-$Ser)_3$ linker can be used to produce a single chain antibody which can render the display package separable based on antigen affinity. Isolated scFV antibodies immunoreactive with a peptide having activity of a CD100 antigen can subsequently be formulated into a pharmaceutical preparation for use in the subject method.

Once displayed on the surface of a display package (e.g., filamentous phage), the antibody library is screened with a CD100 antigen, or peptide fragment thereof, to identify and isolate packages that express an antibody having specificity for the CD100 antigen. Nucleic acid encoding the selected antibody can be recovered from the display package (e.g., from the phage genome) and subcloned into other expression vectors by standard recombinant DNA techniques.

The antibodies of the current invention can be used therapeutically to inhibit a B cell response through blocking receptor:ligand interactions necessary for transduction of a CD100 ligand-associated signal in the B cell. These so-called "blocking antibodies" can be identified by their ability to inhibit a B cell response when added to an in vitro assay as described herein. Antibodies of the invention can also be used to block a T cell response, such as T cell proliferation. Alternatively, the antibodies of the invention can be stimulatory antibodies, and stimulate a B cell and/or a T cell response.

The polyclonal or monoclonal antibodies of the current invention, such as an antibody specifically reactive with a recombinant or synthetic peptide having a CD100 activity can also be used to isolate the native CD100 antigen from cells. For example, antibodies reactive with the peptide can be used to isolate the naturally-occurring or native form of CD100 from activated B lymphocytes by immunoaffinity chromatography. In addition, the native form of cross-reactive CD100-like molecules can be isolated from B cells or other cells by immunoaffinity chromatography with an anti-CD100 antibody.

IV. Uses and Methods of the Invention

The invention further pertains to methods for modulating a leukocyte response in which a leukocyte is contacted in vitro or in vivo with an agent which modulates a CD100 ligand-associated signal. The term "leukocyte" is intended to include any cell of the blood which is not a red blood cell and includes lymphocytes, granulocytes, and monocytes. A preferred leukocyte is a lymphocyte, such as a B cell or a T cell.

The term "B cell" is intended to include a B lymphocyte that is at any state of maturation. Thus, the B cell can be a progenitor cell, a pre-B cell, an immature B cell, a mature B cell, a blast cell, a centroblast, a centrocyte, an activated B cell, a memory B cell, or an antibody secreting plasma cell. A preferred B cell is an activated B cell, i.e, a B cell which has encountered an antigen. The term "B cell response" is intended to include a response of a B cell to a stimulus. The stimulus can be a soluble stimulus such as an antigen, a lymphokine, or a growth factor or a combination thereof. Alternatively, the stimulus can be membrane bound molecule, such as a receptor on T helper (Th) cells, e.g., CD28, CTLA4, gp39, or an adhesion molecule. Since a change in a B cell, such as a change occuring during the process of B cell maturation or activation is mediated by extracellular factors and membrane bound molecules, a response of a B cell is intended to include any change in a B cell, such as a change in stage of differentiation, secretion of factors, e.g., antibodies. Thus, a modulation of a B cell response can be a modulation of B cell aggregation, a modulation of B cell differentiation, such as differentiation into a plasma cell or into a memory B cell, or a modulation of cell viability. In a preferred embodiment, the invention provides a method for stimulating the differentiation of a B cell from a lymphobast to a centrocyte. In another preferred embodiment, the invention provides a method for modulating B cell aggregation, such as homotypic B cell aggregation. In another embodiment, the invention provides a method for modulating B cell survival. In yet another preferred embodiment, the invention provides a method for modulating production of antibodies by B cells. In a further embodiment, the invention provides a method for modulating proliferation of B cells.

In one embodiment, the invention provides a method for stimulating a T cell response. A T cell response is intended to include stimulation of any change in the T cell that results from interaction with a soluble or membrane bound factor. Thus, a T cell response can be T cell proliferation, T cytotoxic activity, secretion of cytokines, differentiation or any T cell effector function.

In a preferred embodiment, the invention provides a method for stimulating T cell proliferation in the presence of a primary activation signal, comprising contacting a T cell with a CD100 antigen or active fragment thereof and a primary activation signal. The T cell can be a CD4+ T cell, a CD8+ T cell, a T helper cell (Th), or a cytotoxic T cell (Tc). Interaction between the T cell receptor (TCR)/CD3 complex and antigen presented in conjunction with either major histocompatibility complex (MHC) class I or class II molecules on an antigen-presenting cell initiates a series of biochemical events termed antigen-specific T cell activation. The term "T cell activation" is used herein to define a state in which a T cell response has been initiated or activated by a primary signal, such as through the TCR/CD3 complex, but not necessarily due to interaction with a protein antigen. A T cell is activated if it has received a primary signaling event which initiates an immune response by the T cell.

T cell activation can be accomplished by stimulating the T cell TCR/CD3 complex or via stimulation of the CD2 surface protein. An anti-CD3 monoclonal antibody can be used to activate a population of T cells via the TCR/CD3 complex. Although a number of anti-human CD3 monoclonal antibodies are commercially available, OKT3 prepared from hybridoma cells obtained from the American Type Culture Collection or monoclonal antibody G19-4 is preferred. Similarly, binding of an anti-CD2 antibody will activate T cells. Stimulatory forms of anti-CD2 antibodies are known and available. Stimulation through CD2 with anti-CD2 antibodies is typically accomplished using a combination of at least two different anti-CD2 antibodies. Stimulatory combinations of anti-CD2 antibodies which have been described include the following: the T11.3 antibody in combination with the T11.1 or T11.2 antibody (Meuer, S. C. et al. (1984) *Cell* 36:897-906) and the 9.6 antibody (which recognizes the same epitope as T11.1) in combination with the 9-1 antibody (Yang, S. Y. et al. (1986) *J. Immunol.* 137:1097-1100). Other antibodies which bind to the same epitopes as any of the above described antibodies can also be used. Additional antibodies, or combinations of antibodies, can be prepared and identified by standard techniques.

A primary activation signal can also be provided by a polyclonal activator. Polyclonal activators include agents that bind to glycoproteins expressed on the plasma membrane of T cells and include lectins, such as phytohemaglutinin (PHA), concanavalin (Con A) and pokeweed mitogen (PWM).

A primary activation signal can also be delivered to a T cell through use of a combination of a protein kinase C (PKC) activator such as a phorbol ester (e.g., phorbol myristate acetate) and a calcium ionophore (e.g., ionomycin which raises cytoplasmic calcium concentrations). The use of these agents bypasses the TCR/CD3 complex but delivers a stimulatory signal to T cells. These agents are also known to exert a synergistic effect on T cells to promote T cell activation and can be used in the absence of antigen to deliver a primary activation signal to T cells.

Accordingly, the invention provides a method for stimulating antigen specific T cell proliferation by contacting a T cell with a stimulatory form of a CD100 antigen and a primary activation signal provided by an antigen presented in the context of a major histocompatibility complex antigen, such as on an antigen presenting cell. The invention further provides a method for stimulating proliferation of T cells in a non antigen specific manner by contacting the T cell with a CD100 antigen and an agent which provides a non antigen specific primary activation signal, such as an anti-CD3 antibody, a polyclonal activator, a combination of a PKC activator and a calcium ionophore, or an agent which stimulates CD2.

The invention provides methods for modulating a leukocyte response. The term "modulating" is intended to include stimulation or inhibition of a leukocyte response. In one embodiment, the invention provides a method for stimulating B cell aggregation. In another embodiment, the invention provides a method for inhibiting B cell aggregation. Also within the scope of the invention are methods for stimulating stimulating T cell proliferation and methods for inhibiting T cell proliferation.

In one embodiment of the invention, a leukocyte response is modulated by contacting leukocytes with an agent which modulates a CD100 ligand-associated signal. The term "CD100 ligand-associated signal" is intended to include an intracellular signal which is induced by contact of the natural form of CD100 with its ligand on an immune cell, such as a leukocyte and which results in the biological effects induced by such a contact, e.g., stimulation of B cell aggregation, stimulation of differentiation, increased cell viability, reduction of CD23 expression, and/or stimulation of T cell proliferation. The CD100 ligand-associated signal can be mediated by one receptor, or by several different receptors. The term "CD100 receptor" is used herein interchangeably with the term "CD100 ligand" and is intended to include a surface molecule or a secreted molecule with which a CD100 antigen interacts. Such an interaction can be a "positive interaction", i.e., resulting in transduction of a CD100 ligand-associated signal and the resulting biological effects. An interaction of a CD100 molecule with one of its receptors or ligands can also be a "negative interaction", such that upon interaction of the receptor with a CD100 molecule, no CD100 ligand-associated signal is transduced. Thus, a CD100 molecule may interact with more than one receptor, and the outcome of the interaction with the different receptors may be different according to the specific receptor. Specific types of leukocytes and other cells may have specific receptors. The outcome of the interaction of CD100 with one of its receptors may depend on the presence of other signals delivered to the leukocyte. One possible receptor for CD100 is CD100 itself, or a molecule having a CD100 activity and/or being structurally related to CD100.

A. Agents which Stimulate a CD100 Ligand-Associated Signal

In one embodiment of the invention, the agent which modulates a CD100 ligand-associated signal is an agent which stimulates a CD100 ligand-associated signal. A CD100 ligand-associated signal can be stimulated in a leukocyte by contact of the leukocyte with a stimulatory form of CD100. Alternatively, a CD100 ligand-associated signal can be stimulated by an agent which is not a form of CD100, but which mimicks the effects of a stimulatory form of CD100 and interacts with the CD100 ligand on the leukocyte. In yet another embodiment, a CD100 ligand-associated signal is stimulated by contacting a leukocyte with an agent which does not interact with CD100, but which mimicks a CD100 ligand-associated signal.

In a preferred embodiment of the invention, the stimulatory agent is a stimulatory form of a CD100 molecule. The term "stimulatory form of a CD100 molecule" is intended to include an agent which is a CD100 antigen, or molecule derived therefrom and which interacts with a leukocyte, such that a CD100 ligand-associated signal is transduced in the leukocyte.

A preferred CD100 stimulatory form of CD100 is a membrane bound form of CD100, or a form of CD100 linked to a solid phase surface. It has been shown (Examples 4 and 5 herein) that contacting a population of B cells with NIH-3T3 cells expressing CD100 results in augmentation of cell clustering and B cell survival. Thus, the invention provides methods for stimulating B cell aggregation, B cell differentiation, and increased B cell survival comprising contacting a population of B cells with cells that express CD100 molecules on their surface. It has further been shown herein that contacting a population of T cells with NIH-3T3 expressing CD100 in the presence of anti-CD3 antibodies results in stimulation of T cell proliferation. Accordingly, the invention also provides methods for stimulating T cell proliferation, comprising contacting a population of T cells with cells that express CD100 and a primary activation signal. Such cells can be cells which naturally express CD100 on their surface. Alternatively, the CD100 cells for practicing the invention can be cells that have been transfected to express a stimulatory form of CD100. In yet another embodiment, CD100 positive cells are obtained by linking a CD100 molecule to the cell surface, e.g., using cross-linking reagents. A stimulatory form of CD100 can also be linked to a solid phase support, such as a bead. The stimulatory form of a CD100 molecule can be the full length protein. Alternatively, the stimulatory form of CD100 is a stimulatory fragment of CD100. A stimulatory fragment of a CD100 molecule is a fragment of a CD100 molecule which upon interaction with B cells results in stimulation of a B cell response, such as B cell aggregation. Nucleic acids that can be used for preparing stimulatory forms of CD100 as well as methods for expressing these nucleic acids are described above. An assay for confirming that a form of CD100 is a stimulatory form of CD100 is also described above and in the Example section. Briefly, in one such assay, cells containing CD100 on their surface are added to a culture of B cells, and the effect on B cell aggregation is monitored either macroscopically or microscopically. A stimulatory form of a CD100 antigen can also be identified by performing a proliferation assay of T cells incubated in the presence of the form of CD100 to be tested and an anti-CD3 antibody. Alternatively, T cell proliferation can be measured by determining the amount of cytokines, such as IL-2 and IL-4 secreted by the T cells, such as by an ELISA assay. Methods for measuring T cell proliferation are known in the art and can be found for example in the published PCT applications Number PCT/US94/06255 and PCT/US94/08423.

Another preferred stimulatory form of CD100 is a soluble form of CD100. A soluble stimulatory form of CD100 can be prepared by recombinant techniques well known in the art. For example, for preparing a soluble stimulatory form of a CD100 molecule shown in FIG. 2, a nucleic acid fragment having a sequence shown in FIG. 1 (SEQ ID NO: 1) comprising the nucleic acid encoding the semaphorin domain and the Ig-like domain, i.e., about nucleic acid residues 22-630, but not comprising the transmembrane and cytoplasmic domains is expressed in a host cell and purified according to methods known in the art. In a preferred embodiment, the soluble stimulatory form of a CD100 protein comprises a second peptide which modifies the first peptide, such as to increase its stability. A preferred second peptide is an immunoglobulin fragment. These are further described herein.

Other agents which stimulate a CD100 ligand-associated signal in a cell include agents which mimmick the action of a stimulatory form of CD100 on a cell. Such agents include small molecules which interact with a CD100 receptor or cell surface structure and deliver to the B cell a CD100 ligand-associated signal. Small molecules can be isolated from libraries of small molecules, such as combinatorial libraries, using in vitro assays, such as those described above for identifying fragments of CD100 which are capable of inducing a CD100-signal.

Methods within the scope of the invention pertain to the isolation of receptor(s) for CD100 molecules. Accordingly, additional agents which stimulate a CD100 ligand-associated signal in a B cell include agents which interact with the CD100 receptor and deliver a CD100 ligand-associated signal. Preferred stimulatory agents interacting with a CD100 receptor are antibodies to CD100 receptors which deliver to the B cell a CD100 ligand-associated signal. Such antibodies can be prepared as described herein for the preparation of anti-CD100 antibodies. Other agents which stimulate a CD100 ligand-associated signal include constitutively activated forms of CD100 receptors, that can be obtained, for example, by modifying the intracellular domain of the receptor, such that the modified receptor constitutively delivers a CD100 ligand-associated signal to the cell.

The interaction of a CD100 antigen with a leukocyte may result in stimulation of a leukocyte response through a signal delivered to the leukocyte from the CD100 receptor. Alternatively, the interaction of a leukocyte with a cell having a CD100 molecule on its surface may result in secretion of a soluble factor from the leukocyte or the cell having a CD100 molecule on its surface which then stimulates a leukocyte response. Thus, such a soluble factor could also be used as an agent which stimulates a CD100 ligand-associated signal and is also within the scope of the invention. Methods for isolating such a soluble factor are also within the scope of the invention.

In the instance where CD100 is its own receptor, stimulatory agents could be agents which interact with CD100, such as antibodies to CD100, such as the antibodies BD16 (Herold C. et al, (1994), *Int. Immunol* 7, 1), BB18 (Bougeret C., et al., (1992), *J. Immunol.* 148, 318), and F937G2 (Seed B., (1987), *Nature* 329, 840). Antibodies which stimulate CD100 can be prepared according to methods described herein.

B. Agents which Inhibit a CD100 Ligand-Associated Signal

In another embodiment of the invention, the agent which modulates a CD100 signal in a leukocyte is an agent which inhibits a CD100 ligand-associated signal. Inhibitory agents include agents which block stimulatory agents from delivering a CD100 ligand-associated signal and agents which deliver a negative, or inhibitory signal to the cell. Such agents are termed herein "CD100 inhibitors".

Agents which block the transduction of a CD100 ligand-associated signal include agents which interact with a CD100 receptor but fail to deliver a CD100 ligand-associated signal, thereby preventing delivery of a CD100 ligand-associated signal by stimulatory agents. Preferred inhibitory agents include inhibitory forms of CD100 molecules. Such inhibitory forms can, e.g., bind a CD100 receptor, fail to deliver a positive signal and thereby inhibit a CD100 ligand-associated signal. Alternatively, the inhibitory form of CD100 could deliver a negative signal, further inhibiting a B cell response. Inhibitory forms of CD100 can be modified forms of CD100 molecules, fragments of CD100 molecules, or modified fragments. Inhibitory forms of CD100 antigens can be prepared by methods similar to those described herein for the preparation of stimulatory forms of CD100. An inhibitory form of CD100 will preferably comprise the extracellular domain of a CD100 molecule, or at least a portion of the extracellular domain that is necessary for interacting with the CD100 receptor. CD100 molecules or fragments thereof that retain binding capacity to CD100 receptors can then be mutated, such as by site directed mutagenesis for obtaining a form of CD100 or fragment thereof that retains binding capacity but fails to deliver a CD100 ligand-associated signal. The inhibitory efficiency of the inhibitory forms of CD100 can be determined, e.g., in an in vitro assay wherein B cells are incubated in the presence of a stimulatory form of CD100, such as NIH-3T3 cells expressing a full length CD100 molecule on the cell surface. Various amounts of the inhibitory form of CD100 to be tested are added to this assay and a B cell response, such as B cell aggregation is measured. An inhibitory form of CD100 will inhibit or at least reduce B cell aggregation. An inhibitory form of CD100 can also be identified as a form of CD100 which, when added to a culture of T cells in the presence of a primary T cell activation signal and a stimulatory form of CD100 inhibits T cell proliferation.

Additional agents within the scope of the invention which block the transduction of a CD100 ligand-associated signal include agents which interact with CD100 and thereby prevents its interaction with a CD100 receptor. Preferred inhibitory forms of CD100 include antibodies to CD100, such as blocking antibodies. Thus, blocking antibodies to CD100 will interact with CD100 and block its interaction with its ligand, thus inhibiting transduction of a signal from the CD100 ligand. Blocking antibodies can be prepared according to methods known in the art, using, for example, a soluble form of an extracellular domain of CD100 as the antigen. Also within the scope of the invention are soluble forms of CD100 receptors or fragments thereof or modified forms thereof which are capable of interacting with CD100 and blocking its interaction with a CD100 receptor on a cell. The soluble forms of CD100 receptors may also be linked to a solid phase surface. These soluble or membrane bound forms of CD100 receptors can be prepared and modified similarly to the soluble CD100 molecules described herein.

Additional inhibitory agents include small molecules. Thus, it is possible to isolate small molecules which inhibit a signal through CD100 from a library of small molecules using, for example, the assay described above. These molecules can block a CD100 ligand-associated signal by either interacting with CD100 or with its receptor, such that the interaction between CD100 and its receptor is inhibited. Alternatively, the small molecule may interact directly with the CD100 receptor and deliver a negative signal.

Preferred methods for inhibiting a CD100 ligand-associated signal in a leukocyte include contacting a leukocyte with a combination of at least two inhibitory agents. In a particularly preferred embodiment, the method includes contacting a leukocyte with at least one inhibitory agent which interacts with CD100 and with at least one inhibitory agent which interacts with a CD100 receptor.

Other inhibitory agents include CD100 antisense molecules and ribozymes. Thus, delivery of a CD100 ligand-associated signal by a cell expressing CD100 can be inhibited in a cell, such as a B cell or a T cell, by introducing and/or expressing CD100 antisense molecules or ribozymes. Antisense molecules and ribozymes are further described herein. Alternatively, a CD100 ligand-associated signal can be blocked in a cell, such as a B cell or a T cell by blocking the expression of a ligand for CD100 in the cell. Blocking or at least reducing the expression of a CD100 ligand can be obtained by introducing and/or expressing in the T or B cell antisense molecules interacting with a CD100 ligand.

C. Modulation of a B Cell Response by Modulation of a CD100 Ligand-Associated Signal and a CD40 Signal The invention further provides methods for moduling a B cell response comprising contacting the population of cells with a first agent which modulates a CD100 ligand-associated signal and a second agent which modulates a CD40 signal. Similarly to CD100 stimulation, resting B cells receiving a CD40 mediated contact dependent signal from CD40L on activated T cells are stimulated to aggregate, cluster, and proliferate (Banchereau J. et al., (1994), *Annu. Rev. Immunol.* 12, 881; Clark E. A. et al, (1994), *Nature* 367, 425. As also shown herein (Example 4), CD40 ligand (CD40L) transfectants (t-CD40L) induce B cells to aggregate and form clusters. It has been shown herein that B cell aggregation and cell survival induced by stimulation of B cells through CD100 is synergistically increased by simultaneously stimulating the cells through CD40. Thus, in a preferred method of the invention, a population of cells is contacted with an agent which provides a stimulatory signal through CD100 and an agent which provides a stimulatory signal through CD40. Also within the scope of the invention are methods for inhibiting a B cell response comprising contacting B cells with at least one first agent which inhibits a CD100 signal and at least one second agent which inhibits a CD40 signal, such that a B cell response is inhibited.

D. Additional Methods of Use of CD100 Antigens

In another embodiment of the invention, the B cells which are contacted with an agent which stimulates a CD100 ligand-associated signal are further contacted with T cells. Thus, since CD100 provides a costimulatory signal to T cells, these T cells will provide help to the B cells for further stimulating a B cell response. In yet another embodiment, the population of cells comprising B and T cells further comprises at least one primary activation signal, such as an antigen, for example on an antigen presenting cell, or an anti-CD3 antibody.

The methods of the invention can be practiced in vitro or in vivo. For example a stimulatory form of a CD100-like molecule can be added to a culture of B cells, such as a hybridoma culture, such that the production of antibodies by the hybridomas is increased. Alternatively, the molecules of the invention can be added to a population of T cells, such that their proliferation in vitro is stimulated. The molecules of the invention can also be added to a culture of primary B cells or T cells obtained from an individual for stimulating their differentiation and proliferation, respectively.

V. Applications of the Invention

The invention provides a method for modulating a leukocyte response comprising contacting the leukocytes with an agent which modulates a CD100 ligand-associated signal in the leukocytes. In one embodiment, the invention provides a method for stimulating a B cell response. Stimulation of a B cell response can result in increased B cell aggregation, increased B cell differentiation and/or increased B cell survival. The B cells can, for example, be stimulated to differentiate from a lymphoblast to a centroblast or centrocyte and thereby stimulate the differentiation of B cells into either antibody secreting plasma cells or memory B cells. In another embodiment, the invention provides a method for stimulating a T cell response, such as T cell proliferation. In a preferred embodiment, the invention provides a method for stimulating a B cell response and a T cell response, such as T cell proliferation. Thus, the presence of a stimulatory form of CD100 in a population of cells comprising both B cells and T cells should further amplify the B cell response stimulated by CD100. It will be appreciated that it is particularly advantageous to stimulate both B cells and T cells for most applications.

In one embodiment, the invention provides a method of vaccination. Accordingly, a subject in need of vaccination is given a dose of at least one antigen in the presence of a therapeutically effective amount of an agent which stimulates a CD100 ligand-associated signal. The antigen and the stimulatory agent are preferably administered simultaneously. Alternatively, the antigen and the stimulatory agent are administered separately, such that, for example, the antigen is administered prior to the stimulatory agent. In a preferred embodiment, the subject is subsequently boosted at least once with additional doses of antigen and the stimulatory agent. The antigen can be any molecule, or structure against which it is desirable to have a strong and rapid immune reaction. Thus, antigens within the scope on the invention include viral antigens, bacterial antigens, tumor antigens, or any antigens, or combination of antigens from any organism. An agent which stimulates a CD100 ligand-associated signal can be added to any classic vaccine composition for preventing an infection in a subject.

In a preferred embodiment, the vaccine formulation further comprises a therapeutically effective dose of an agent which stimulates CD40. Thus, the subject is contacted with at least one antigen, an agent which stimulates a CD100 ligand-associated signal and a an agent which stimulates CD40. In a preferred embodiment, the CD40 and the agent which stimulates a CD100 ligand-associated signal are administered together to the subject, which is also preferably administered together with the antigen(s). Further boosting of the subject with the antigen(s) is preferably performed by administering the antigen(s) and the stimulatory CD40 agent and/or the agent which stimulates a CD100 ligand-associated signal.

An agent which stimulates a CD100 ligand-associated signal can also be used for treating disorders in which boosting of a B cell response is beneficial. Such disorders include infections by pathogenic microorganisms, such as bacteria, viruses, and protozoans. Preferred disorders for treating according to the method of the invention include extracellular bacterial infections, wherein bacteria are eliminated through opsonization and phagocytosis or through activation of the complement. Other preferred infections that can be treated according to the method of the invention include viral infections, including infections with an Epstein-Barr virus or retroviruses, e.g., a human immunodeficiency virus.

In another embodiment of the invention, an agent which stimulates a CD100 ligand-associated signal can be administered to a subject having an antibody deficiency disorder resulting, for example, in recurrent infections and hypogammaglobulinemia (Ochs et al. (1989) Disorders in Infants and Children, Stiehm (ed.) Philadelphia, W. B. Sanders, pp 226-256). These disorders include common variable immunodeficiency (CVI), hyper-IgM syndrome (HIM), and X-linked agammaglobulinemia (XLA). Some of these disorders, e.g., HIS, are caused by a mutation in the CD40 ligand, gp39, on the T cell and administration of an agent which stimulates a CD100 ligand-associated signal would thus compensate for at least some of the B cell deficiencies, such as stimulation of B cell differentiation.

Furthermore, upregulation of a B cell response is also useful for treating a subject with a tumor. In one embodiment, an agent which stimulates a CD100 ligand-associated signal is administered at the site of the tumor. In another embodiment, an agent which stimulates a CD100 ligand-associated signal is administered systemically.

In another embodiment, the invention provides a method for stimulating B cells in culture, such as hybridoma cells. In a preferred embodiment, stimulation of the population of B cells results in increased antibody production. Thus, an agent which stimulates a CD100 ligand-associated signal can be added at an effective dose to a B cell culture, such as a hybridoma, such that antibody production by the B cells is enhanced. The effective dose of the agent which stimulates a CD100 ligand-associated signal to be added to the culture can easily be determined experimentally. This can be done, for example, by adding various amounts of the agent to a constant amount of B cells, and by monitoring the amount of antibody produced, e.g., by ELISA. The effective dose corresponds to the dose at which highest amounts of antibodies are produced.

In yet another embodiment, an agent which stimulates a CD100 ligand-associated signal is administered together with a hybridoma into the peritoneal cavity of a mouse, such that the amount of antibody produced by the hybridoma is increased.

In another embodiment of the invention, a T cell is contacted with an agent which stimulates a CD100 ligand-associated signal and a primary activation signal, such that T cell proliferation is increased. The primary activation signal can be an antigen, or a combination of antigens, such that proliferation of one or more clonal populations of T cells is stimulated. Alternatively the primary activation signal can be a polyclonal agent, such as an antibody to CD3, such that T cell proliferation is stimulated in a non clonal manner.

In one embodiment, the invention provides a method for expanding a population of T cells ex vivo. Accordingly, primary T cells obtained from a subject are incubated with an agent which stimulates CD100 ligand-associated signal and a primary activation signal. Following activation and stimulation of the T cells, the progress of proliferation of the T cells in response to continuing exposure to the agent which stimulates a CD100-induced signal is monitored. When the rate of T cell proliferation decreases, the T cells are reactivated and restimulated, such as with additional anti-CD3 antibody and an agent which stimulates a CD100-induced signal in the T cell, to induce further proliferation. The monitoring and restimulation of the T cells can be repeated for sustained proliferation to produce a population of T cells increased in number from about 100- to about 100,000-fold over the original T cell population. Methods for stimulating the expansion of a population of T cells are further described in the published PCT application PCT/US94/06255 and can be practiced by using an agent which is capable of stimulating a CD100 ligand-associated signal as the costimulatory molecule. In a preferred embodiment, T cell expansion is obtained by incubating the T cells with a primary activation signal and at least two costimulatory signals, such as a molecule providing a costimulatory signal through a CD28 or CTLA4 receptor, such as B7-1 or B7-2, and a costimulatory molecule that stimulates a CD100 ligand-associated signal.

The method of the invention can be used to expand selected T cell populations for use in treating an infectious disease or cancer. The resulting T cell population can be genetically transduced and used for immunotherapy or can be used for in vitro analysis of infectious agents such as HIV. Proliferation of a population of CD4+ cells obtained from an individual infected with HIV can be achieved and the cells rendered resistant to HIV infection. Following expansion of the T cell population to sufficient numbers, the expanded T cells are restored to the individual. The expanded population of T cells can further be genetically transduced before restoration to a subject. Similarly, a population of tumor-infiltrating lymphocytes can be obtained from an individual afflicted with cancer and the T cells stimulated to proliferate to sufficient numbers and restored to the individual. In addition, supernatants from cultures of T cells expanded in accordance with the method of the invention are a rich source of cytokines and can be used to sustain T cells in vivo or ex vivo.

In another embodiment of the invention, T cell proliferation is stimulated in vivo. In a preferred embodiment, an agent which stimulates a CD100 ligand-associated signal in the T cell is administered to a subject, such that T cell proliferation in the subject is stimulated. The subject can be a subject that is immunodepressed, a subject having a tumor, or a subject infected with a pathogen. The agent of the invention can be administered locally or systemically. The agent can be administered in a soluble form or a membrane bound form. Additional applications for an agent capable of providing a costimulatory signal to T cells, such that their proliferation is stimulated, are described in the published PCT applications PCT/US94/13782 and PCT/US94/08423, the content of which are incorporated herein by reference.

The invention further provides inhibitors of a CD100 ligand-associated signal. In a specific embodiment, an inhibitory CD100 agent is used for prolonging graft survival. Thus, a therapeutically effective dose of an inhibitor of a CD100-signal is administered to a recipient of an allotypic or xenotypic graft, such that graft survival is prolonged at least in part by reducing a B cell response to the graft. In a preferred embodiment, the inhibitor of a CD100 ligand-associated signal is administered prior to transplantation of the graft, such that B cell responses are downregulated at the time of translplantation. Alternatively, the inhibitor of a CD100-signal can be administered at about the same time as transplantation of the graft or after transplantation of the graft. In preferred embodiments, the inhibitor of a CD100-signal is administered together with an inhibitor of a CD40-induced signal to further block B cell responses. Additional agents, such as agents which block T cell activation and clonal expansion, can also be administered to the graft recipient. Such agents include antibodies to B7-1, B7-2, a combination thereof, and CTLA4Ig.

In yet another embodiment of the invention, an inhibitor of a CD100 signal can be used to prevent graft versus host disease (GVHD). In a preferred embodiment, the donor bone marrow is incubated with an inhibitor of a CD100-signal prior to administration to the recipient. The treatment can further include administration of a therapeutically effective dose of a CD100 inhibitor to the bone marrow recipient prior to and/or after bone marrow transplantation. As described in the treatment for prolonging graft survival, the CD100 inhibitor can be used together with a CD40 inhibitor and/or with yet additional agents.

Inhibitors of CD100 can also be used to reduce B cell and/or T cell responses in autoimmune diseases which involve autoreactive B and/or T cells. Accordingly, administration of an inhibitor of CD100 to a subject can be used for treating a variety of autoimmune diseases and disorders having an autoimmune component, including diabetes mellitus, arthritis (including rheumatoid arthritis, juvenile rheumatoid arthritis, osteoarthritis, psoriatic arthritis), multiple sclerosis, myasthenia gravis, systemic lupus erythematosus, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis.

The efficacy of a CD100 inhibitor in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., *Fundamental Immunology*, Raven Press, New York, 1989, pp. 840-856).

It is possible to treat a subject having an allergy with an agent, such as an agent which blocks a CD100 ligand-associated signal, which inhibits or reduces production of IgE antibodies to thereby ameliorate the allergic reaction. Allergic reactions may be systemic or local in nature, depending on the route of entry of the allergen and the pattern of deposition of IgE on mast cells or basophils. Thus, in various embodiments for treating allergies, the agent is administered either systemically or locally. Alternatively, the allergen can be administered together with an agent which blocks a CD40 signal. The treatment can further comprise adminstration of an agent which neutralizes IL-4, such as an anti-IL4 antibody.

Additional disorders for which the agents of the invention provide a treatment include lymphomas which are characterized by abnormal B cells. It has been shown by immunohistopathology that some lymphomas are characterized by high expression of CD100, whereas other types of lymphomas are characterized by low level expression of CD100. Lymphomas characterized by a block in B cell differentiation express low levels of CD100. Thus, agents which stimulate a CD100 ligand-associated signal can be used to treat lymphomas which are characterized by a block in B cell differentiation, such that differentiation of the lymhoma cells is stimulated. Such lymphomas are characterized by small, well-differentiated lymphocytes and include low-grade lymphomas, such as small lymphocytic and follicular lymphomas. In one embodiment of the invention, an agent which stimulates a CD100 ligand-associated signal, such as a soluble stimulatory form of CD100, is administered to a subject having a low grade lymphoma, such that differentiation of the lymphoma cells is stimulated. Lymphomas characterized by an excessive proliferation and/or differentiation of B cell differentiation express high levels of CD100. Thus, inhibitors of CD100 can be used for treating a subject having a lymphoma characterized by an excessive proliferation and/or differentiation of B cells, such that their proliferation and/or differentiation is inhibited. Such lymphomas are characterized by larger, poorly differentiated lymphocytes and large lymphocytes with characteristics of a histiocyte or lymphoblast and include: intermediate grade lymphomas, such as follicular large cell, diffuse small cleaved cell, diffused mixed cell, and diffuse large cell lymphomas; high grade lymphomas, such as immunoblastic, small noncleaved (Burkitt's and non-Burkitt's), lymphoblastic, and true histiocytic lymphomas. In one embodiment, an inhibitor of CD100 is administered to a subject having a large cell lymphoma, such that proliferation and/or differentiation of the lymphoma cells is inhibited.

Additional applications for an agent capable of inhibiting a costimulatory signal in T cells, such that T cell proliferation is inhibited, are described in the published PCT applications PCT/US94/13782 and PCT/US94/08423, the content of which are incorporated herein by reference.

In preferred embodiments of the invention agents which modulate a CD100 ligand-associated signal are preferably administered to subject together with agents which modulate other costimulatory signals. For example, in a method for preventing graft rejection, it is preferable to administer to a subject having been transplanted an agent which inhibits a CD100 ligand-associated signal together with agents which inhibit a costimulatory signal delivered by a member of the B7 family of proteins, such as B7-1 and B7-2. In a preferred embodiment, an agent which blocks a CD100 associated signal is administered together with anti-B7-1 and/or anti-B7-2 antibodies, or CTLA4Ig. The method can further comprise administering to the subject additional agents, such as agents which inhibits the interaction of growth or differentiation factors with their receptors.

Also within the scope of the invention are diagnostic methods. It has been shown, for example, that B cell lymphomas are associated with a high level of CD100 expression. Thus, determining the level of CD100 expression in a lymph node section from a patient having enlarged lymph nodes using an agent that binds CD100 could be indicative of lymphoma. Detection of CD100 can also be performed using a nucleic acid probe that selectively recognizes the gene encoding CD100. A specific probe can be a portion of a nucleic acid having a SEQ ID NO: 1. Other disorders associated with a high level of CD100, a CD100 ligand, a CD100-like molecule or receptor thereof could similarly be detected using agents of the invention.

Since the semaphorin domain of CD100 shares some homology with other semaphorin family members, such as H-Sema III and M-Sema C, it is likely that CD100 interacts with at least some of these neurological semaphorins. However, since the semaphorins identified in the nervous system act as chemorepellants, it is possible that CD100 is repulsive towards these neurological semaphorins. Thus, whether CD100 or CD100 ligand(s) act as chemorepellants or chemoattractants vis a vis the neurological semaphorins, blocking the interaction between an immune semaphorin, or receptor thereof, and a neurologic semaphorin, or receptor therof, will result in modulation of the interaction between the immune and the nervous system. Such a modulation will be of interest in treating diseases characterized by an abnormal interaction between the immune and nervous systems.

Furthermore, if CD100 or its receptor(s) is capable of interacting with or repulsing neurologic semaphorins, the agents of the invention can be used for treating neurological diseases. Thus, depending on the disease to be treated, an agent of the invention which blocks or which stimulates interaction between neurons can be administered to a subject having the disease. Applications for CD100 agents or ligands in neurology include treatments for nerve damages, such as spinal cord injuries. The agents of the invention can also be used to direct regenerating neurons to their target.

Semaphorins are expressed during embryonic development. Thus, since CD100 is structurally related to at least some semaphorins, CD100 may also be involved in embryogenesis. Thus, CD100 agents could be useful in the regeneration of tissues or organs.

The invention can also be used to isolate one or more ligands of CD100 or CD100 like molecules. Various methods can be used for isolating ligands of CD100. A preferred method for isolating a CD100 ligand comprises screening of an expression library with CD100, such as a soluble form of CD100, according to methods known in the art. The expression library can be prepared from various tissues, preferably leukocytes, and even more preferably B lymphocytes. Thus, according to this method, a cDNA expression library is constructed using mRNA from B lymphocytes and the library is transfected into cells, preferably COS cells. The transfected cells are then incubated with a soluble form of CD100 that is tagged, e.g., with a biotin molecule. Cells binding CD100 are then detected by incubating the cells with a secondary reagent that is labelled and the cells are sorted by FACS analysis or using magnetic beads coated with a reagent that reacts with the CD100 labelled cells. The plasmids containing the cDNA are extracted, retransfected into COS cells, and rescreened with CD100. Following several rounds of screening, the plasmids are isolated and the insert is sequenced. A basic expression cloning technique has been described by Seed and Aruffo, *Proc. Natl. Acad. Sci. USA*, 84:3365-3369 (1987) and Aruffo and Seed, *Proc. Natl. Acad. Sci. USA*, 84:8573-8577 (1987), although modifications to this technique may be necessary. The technique is also described in the published PCT application PCT/US94/08423.

VI. Pharmaceutical Compositions

The CD100 proteins and other agents described herein can be incorporated into pharmaceutical compositions suitable for administration. Such compositions typically comprise the protein or agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In one embodiment, the agents of the invention can be administered to a subject to modulate a B cell response in the subject, e.g., for stimulating the clearance of a pathogen from the subject. The agents are administered to the subjects in a biologically compatible form suitable for pharmaceutical administration in vivo. By "biologically compatible form suitable for administration in vivo" is meant a form of the agents, e.g., protein to be administered in which any toxic effects are outweighed by the therapeutic effects of the agent. The term "subject" is intended to include living organisms in which an immune response can be elicited, e.g., mammals. Examples of subjects include humans, dogs, cats, mice, rats, and transgenic species thereof. Administration of a therapeutically active amount of an agent of the present invention is defined as an amount effective, at dosages and for periods of time necessary to achieve the desired result. For example, a therapeutically active amount of a stimulatory form of a CD100 molecule, alone or together with a stimulatory form of a CD40 ligand, may vary according to factors such as the disease state, age, sex, and weight of the subject, and the ability of agent to elicit a desired response in the subject. Dosage regimens may be adjusted to provide the optimum therapeutic response. For example, several divided doses may be administered daily or the dose may be proportionally reduced as indicated by the exigencies of the therapeutic situation.

The agent may be administered in a convenient manner such as by injection (subcutaneous, intravenous, etc.), oral administration, inhalation, transdermal application, or rectal administration. Depending on the route of administration, the agent may be coated in a material to protect it from the action of enzymes, acids and other natural conditions which may inactivate the agent. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

To administer an agent by other than parenteral administration, it may be necessary to coat the agent with, or co-administer the agent with, a material to prevent its inactivation. For example, a stimulatory form of a CD100-like molecule may be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) *J. Neuroimmunol* 7:27). Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the agent in the required amount in an appropriate solvent with one or a combination of ingredients enumerated above, as required, followed by filtered sterilization. Generally, dispersions are prepared by incorporating the agent into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., peptide) plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of individuals.

This invention is further illustrated by the following Exemplification which should not be construed as limiting. The contents of all references and published patent applications cited throughout this application are hereby incorporated by reference.

EXEMPLIFICATION

Example 1

Isolation of a cDNA Encoding CD100

A cDNA encoding a human CD100 antigen was isolated by COS cell expression cloning using an anti-CD100 antibody. (cDNA library was constructed in pCDM8 (Aruffo A et al, (1987), *Proc. Natl. Acad. Sci. USA* 84, 8573; Seed B et al, (1987), *Proc. Natl. Acad. Sci. USA* 84, 3365) using poly (A)+RNA from PHA activated human T cells and size selected for inserts greater than 3 kb. The library was introduced into COS cells by DEAE-dextran transfection and CD100 expressing cells selected by two rounds of immunoselection and panning with CD100 mAb BD16 (cDNA library was constructed in pCDM8 (9,32) using poly (A)+ RNA from PHA activated human T cells and size selected for inserts greater than 3 kB. The library was introduced into COS cells by DEAE-dextran transfection and CD100 expressing cells selected by two rounds of immunoselection and panning with CD100 mAb BD16 (33,8). Twelve of 16 plasmids isolated contained a 4.2 kB Xba insert and COS cells individually transfected bound to BD16 but not to control Mouse IgG$_1$. Herold C. et al, (1994), *Int. Immunol* 7, 1). Twelve of 16 plasmids isolated contained a 4.2 kb Xba insert and COS cells individually transfected bound to BD16 but not to control Mouse IgG$_1$.

Figure 5:
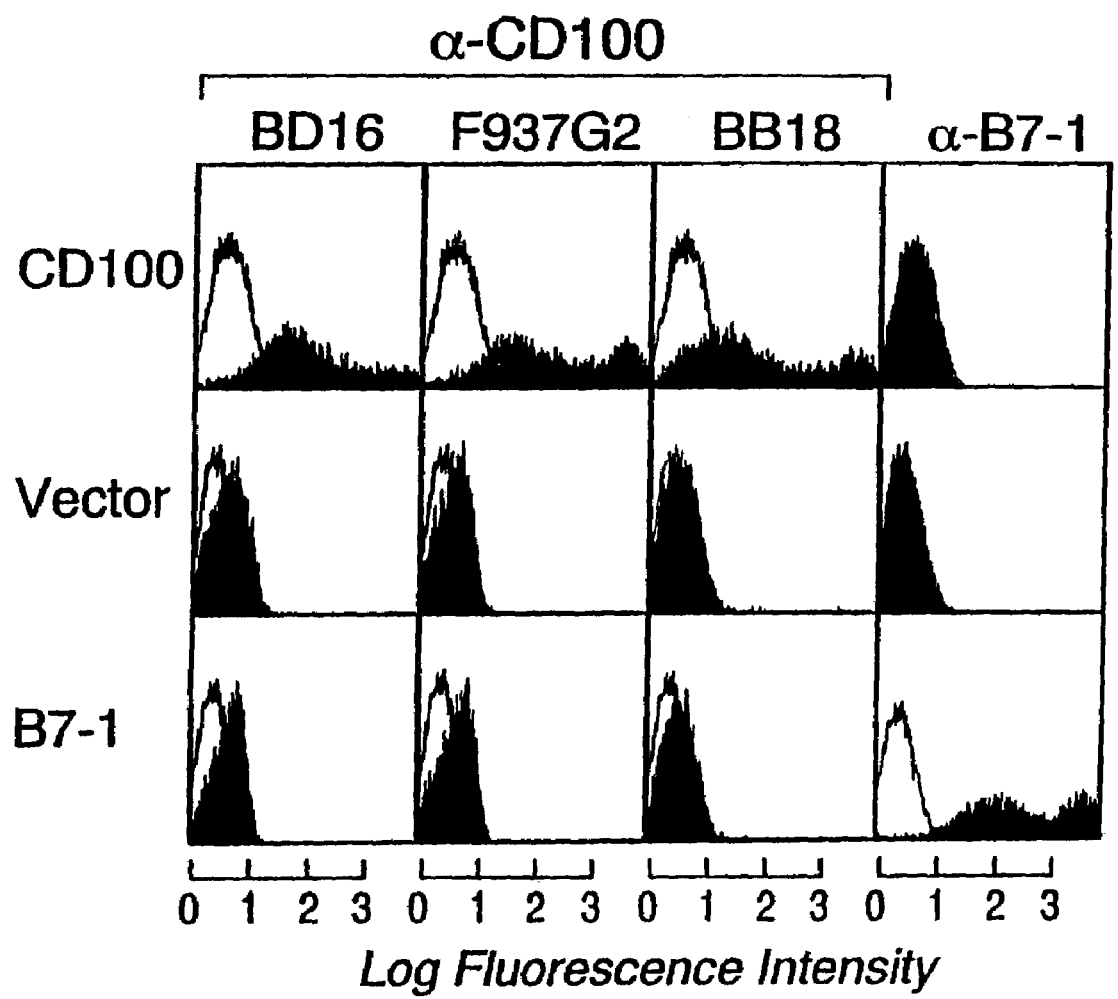
FIG. 5 is a graphic representation of the result of flow cytometry analyses of COS cells transiently transfected with a CD100 cDNA (CD100), pCDM8 vector alone (Vector), and B7-1 cDNA (B7-1) and stained with the anti-CD100 antibodies BD16, F93G2, and BB18; and with the isotype matched B7-1 antibody B1.1.

To confirm that the isolated 4.2 kb cDNA encodes CD100, COS cells were transiently transfected with the 4.2 kb CD100 cDNA, pCDM8 vector alone, and B7-1 cDNA. After 48 hours, cells were stained with antibodies against CD100-BD16 (Herold C. et al, (1994), *Int. Immunol.* 7, 1), BB18 (Bougeret C et al., (1992), *J. Immunol.* 148, 318) and F937G2 (Seed B., (1987), *Nature* 329, 840), and an isotype matched B7-1 antibody, B1.1. Binding of the mAbs was detected by indirect immunofluorescence using goat anti-mouse IgG$_1$-phycoerythrin and analyzed by flow cytometry. FIG. 5, which represents the results of the flow cytometry analysis, show that the COS cells transfected with the 4.2 kb cDNA bind specifically to three monoclonal antibodies (mAbs) directed against CD100 (Herold C et al, in *Leucocyte Typing* V, S. F. Schlossman, et al., Eds. (Oxford University Press, Oxford, 1995), vol. 1, pp. 50), but not to control mAbs. Non transfected COS cells do not stain with the anti-CD100 antibodies. These results indicate that the 4.2 kb cDNA encodes CD100.

Figure 6:
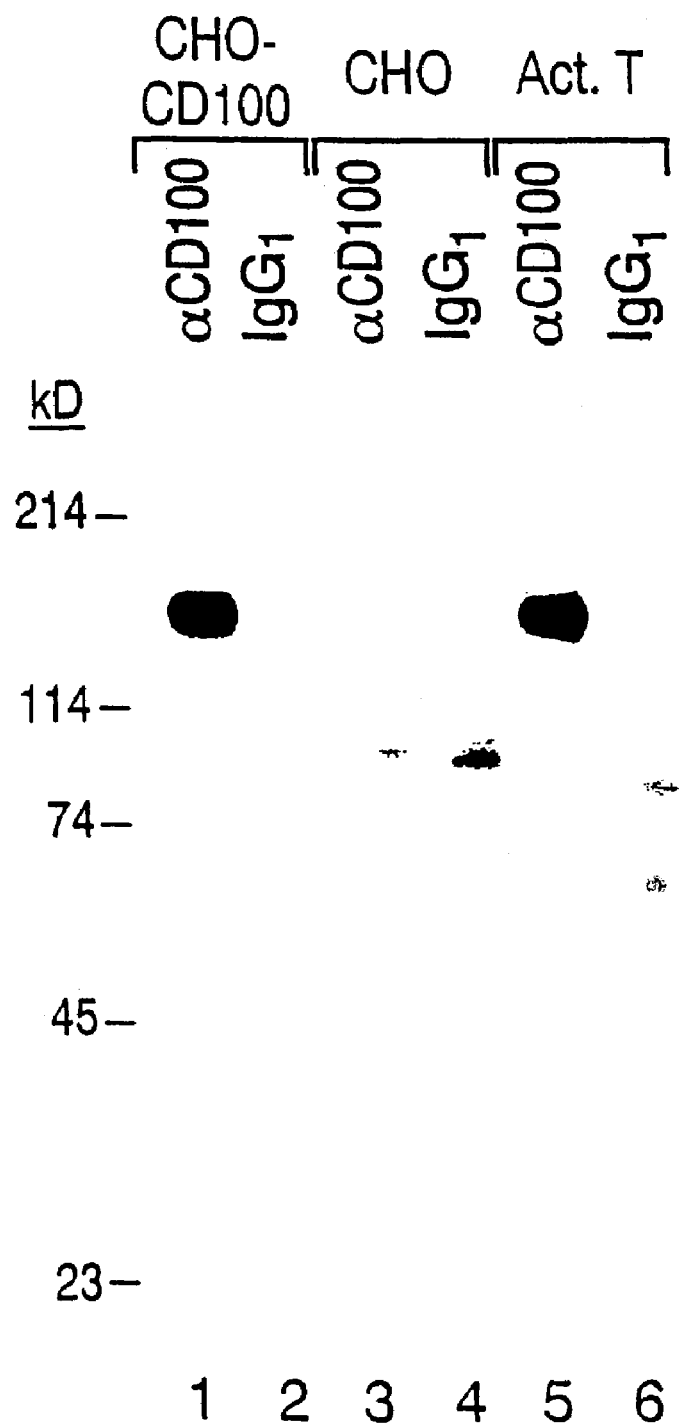
FIG. 6 is a photograph of a Western blot showing that the anti-CD100 antibody BB18 immunoprecipitates a 150 kDa protein from CHO cells transfected with a CD100 cDNA (CHO-CD100) and from activated T cells, but not from non-transfected CHO cells (CHO).

Further confirmation that the isolated 4.2 kb cDNA encodes CD100 was provided by immunoprecipitation experiments. CHO cells were stably transfected with CD100 cDNA or vector alone and $^{125}$I labeled. Cell lysates were immunoprecipitated with BB18 antibody or a control antibody, IgG1, and separated on an 8.5% SDS-PAGE gel. The results are represented in FIG. 6. These results indicate that a 150 kDa protein is immunoprecipitated from CHO cells transfected with CD100 and from activated T cells, but not from untransfected CHO cells. Activated B cells also express a 150 kDa protein that is immunoprecipitated with an anti-CD100 antibody.

The nucleotide sequence of CD100 was determined for both strands of the original 4.2 kb clone and another clone 4.2H which was isolated from the same library by hybridization. The sequencing was carried out using synthetic oligonucleotide primers and dye-labeled terminator/Taq polymerase chemistry, and analyzed on an automated fluorescent DNA sequencer (Applied Biosystems). The sequence of the CD100 cDNA reveals a single long open reading frame of 2.6 kb, which is represented in FIG. 1. Initiation of translation is likely to occur at the second ATG which, unlike the first ATG, is in a favorable context for translation initiation (Kozak M., (1995), *Proc. Natl. Acad. Sci. USA* 92, 2662; Kozak M., (1989), *J. Cell. Biol.* 108, 229). The CD100 sequence is deposited in Genbank under accession number A BLAST (Altschul S. F. et al, (1990), *J. Mol. Biol.* 215, 403) search of the protein database indicated that CD100 is a novel protein, which has some homology to the semaphorin gene family. The amino acid sequence deduced from the 4.2 kb CD100 cDNA was compared to sequences using CLUSTAL. FIG. 2 represents a comparison of the H-Sema III and mouse Sema C (M-Sema C) amino acid sequences. CD100 shares 39% identity with H-sema III in the sema domain and 33% identity in the Ig-like domain, whereas the rest of the protein is strikingly divergent. As seen in FIG. 3, the CD100 protein consists of a signal sequence followed by a sema domain, an Ig domain, a lysine-rich stretch of 104 amino acids, a hydrophobic transmembrane region and a cytoplasmic tail of 110 amino acids. A consensus site for tyrosine phosphorylation, KPALTGY at amino acid 813 in the cytoplasmic tail supports the predicted association of CD100 with a tyrosine kinase (Sidorenko S et al, "Identification of antigens associated with protein kinases by activation antigens panel mAb." S. F. Schlossman, et al., Eds., *Leucocyte Typing V* (Oxford University Press, Oxford, 1995), vol. 1: Rudd C et al., "Identification of antigens associated with protein kinases by activation antigen panel mAb." S. F. Schlossman, et al., Eds., *Leucocyte Typing V* (Oxford University Press, Oxford, 1995), vol. 1). CD100 contains 15 of the 16 conserved sema domain cysteines and 9 putative N-linked glycoslyation sites.

Thus, CD100 is a novel leukocyte semaphorin-like protein.

Example 2

CD100 is Expressed on Activated B and T Cells and in Non Hematopoietic Tissues

Figure 7:
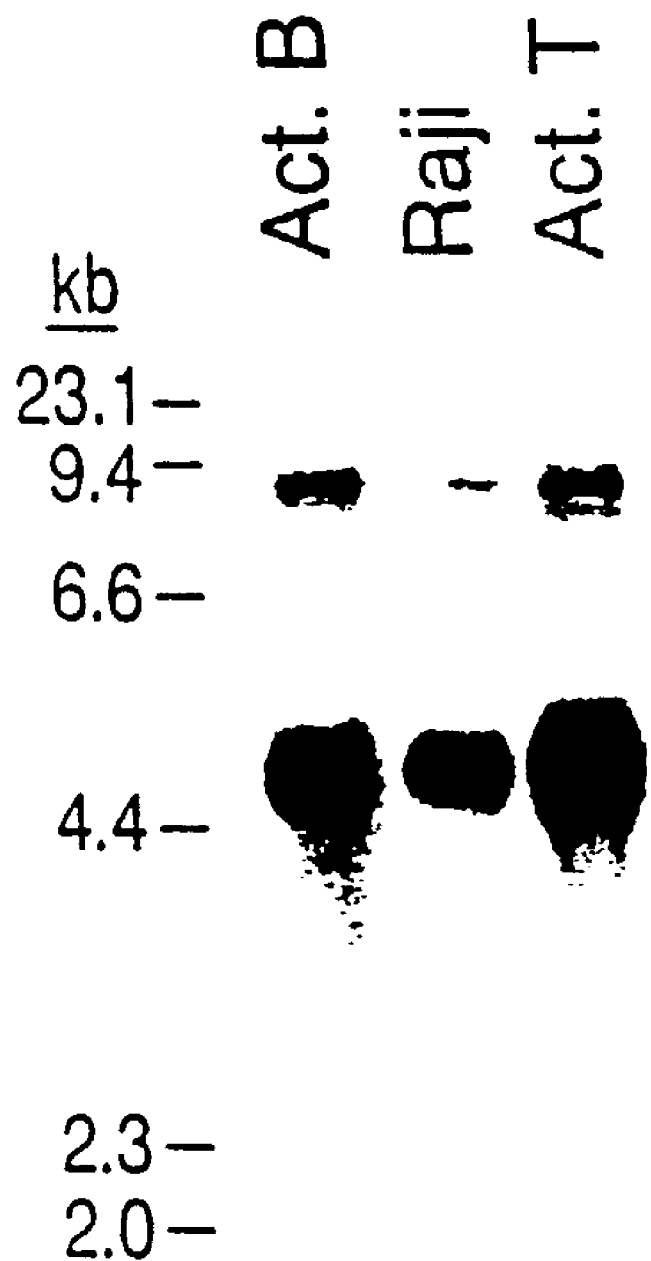
FIG. 7 is a photograph of a Northern blot hybridization depicting the expression of CD100 mRNA in activated B cells (Act. B), Raji cells (Raji), and activated T cells (Act. T).

The level of CD100 mRNA was measured in several tissues by Northern blot analysis. 5 µg poly(A)+RNA from activated B cells, Raji cells and activated T cells was separated by electrophoresis, transfered onto blots and hybridized with labeled 4.2 kb CD100 cDNA. The results are presented in FIG. 7. These results indicate that CD100 expression is high in activated B and T cells and in Raji cells. Expression of CD100 is low in resting B and T cells.

Figure 8:
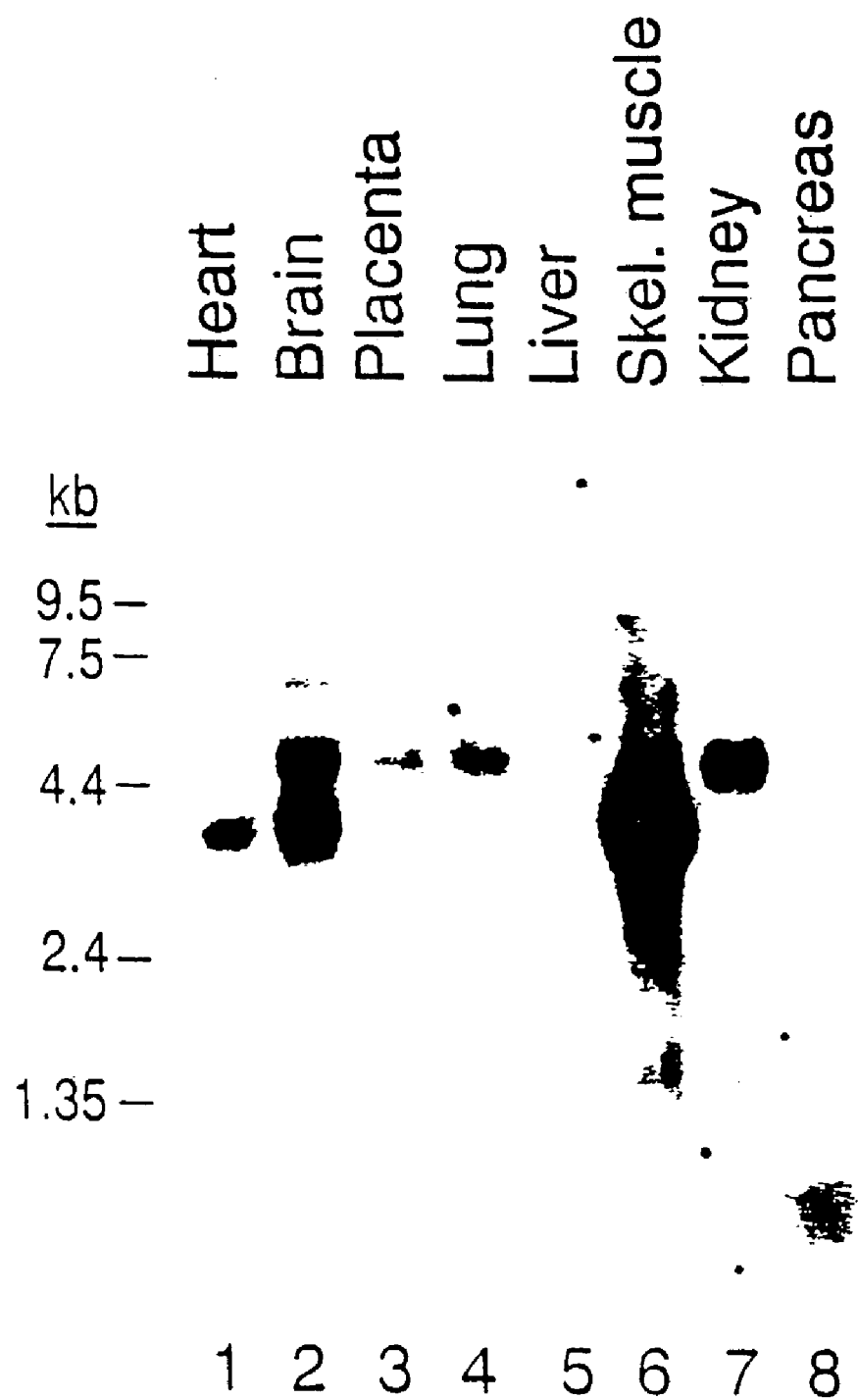
FIG. 8 is a photograph of a Northern blot hybridization depicting the expression of CD100 mRNA in different tissues.

Expression of CD100 was also analysed in various non hematopoietic tissues by Northern blot analysis. For this example, 2 µg of poly(A)+RNA was separated, blotted and hybridized with labeled 4.2 kb CD100 cDNA. The results, presented in FIG. 8, indicate that CD100 mRNA is expressed in many non-hematopoietic tissues including the heart, brain, placenta, lung, skeletal muscle, kidney and pancreas, but not the liver. Interestingly, the three major transcripts of 3.8, 4.5, and 7 kb are differentially expressed with a distinct tissue distribution of transcripts.

Example 3

CD100 is Primarily Expressed in Activated B Cells within the Lymphoid Follicle Germinal Center In this example, the level of CD100 protein was measured in lymphoid tissues by immunohistochemistry.

Cryostat sections of lymphoid tissue were fixed in acetone for ten minutes, washed with PBS and incubated for one hour with the following primary antibodies: a mouse monoclonal antibody against CD100, a mouse monoclonal antibody against CD20, a pan-B cell marker, and a monoclonal antibody against CD3, a pan-T cell marker. The sections were then washed with PBS, incubated with biotinylated horse anti-mouse antibody (Vector Laboratories, Burlingame, Calif.) for 30 minutes, washed with PBS, incubated with avidin:biotinylated-peroxidase complex (Vector Laboratories, Burlingame, Calif.) for 40 minutes, and reacted with diaminobenzidine/hydrogen peroxide. Sections were subsequently stained with 2% methyl green.

The results are presented in FIGS. 9a-c. FIG. 9a shows that anti-CD100 mAb staining is primarily in the germinal center (GC), sporadic in the interfollicular areas and virtually absent in the mantle zone (MZ). This pattern differs from antibodies which stain with a dendritic cell pattern (e.g. CD23) and is consistent with B cell surface staining. FIG. 9b indicates that a mAb against the B cell restricted molecule, CD20, stains most cells in both the GC and the MZ. FIG. 9c shows that a mAb against the T cell restricted molecule, CD3, stains cells in the interfollicular areas but very few cells in the GC and MZ. For comparison, a lymphoid tissue section was fixed in 10% buffered formaldehyde, paraffin embedded, sectioned and stained with hematoxylin and eosin is represented in FIG. 9d. This section shows a germinal center and mantle zone of a secondary lymphoid follicle with interfollicular T cell zone. The results of this experiment indicate that he major hematopoietic cell type that encounters CD100 in the GC is the B lymphocyte. Furthermore, given the paucity of T cells in this lymphoid compartment, the major source of CD100 in the GC is likely to be activated B cells.

Thus, consistent with the high levels of CD100 mRNA expression in activated B cells, anti-CD100 mAb predominantly stained activated B cells within the lymphoid follicle germinal center.

Example 4

CD100 Stimulates B Cell Homotypic Aggregation and Synergizes with CD40L

The effect of CD100 on B cells, was analyzed in an in vitro model system using stable CD100 transfectants (t-CD100). NIH-3T3 cells were mock transfected, transfected with CD100 cDNA or with CD40L cDNA. Transfected cells were harvested, irradiated (96 Gy), plated at a fixed concentration of $10^5$ total transfectants/well and incubated overnight. Human splenic B cells were cultured on the different transfectants at $10^6$ B cells per 1 ml culture in 24-well plates in B cell medium (Carriere D et al., (1989), *Exp. Cell. Res.* 182, 114). Photographs of cell cultures were taken at a magnification of 100× at 72 hrs.

As shown in FIG. 10d, the results of this example indicate that co-culture of human tonsillar B cells with irradiated t-CD100 stimulates the B cells to homotypically aggregate within 24 hours and form continually increasing clusters that are maximal in size by day 3. In contrast, no significant clusters were observed in the mock transfected controls (FIG. 10a). Other B cell sources including splenic B cells, follicular lymphoma, and acute lymphoblastic leukemias are similarly induced to cluster by co-culture with t-CD100. FIG. 10b, indicates that CD40L transfectants (t-CD40L) also induce B cells to aggregate and form clusters. To examine the outcome of combining CD40L and CD100 signals, B cells were cultured on equal numbers of t-CD100 and t-CD40L, i.e., 50% t-CD100/50% t-CD40L (hereinafter referred to as t-CD100/t-CD40L). The total number of transfectants was constant (i.e., identical to number plated in the t-mock, t-CD40L, or t-CD100 wells). FIG. 10f shows that the combination of CD100 and CD40L signaling synergizes to give rise to extraordinarily large B cell clusters that were larger than those observed with either transfectant alone or with the control. Other ratios of transfectants were also examined (75% t-CD100/25% t-CD40L and 25% t-CD100/75% t-CD40L) and these consistently induce larger clusters than observed with t-CD40L or t-CD100 alone, or the equivalent t-mock/t-CD40L control. Taken together, these results demonstrate that CD100 can directly induce B cell cluster formation, moreover, and that, when the CD100 and CD40L signals are combined, cluster formation is markedly enhanced.

The adhesion molecules LFA-3, LFA-1 and ICAM-1 are not upregulated by t-CD100 or t-mock whereas t-CD40L upregulates these adhesion molecules on human B cells (Carriere D et al., (1989), *Exp. Cell. Res.* 182, 114). Furthermore, these adhesion molecules were similarly upregulated on tonsillar B cells following culture on t-mock/t-CD40L or t-CD100/t-CD40L. Thus, these results indicate that the CD100 induced B cell aggregation is not mediated by an increase in LFA-3, LFA-1, or ICAM-1. However, these results do not exclude the possibility that other adhesion molecules might be responsible for this observation or alternatively that cluster formation results form the induction of conformational changes in adhesion molecules (Chan B. M. et al, (1991), *J. Immunol.* 147, 398).

Example 5

CD100 Alone or with CD40L Stimulates an Increase in B Cell Survival

Figure 10:
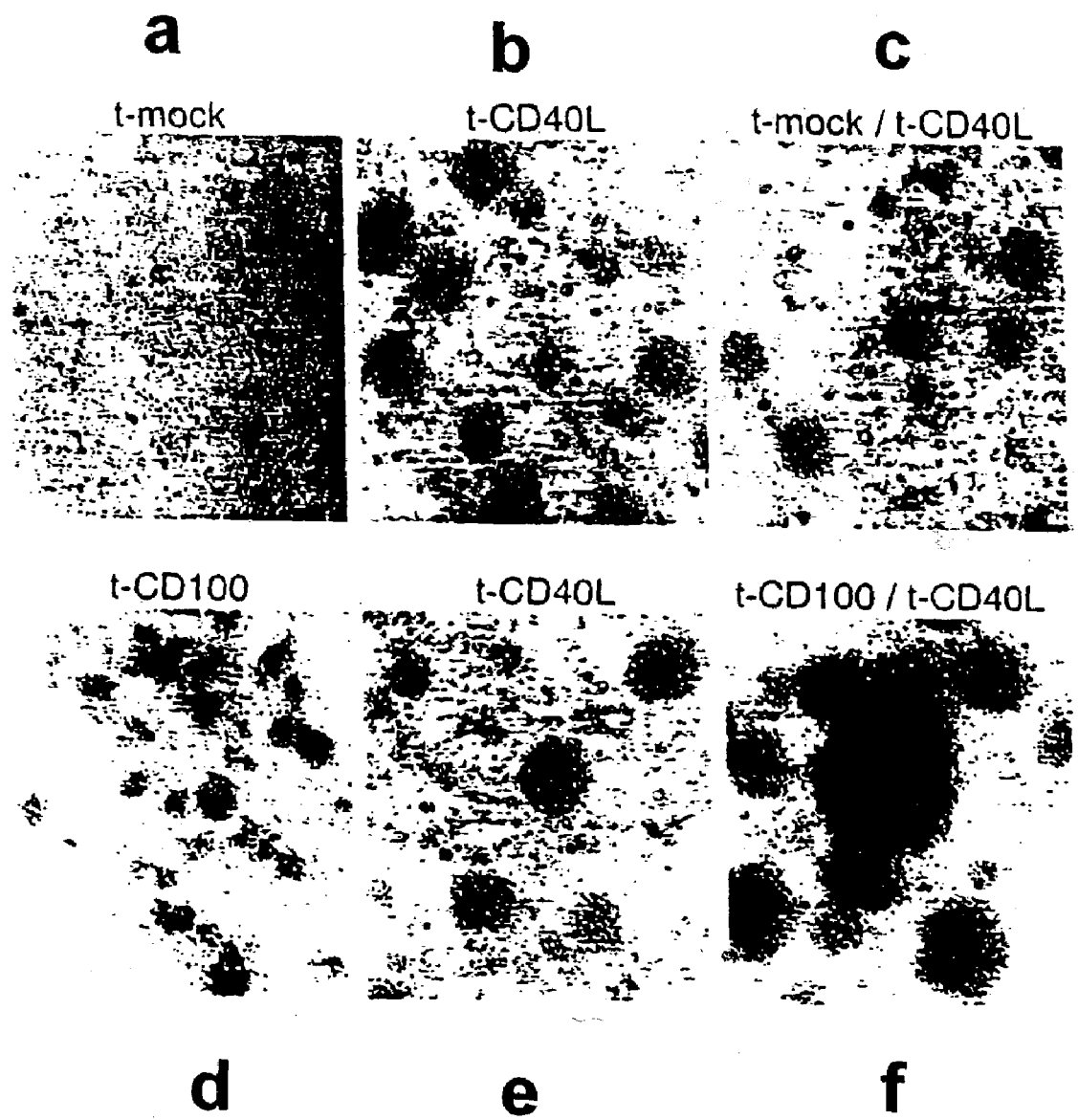
FIG. 10 are photographs depicting human splenic B cells cultured with mock transfected NIH-3T3 cells (t-mock) (FIG. 10a); CD40L transfected NIH-3T3 cells (tCD40L.
Figure 11:
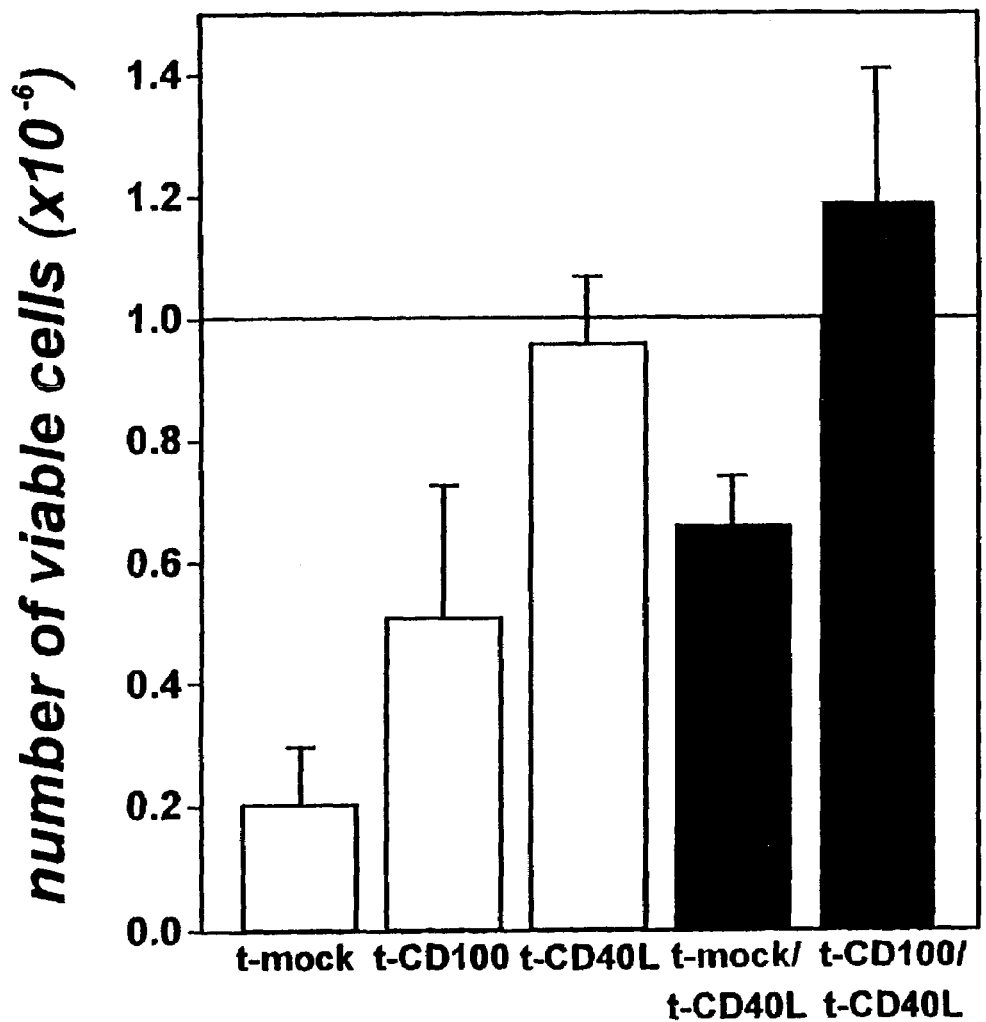
FIG. 11 depicts a histogram showing the number of viable human B cells ($\times 10^6$) after incubation of $10^6$ B cells for 72 hours with mock transfected NIH-3T3 cells (t-mock); CD100 transfected NIH-3T3 cells (t-CD100); CD40 transfected NIH-3T3 cells (t-CD40); 50% mock transfected and 50% CD40L transfected NIH-3T3 cells (t-mock/t-CD40L); and 50% CD100 transfected and 50% CD40L transfected NIH-3T3 cells indicating that CD100 and CD40L stimulation prolong B cell survival and that CD100 and CD40L synergistically stimulate B cell survival.

To determine whether t-CD100/t-CD40L had an effect on B cell survival and/or proliferation, the number of viable B cells was determined by Trypan blue exclusion analysis after 3 days of co-culture according to the conditions described above. As shown in FIG. 10, co-culture with t-mock cells resulted in significant numbers of B cells dying during the culture period. Co-culture with t-CD100 increased the number of viable cells compared to t-mock, but there were consistently fewer cells than observed with t-CD40L. t-CD100/t-CD40L stimulation consistently resulted in significantly greater numbers of B cells than the t-mock/t-CD40L control.

To further distinguish between viability and cellular proliferation, $^3$H-thymidine incorporation was also assessed on day 3. As expected, t-CD40L induced significant B cell proliferation, whereas neither t-mock nor t-CD100 induced significant proliferation. Proliferation induced by the combination of t-CD100/t-CD40L was not significantly greater than that observed with t-CD40L/t-mock demonstrating that the effect of CD100 signaling is likely to be on viability rather than on proliferation.

Example 6

CD100 Stimulation of B Cells Reduces CD40L Induced Increase in CD23 Expression This example shows that in addition to synergizing with CD40L in inducing B cell clustering, CD100 modifies CD40L signaling by reducing CD23 induction induced by CD40L.

Figure 9:
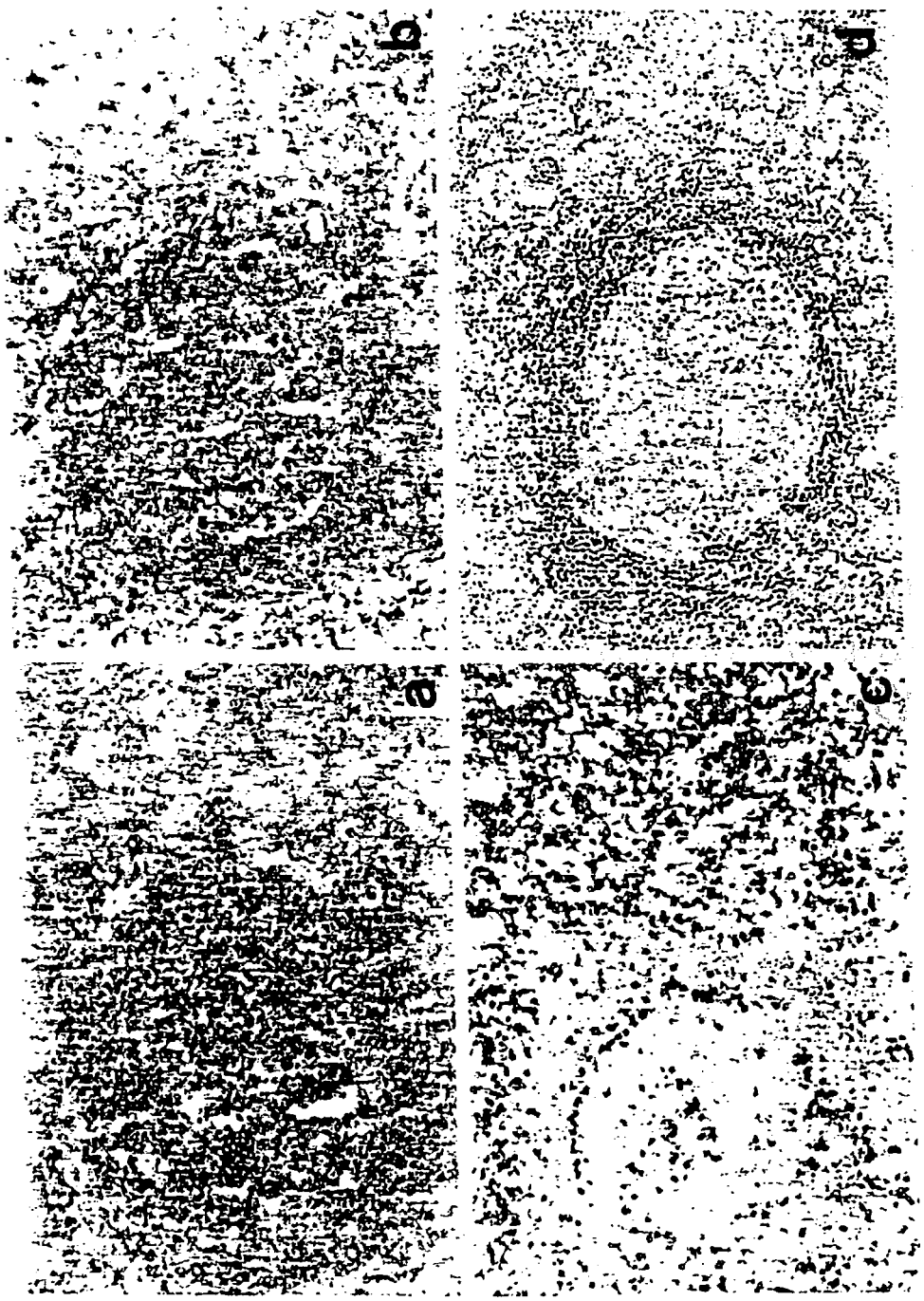
FIGS. 9 a-c are photographs depicting cryostat sections of lymphoid tissue immunostained with a CD100 monoclonal antibody (FIG. 9a), a CD20 monoclonal antibody (FIG. 9b) and a CD3 monoclonal antibody (FIG. 9c).

A two-color FACS analysis of human splenic B cells was performed after 72 hours of co-culture with t-mock/t-CD40L cells or t-CD100/t-CD40L as described in FIG. 9. Cells were stained with CD19 conjugated to phycoerythrin and CD23 conjugated to fluorescein isothiocyanate (Coulter, Hialeah, Fla.). Non-viable cells were excluded by propidium iodide counterstaining prior to analysis.

Figure 12:
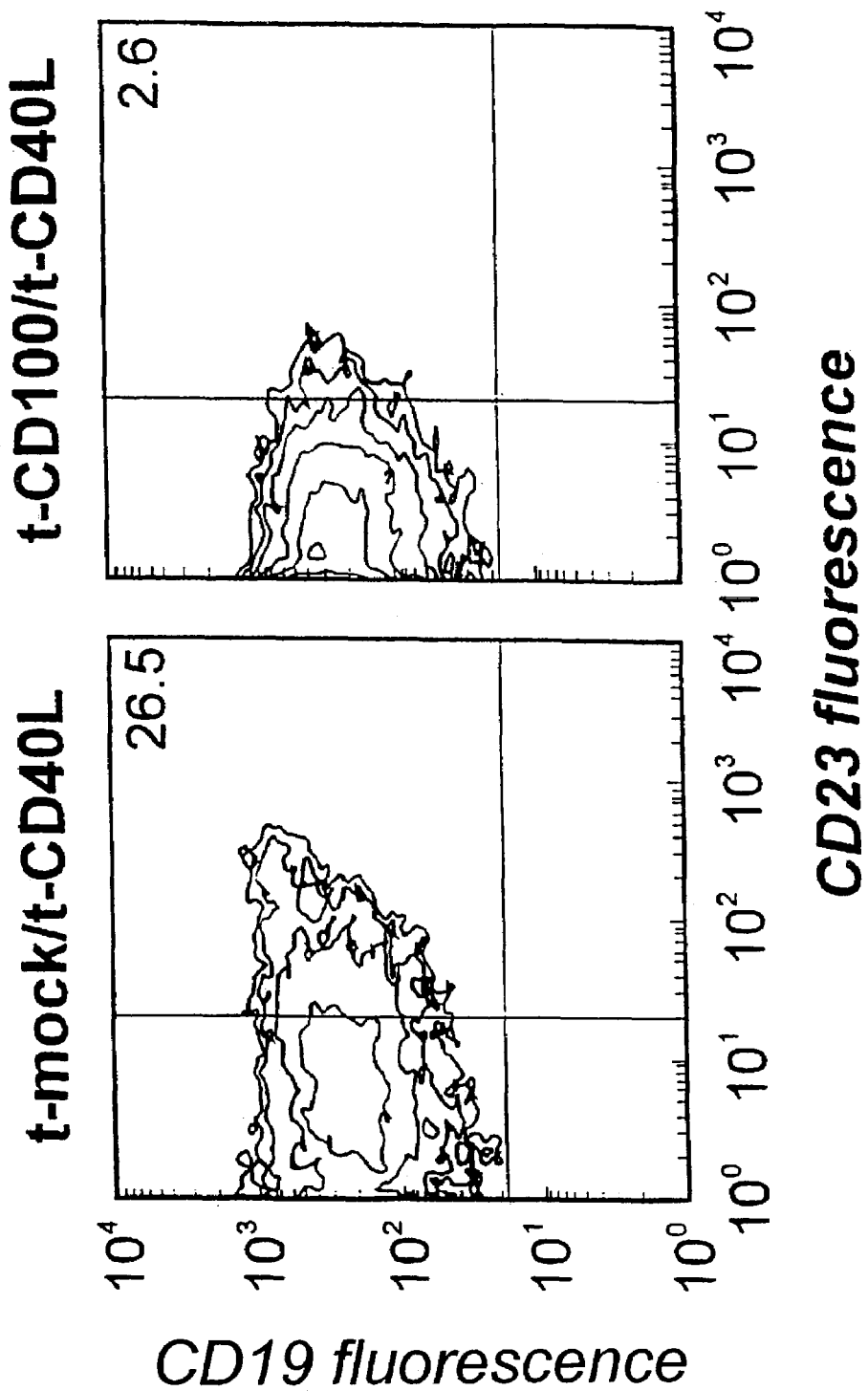
FIG. 12 is a graphic representation of a two color FACS analysis performed with anti-CD19 and anti-CD23 antibodies of human splenic B cells performed after 72 hours of co-culture with t-mock/t-CD40L cells or t-CD100/t-CD40L showing that CD100 reduces expression of CD40L-induced CD23 expression.

As shown in FIG. 12, the percentage of CD23+CD19+ cells is consistently reduced (50-90% reduction) when the CD40L signal is delivered in the presence of CD100. In contrast, CD100 does not modify the induction of B family costimulatory molecules. These results indicate that the CD100 signal not only amplifies the CD40L viability signal but also modifies the CD40L differentiative signal and therefore is likely to be important for the generation, organization, and/or regulation of B cells within the germinal center.

Example 7

CD100 Stimulates T Cell Proliferation

The previous examples demonstrated that CD100 stimulating B cells to aggregate, extends their lifespan, and reduces the expression of CD23. This example demonstrates that CD100 can also provide a costimulatory signal to T cells.

$5 \times 10^4$ CD4+ T cells were cultured in media, with an anti-CD3 antibody at 1 µg/ml, with an anti-CD3 antibody at 1 µg/ml and $2 \times 10^4$ NIH-3T3 cells transfected with B7-1 (tB7-1), with an anti-CD3 antibody at 1 µg/ml and $2 \times 10^4$ NIH-3T3 cells transfected with B2 (t-B7-2), or with an anti-CD3 antibody at 1 µg/ml and $2 \times 10^4$ t-CD100 cells. $^3$H-thymidine incorporation was assessed on day 3.

Figure 13:
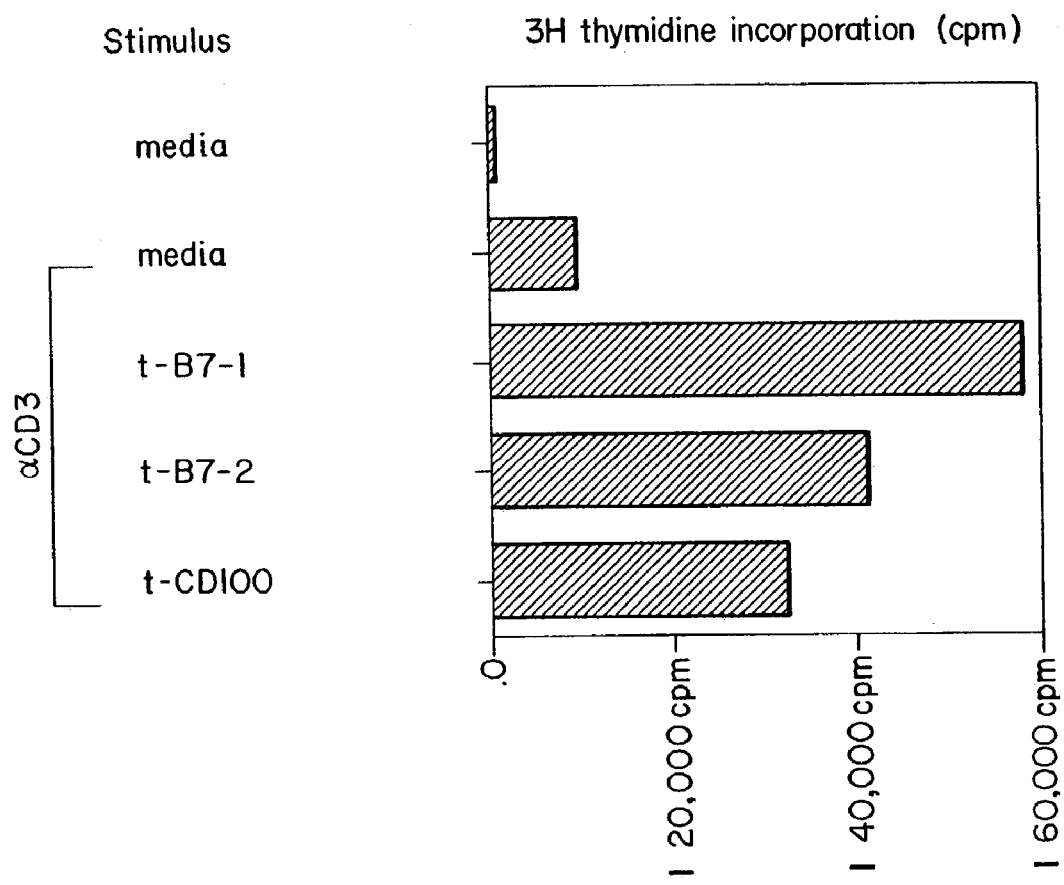
FIG. 13 depicts the results of proliferation assays of CD4+ T cells incubated in media alone, with an anti-CD3 antibody, with an anti-CD3 antibody and NIH-3T3 cells transfected with a B7-1 cDNA (t-B7-1), with an anti-CD3 antibody and NIH-3T3 cells transfected with a B7-2 cDNA (t-B7-2), and with an anti-CD3 antibody and NIH-3T3 cells transfected with a CD100 cDNA (t-CD100) showing that CD100 is a T cell costimulatory molecule.

The results are shown in FIG. 13. The results indicate that, similarly to t-B7-1 and t-B7-2, t-CD100 stimulate the proliferation of CD4+ T cells. Thus, these results indicate that CD100 is capable of stimulating the proliferation of T cells in the presence of a primary activation signal.

Figure 14:
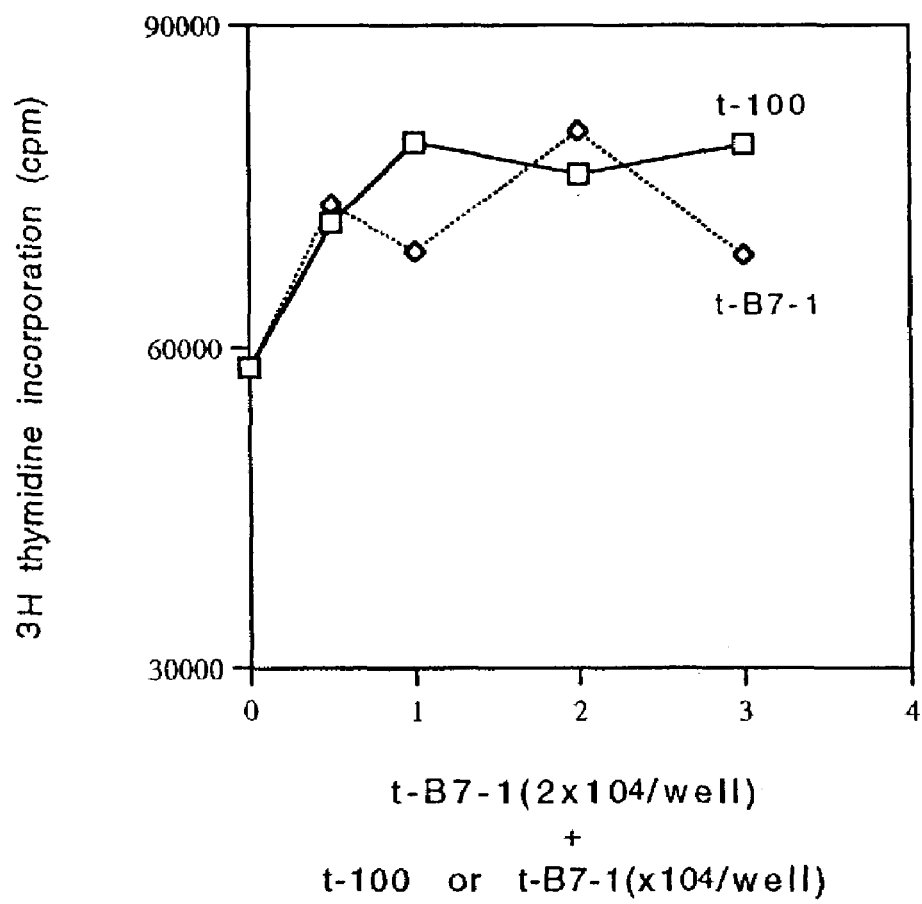
FIG. 14 depicts the results of proliferation assays of CD4+ T cells incubated with and anti-CD3 antibody and $2\times10^4$ t-B7-1 cells and 0, $1\times10^4$, $2\times10^4$, or $3\times10^4$ t-B7-1 or t-CD100 cells.

In another example the costimulatory effect of various amounts of t-CD100 cells on CD4+ T cells was assessed. $5 \times 10^4$ CD4+ T cells were incubated with 1 µg/ml anti-CD3 antibody, $2 \times 10^4$ t-B7-1 cells and 0, $1 \times 10^4$, $2 \times 10^4$, or $3 \times 10^4$ t-CD100 cells or t-B7-1 cells. $^3$H-thymidine incorporation was assessed on day 3. The results, which are presented in FIG. 14, indicate that the level of T cell proliferation increases progressively with increasing amounts of t-CD100 cells. The level of T cell proliferation obtained by incubating T cells with a mixture of t-B7-1 and t-CD100 cells is similar to the level of T cell proliferation obtained by incubating T cells with t-CD100.

Figure 15:
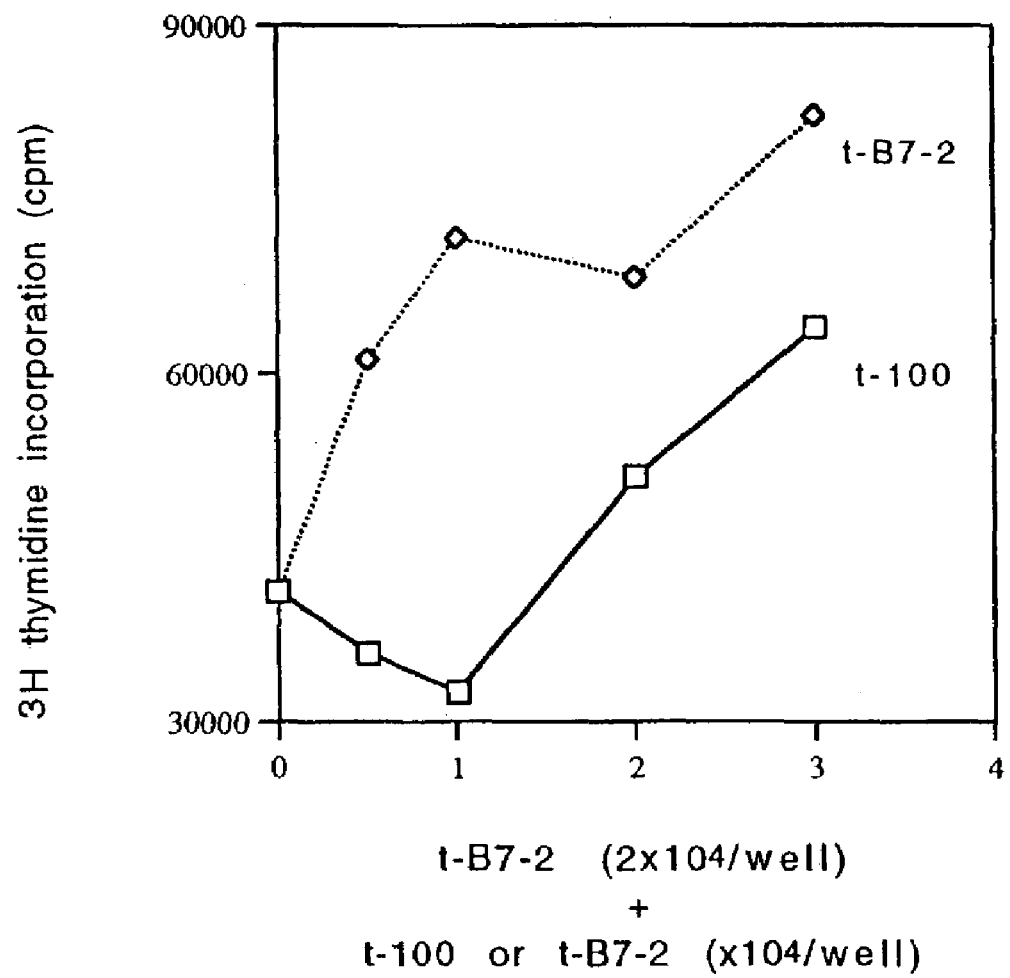
FIG. 15 depicts the results of proliferation assays of CD4+ T cells incubated with and anti-CD3 antibody and $2\times10^4$ t-B7-2 cells and 0, $1\times10^4$, $2\times10^4$, or $3\times10^4$ t-B7-2 or t-CD100 cells.

In a similar experiment, $5 \times 10^4$ CD4+ T cells were incubated with 1 µg/ml anti-CD3 antibody, $2 \times 10^4$ t-B7-2 cells and 0, $1 \times 10^4$, $2 \times 10^4$, or $3 \times 10^4$ t-CD100 cells or t-B7-2 cells and thymidine incorporation was determined after 3 days of culture. The results, shown in FIG. 15, indicate that T cell proliferation increases progressively with increasing amounts of t-CD100 and t-B7-2 cells.

Thus, CD100 is capable of stimulating T cells to proliferate in the presence of a primary activation signal.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for inhibiting a B cell response, said method comprising contacting a population of B cells with an antibody to CD100, wherein said antibody binds CD100 and inhibits a CD100 ligand-associated signal, wherein said B cell response is differentiation of a B cell.

2. The method of claim 1, wherein said antibody is a monoclonal antibody.

3. The method of claim 2, wherein said monoclonal antibody is a humanized antibody.

4. A method for inhibiting a B cell response in a subject, said method comprising administering to said subject a composition comprising an antibody to CD100, wherein said antibody binds CD100 and inhibits a CD100 ligand-associated signal, wherein said B cell response is differentiation of a B cell.

5. The method of claim 4, wherein said antibody is a monoclonal antibody.

6. The method of claim 5, wherein said monoclonal antibody is a humanized antibody.

* * * * *